United States Patent
Alcaraz et al.

(10) Patent No.: US 6,492,355 B1
(45) Date of Patent: Dec. 10, 2002

(54) ADAMANTANE DERIVATIVES

(75) Inventors: Lilian Alcaraz, Loughborough (GB); Mark Furber, Keworth (GB); Michael P. Mortimore, West Bridgford (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/555,489

(22) PCT Filed: Apr. 6, 2000

(86) PCT No.: PCT/SE00/00663
§ 371 (c)(1),
(2), (4) Date: Jun. 1, 2000

(87) PCT Pub. No.: WO00/61569
PCT Pub. Date: Oct. 19, 2000

(30) Foreign Application Priority Data

Apr. 9, 1999 (SE) .............................................. 9901270
Feb. 1, 2000 (GB) .............................................. 0002330

(51) Int. Cl.[7] ........................ A61K 31/395; A61P 37/00; C07D 295/04; C07D 207/04; C07D 211/04
(52) U.S. Cl. ............... 514/218; 514/230.5; 514/252.12; 514/255.03; 514/256; 514/278; 514/299; 514/300; 514/305; 514/325; 514/357; 514/412; 514/424; 514/426; 514/428; 548/453; 548/528; 546/16; 546/112; 546/122; 546/133; 546/203; 546/285; 544/105; 544/294; 544/380; 540/575
(58) Field of Search .......................... 540/575; 544/105, 544/294, 380; 546/16, 112, 122, 133, 203, 285; 548/453, 528; 514/218, 230.5, 252.12, 255.03, 256, 278, 299, 300, 305, 325, 357, 412, 424, 426, 428

(56) References Cited

U.S. PATENT DOCUMENTS 3,464,998 A 9/1969 Krimmel .................. 260/295.5
3,789,072 A 1/1974 Bernstein ................ 260/557 B

FOREIGN PATENT DOCUMENTS

EP 0 395 093 10/1990
WO 95/04720 2/1995
WO 97/32882 9/1997
WO 99/29660 6/1999
WO 99/29661 6/1999

OTHER PUBLICATIONS

J. Am. Chem. Soc., pp. 7215–6, vol. 118, No. 30, 1996 Wolfe et al.
J. Am. Chem. Soc., p. 3395–6, vol. 119, No. 14, 1997 Palucki et al.
Syn. Lett. pp. 379–380 (1998), Billotle.
Journal of Medicinal Chemistry, vol. 41, No. 22, pp. 4273–7278 (1998), Zeng et al.
Journal of Organic Chemistry, vol. 61, No. 25, pp. 8811–8818 (1996), Smith et al.
Journal of Medicinal Chemistry, vol. 42, No. 12, pp. 2180–2190 (1999), Liverton et al.
Org. Synth. vol. 56, pp. 118–122 (1997), Claxton et al.
Bull. Chem. Soc. Jpn., vol. 56, (1983), No. 10, p3199–3200, Nomura et al.
Tetrahedron Lett., vol. 34, (1993), No. 10, p1639–1642 Tsunoda et al.
Abstract from 27–Heterocycles, vol. 86, p. 89562 (1977).
Narayanan, "Adamantyl Analogs of . . . ," J. Med. Chem., vol. 15, No. 11, pp. 1180–1182 (1972).

Primary Examiner—Brenda Coleman
(74) Attorney, Agent, or Firm—Nixon & Vanderhye

(57) ABSTRACT

The invention provides compounds of general formula

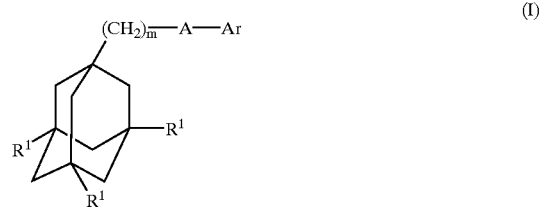

(I)

in which m, A, R[1] and Ar have the meanings defined in the specification; a process for their preparation; pharmaceutical compositions containing them; a process for preparing the pharmaceutical compositions; and their use in therapy.

12 Claims, No Drawings

ADAMANTANE DERIVATIVES

This application is a national stage entry under 35 U.S.C. 371 of PCT/SE00/00663, filed Apr. 6, 2000.

The present invention relates to adamantane derivatives, a process for their preparation, pharmaceutical compositions containing them, a process for preparing the pharmaceutical compositions, and their use in therapy.

Adamantane derivatives are known in the art, e.g. from WO 95/04720 for use as gastrin and cholecystokinin receptor ligands, from Chem. Abs. (1977), Volume 86, No. 13 (86: 89560d) for use as analgesics, and from U.S. Pat. No. 3,464,998 as antibiotics.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β(IL 1β1 ) and giant cell formation (macrophages/microglial cells), degranulation (mast cells) and proliferation (T cells), apoptosis and L-selectin shedding (lymphocytes). P2X₇ receptors are also located on antigen-presenting cells (APC), keratinocytes, salivary acinar cells (parotid cells), hepatocytes and mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

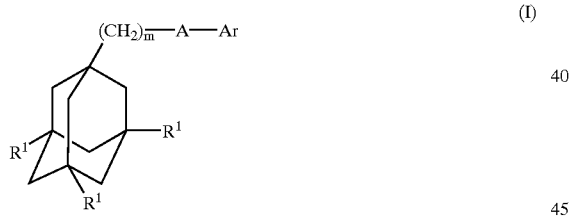

wherein m represents 1, 2 or 3, preferably 1 or 2;

each $R^1$ independently represents a hydrogen or halogen (e.g. fluorine, chlorine, bromine or iodine) atom, preferably a hydrogen atom;

A represents C(O)NH or, preferably, NHC(O);

Ar represents a group

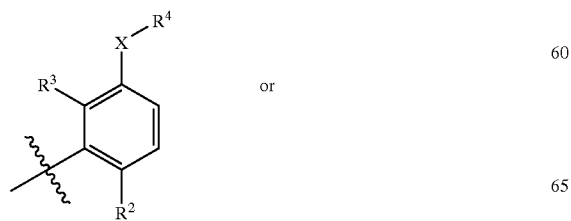

or

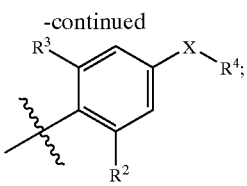

X represents a bond, an oxygen atom or a group CO, $(CH_2)_{1-6}$, CH=, $(CH_2)_{1-6}O$, $O(CH_2)_{1-6}$, $O(CH_2)_{2-6}O$, $O(CH_2)_{2-3}O(CH_2)_{1-3}$, CR'(OH), $(CH_2)_{1-3}O(CH_2)_{1-3}$, $(CH_2)_{1-3}O(CH_2)_{2-3}O$, $NR^5$, $(CH_2)_{1-6}NR^5$, $NR^5(CH_2)_{1-6}$, $(CH_2)_{1-3}NR^5(CH_2)_{1-3}$, $O(CH_2)_{2-6}NR^5$, $O(CH_2)_{2-3}NR^5(CH_2)_{1-3}$, $(CH_2)_{1-3}NR^5(CH_2)_{2-3}O$, $NR^5(CH_2)_{2-6}O$, $NR^5(CH_2)_{2-3}O(CH_2)_{1-3}$, $CONR^5$, $NR^5CO$, $S(O)_n$, $S(O)_nCH_2$, $CH_2S(O)_n$, $SO_2NR^5$ or $NR^5SO_2$;

n is 0, 1 or 2;

R' represents a hydrogen atom or a $C_1-C_6$ alkyl, preferably methyl, group;

one of $R^2$ and $R^3$ represents a halogen, cyano, nitro, amino, hydroxyl, or a group selected from (i) $C_1-C_6$ alkyl optionally substituted by at least one $C_3-C_6$ cycloalkyl, (ii) $C_3-C_8$ cycloalkyl, (iii) $C_1-C_6$ alkyloxy optionally substituted by at least one $C_3-C_6$ cycloalkyl, and (iv) $C_3-C_8$ cycloalkyloxy, each of these groups being optionally substituted by one or more fluorine atoms, and the other of $R^2$ and $R^3$ represents a hydrogen or halogen atom;

either $R^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, $C_1-C_6$ alkyl, $C_1-C_6$ hydroxyalkyl, —$NR^6R^7$, —$(CH_2)_rNR^6R^7$ and —$CONR^6R^7$, or $R^4$ represents a 3- to 8-membered saturated carbocyclic ring system substituted by one or more substituents independently selected from —$NR^6R^7$, —$(CH_2)_rNR^6R^7$ and —$CONR^6N^7$, the ring system being optionally further substituted by one or more substituents independently selected from fluorine atoms, hydroxyl and $C_1-C_6$ alkyl;

r is 1, 2, 3, 4, 5 or 6;

$R^5$ represents a hydrogen atom or a $C_1-C_6$ alkyl or $C_3-C_8$ cycloalkyl group;

$R^6$ and $R^7$ each independently represent a hydrogen atom or a $C_1-C_6$ alkyl, $C_2-C_6$ hydroxyalkyl or $C_3-C_8$ cycloalkyl group, or $R^6$ and $R^7$ together with the nitrogen atom to which they are attached form a 3- to 8-membered saturated heterocyclic ring; with the provisos that, (a) when A represents C(O)NH and $R^4$ represents an unsubstituted 3- to 8-membered saturated aliphatic heterocyclic ring system containing one nitrogen atom, then X is other than a bond, and (b) when A represents C(O)NH and X represents a group $(CH_2)_{1-6}$ or $O(CH_2)_{1-6}$, then $R^4$ does not represent an unsubstituted imidazolyl, unsubstituted morpholinyl, unsubstituted piperidinyl or unsubstituted pyrrolidinyl group, and (c) when A represents NHC(O) and $R^4$ represents an unsubstituted 3- to 8-membered saturated aliphatic heterocyclic ring system containing one nitrogen atom, then X is other than a bond, and (d) when A represents NHC(O) and X represents $O(CH_2)_{1-6}$, $NH(CH_2)_{1-6}$ or $SCH_2$, then $R^4$ does not represent an unsubstituted 1-piperidinyl or unsubstituted 1-pyrrolidinyl group, and (e) when A represents NHC(O) and X represents $O(CH_2)_{2-3}NH(CH_2)_2$, then $R^4$ does not represent an imidazolyl group;

or a pharmaceutically acceptable salt or solvate thereof.

In the context of the present specification, unless otherwise indicated, an alkyl substituent or alkyl moiety in a substituent group may be linear or branched. Examples of alkyl groups/moieties containing up to 6 carbon atoms include methyl, ethyl, propyl, isopropyl, butyl, isobutyl, tert-butyl, pentyl and hexyl. When one of $R^2$ and $R^3$ represents a $C_1$–$C_6$ alkyl/$C_1$–$C_6$ alkyloxy optionally substituted by at least one $C_3$–$C_6$ cycloalkyl, it should be understood that one or both of the alkyl and cycloalkyl moieties may be optionally substituted by fluorine atoms. In relation to $R^4$, a 3- to 9-membered saturated or unsaturated aliphatic heterocyclic ring system containing one or two nitrogen atoms and optionally an oxygen atom may be a monocyclic or bicyclic ring system. Further in relation to $R^4$, a 3- to 8-membered saturated carbocyclic ring system may be a monocyclic or bicyclic ring system. When $R^6$ or $R^7$ represents a $C_2$–$C_6$ hydroxyalkyl in the substituent $NR^6R^7$, —$(CH_2)_rNR^6R^7$ or —$CONR^6R^7$, it will be appreciated that the hydroxyl group will not be bonded to the same carbon atom as the nitrogen atom. When $R^6$ and $R^7$ together with the nitrogen atom to which they are attached form a 3- to 8-membered saturated heterocyclic ring, the ring obtained is monocyclic.

Preferably X represents a bond, an oxygen atom or a group CO, $(CH_2)_{1-6}$, CH=, $O(CH_2)_{1-6}$, $O(CH_2)_{2-6}O$, $O(CH_2)_{2-3}O(CH_2)_{1-3}$, CR'(OH), $NR^5$, $(CH_2)_{1-6}NR^5$, $CONR^5$, $S(O)_n$ or $S(O)_nCH_2$.

One of $R^2$ and $R^3$ represents a halogen (e.g. fluorine, chlorine, bromine or iodine), cyano, nitro, amino, hydroxyl, or a group selected from (i) $C_1$–$C_6$ alkyl, preferably $C_1$–$C_4$ alkyl, optionally substituted by at least one (e.g. 1, 2 or 3) $C_3$–$C_6$ cycloalkyl (i.e. cyclopropyl, cyclobutyl, cyclopentyl or cyclohexyl), (ii) $C_3$–$C_8$ cycloalkyl (e.g. cyclopropyl, cyclobutyl, cyclopentyl or cyclohexyl), (iii) $C_1$–$C_6$ alkyloxy, preferably $C_1$–$C_4$ alkyloxy, optionally substituted by at least one (e.g. 1, 2 or 3) $C_3$–$C_6$ cycloalkyl (i.e. cyclopropyl, cyclobutyl, cyclopentyl or cyclohexyl), and (iv) $C_3$–$C_8$ cycloalkyloxy (e.g. cyclopropyloxy, cyclobutyloxy, cyclopentyloxy or cyclohexyloxy), each of these groups being optionally substituted by one or more (e.g. 1, 2, 3 or 4) fluorine atoms, and the other of $R^2$ and $R^3$ represents a hydrogen or halogen (e.g. fluorine, chlorine, bromine or iodine) atom.

Preferably, one of $R^2$ and $R^3$ represents a halogen (especially chlorine or bromine) atom or a nitro, amino or $C_1$–$C_6$ alkyl (especially methyl or ethyl) group and the other of $R^2$ and $R^3$ represents a hydrogen atom.

$R^4$ may represent a 3- to 9-membered saturated or unsaturated aliphatic heterocyclic ring system containing one or two nitrogen atoms and optionally an oxygen atom, the heterocyclic ring system being optionally substituted by one or more (e.g. 1, 2, 3 or 4) substituents independently selected from fluorine atoms, hydroxyl, carboxyl, cyano, $C_1$–$C_6$ alkyl, preferably $C_1$–$C_4$ alkyl, $C_1$–$C_6$ hydroxyalkyl, preferably $C_1$–$C_4$ hydroxyalkyl, —$NR^6R^7$, —$(CH_2)_rNR^6R^7$ and —$CONR^6R^7$.

The 3- to 9-membered saturated or unsaturated aliphatic heterocyclic ring system in the group $R^4$ may be a monocyclic ring system such as pyrrolidinyl (e.g. 1-pyrrolidinyl, 2-pyrrolidinyl or 3-pyrrolidinyl), piperidinyl (e.g. 1-piperidinyl, 2-piperidinyl, 3-piperidinyl or 4-piperidinyl), 4-piperiden-3-yl, piperazinyl (e.g. 1-piperazinyl), homopiperazinyl,

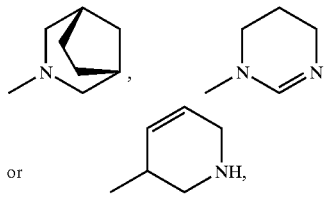

or a bicyclic ring system such as

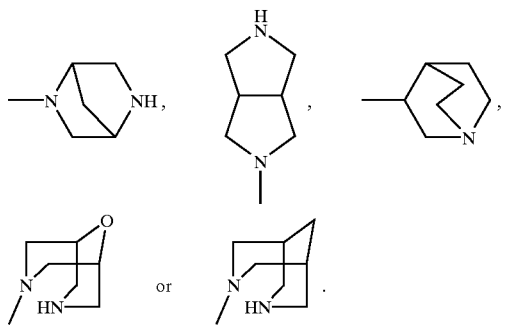

Alternatively, $R^4$ may represent a 3- to 8-membered saturated carbocyclic ring system substituted by one or more (e.g. 1, 2 or 3) substituents independently selected from $NR^6R^7$, —$(CH_2)_rNR^6R^7$ and —$CONR^6R^7$, the ring system being optionally further substituted by one or more (e.g. 1, 2, 3 or 4) substituents independently selected from fluorine atoms, hydroxyl and $C_1$–$C_6$ alkyl, preferably $C_1$–$C_4$ alkyl.

The 3- to 8-membered saturated carbocyclic ring in the group $R^4$ is preferably a monocyclic ring system such as a cyclopentyl or cyclohexyl ring.

Specific examples of groups $R^4$ include:

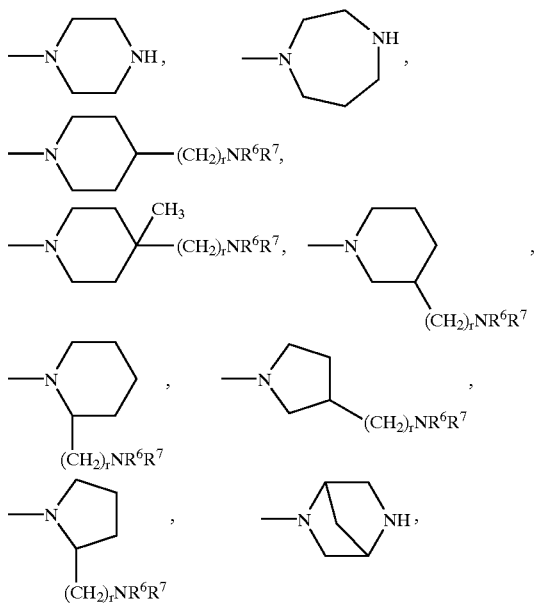

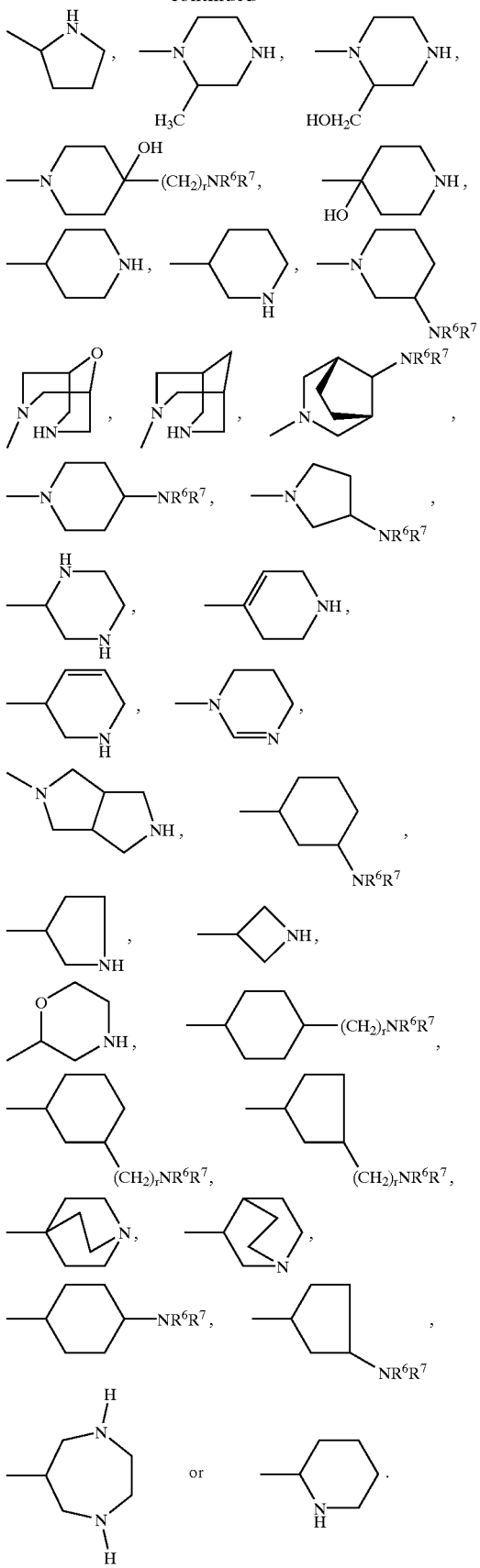
When X represents a bond or a group CO, $(CH_2)_{1-6}$, $O(CH_2)_{2-6}$, $O(CH_2)_{2-3}O(CH_2)_{2-3}$, $(CH_2)_{1-3}O(CH_2)_{2-3}$, $NR^5(CH_2)_{2-6}$, $(CH_2)_{1-3}NR^5(CH_2)_{2-3}$, $O(CH_2)_{2-3}NR^5(CH_2)_{2-3}$, $NR^5(CH_2)_{2-3}O(CH_2)_{2-3}$, $NR^5CO$, $SO_2$ or $NR^5SO_2$, $R^4$ preferably represents a group:
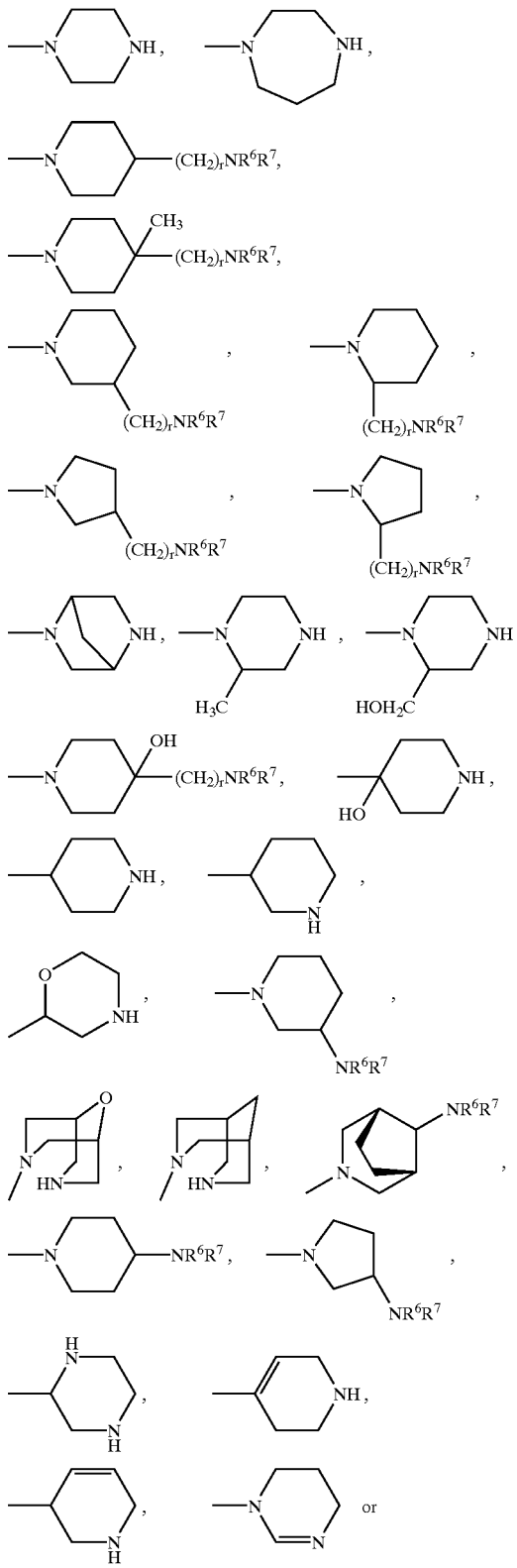

-continued

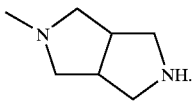

When X represents an oxygen or sulphur atom or a group CH=, $(CH_2)_{1-6}O$, $OCH_2$, $O(CH_2)_{2-6}O$, $O(CH_2)_{2-3}OCH_2$, $CR'OH$, $(CH_2)_{1-3}OCH_2$, $(CH_2)_{1-3}O(CH_2)_{2-3}O$, $NR^5$, $(CH_2)_{1-6}NR^5$, $O(CH_2)_{2-6}NR^5$, $NR^5CH_2$, $(CH_2)_{1-3}NR^5CH_2$, $O(CH_2)_{2-3}NR^5CH_2$, $(CH_2)_{1-3}NR^5(CH_2)_{2-3}O$, $NR^5(CH_2)_{2-6}O$, $NR^5(CH_2)_{2-3}OCH_2$, $CONR^5$, $SO$, $S(O)_nCH_2$, $CH_2S(O)_n$ or $SO_2NR^5$, $R^4$ preferably represents a group:

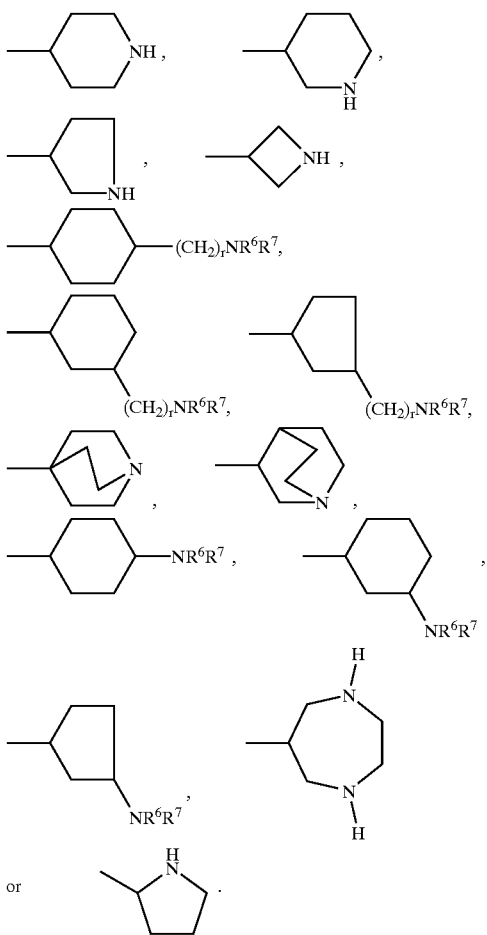

$R^5$ represents a hydrogen atom, or a $C_1$–$C_6$, preferably $C_1$–$C_4$, alkyl (e.g. methyl, ethyl, propyl, butyl, pentyl or hexyl) or $C_3$–$C_8$, preferably $C_3$–$C_6$, cycloalkyl (e.g. cyclopropyl, cyclobutyl, cyclopentyl or cyclohexyl) group.

$R^6$ and $R^7$ each independently represent a hydrogen atom, or a $C_1$–$C_6$, preferably $C_1$–$C_4$, alkyl (e.g. methyl, ethyl, propyl, butyl, pentyl or hexyl), $C_2$–$C_6$ hydroxyalkyl or $C_3$–$C_8$, preferably $C_3$–$C_6$, cycloalkyl (e.g. cyclopropyl, cyclobutyl, cyclopentyl or cyclohexyl) group, or $R^6$ and $R^7$ together with the nitrogen atom to which they are attached form a 3- to 8-membered, preferably 3- to 6-membered, saturated heterocyclic ring such as a pyrrolidinyl or piperidinyl ring.

Preferred compounds of the invention include:

2-Nitro-3-piperazin-1-yl-N-(tricyclo[3.3.1.1$^{3,7}$]dec-1-ylmethyl)-benzamide,

2-Amino-3-piperazin-1-yl-N-(tricyclo[3.3.1.1$^{3,7}$]dec-1-ylmethyl)-benzamide, dihydrochloride salt, 2-Chloro-3-piperazin-1-yl-N-(tricyclo[3.3.1.1$^{3,7}$]dec-1-ylmethyl)-benzamide, 2-Chloro-5-piperazin-1-yl-N-(tricyclo[3.3.1.1$^{3,7}$]dec-1-ylmethyl)-benzamide, 2-Chloro-5-(hexahydro-1H-1,4-diazepin-1-yl)-N-(tricyclo[3.3.1.1$^{3,7}$]dec-1-ylmethyl)-benzamide, hydrochloride salt, 5-(4-Amino-1-piperidinyl)-2-chloro-N-(tricyclo[3.3.1.1$^{3,7}$]dec-1-ylmethyl)-benzamide, hydrochloride salt, (+/−)-5-(3-Amino-1-pyrrolidinyl)-2-chloro-N-(tricyclo[3.3.1.1$^{3,7}$]dec-1-ylmethyl)-benzamide, hydrochloride salt, 2-Chloro-5-piperazin-1-ylmethyl-N-(tricyclo[3.3.1.1$^{3,7}$]dec-1-ylmethyl)-benzamide, hydrochloride salt, 2-Chloro-5-[(hexahydro-1H-1,4-diazepin-1-yl)methyl]-N-(tricyclo[3.3.1.1 $^{3,7}$]dec-1-ylmethyl)-benzamide, hydrochloride salt, 5-[(4-Amino-1-piperidinyl)methyl]-2-chloro-N-(tricyclo[3.3.1.1$^{3,7}$]dec-1-ylmethyl)-benzamide, hydrochloride salt, 5-[(3-Amino-1-pyrrolidinyl)methyl]-2-chloro-N-(tricyclo[3.3.1.1$^{3,7}$]dec-1-ylmethyl)-benzamide, hydrochloride salt, 2-Chloro-5-(4-piperidinyloxy)-N-(tricyclo[3.3.1.1$^{3,7}$]dec-1-ylmethyl)-benzamide, hydrochloride salt, (R)-2-Chloro-5-(2-pyrrolidinylmethoxy)-N-(tricyclo[3.3.1.1$^{3,7}$]dec-1-ylmethyl)-benzamide, hydrochloride salt, (S)-2-Chloro-5-(2-pyrrolidinylmethoxy)-N-(tricyclo[3.3.1.1$^{3,7}$]dec-1-ylmethyl)-benzamide, hydrochloride salt, 2-Chloro-5-(3-piperidinylmethoxy)-N-(tricyclo[3.3.1.1$^{3,7}$]dec-1-ylmethyl)-benzamide, hydrochloride salt, cis-5-[(4-Aminocyclohexyl)oxy]-2-chloro-N-(tricyclo[3.3.1.1$^{3,7}$]dec-1-ylmethyl)-benzamide, hydrochloride salt, 2-Methyl-5-(1-piperazinylmethyl)-N-(tricyclo[3.3.1.1$^{3,7}$]dec-1-ylmethyl)-benzamide, hydrochloride salt, 2-Chloro-5-(1-piperazinylmethyl)-N-(2-tricyclo[3.3.1.1$^{3,7}$]dec-1-ylethyl)-benzamide, hydrochloride salt, (+/−)-2-Chloro-5-(3-pyrrolidinyloxy)-N-(tricyclo[3.3.1.1$^{3,7}$]dec-1-ylmethyl)-benzamide, hydrochloride salt, (+/−)-2-Chloro-5-(3-piperidinyloxy)-N-(tricyclo[3.3.1.1$^{3,7}$]dec-1-ylmethyl)-benzamide, hydrochloride salt, trans-5-[(4-Aminocyclohexyl)oxy]-2-chloro-N-(tricyclo[3.3.1.1$^{3,7}$]dec-1-ylmethyl)-benzamide, cis-(+/−)-5-[(3-Aminocyclopentyl)oxy]-2-chloro-N-(tricyclo[3.3.1.1$^{3,7}$]dec-1-ylmethyl)-benzamide, (S,S)-2-Chloro-5-(2,5-diazabicyclo[2.2.1]hept-2-yl)-N-(tricyclo[3.3.1.1$^{3,7}$dec-1-ylmethyl)-benzamide, hydrochloride salt, 2-Chloro-5-(2-methyl 1-piperazinyl)-N-(tricyclo[3.3.1.1$^{3,7}$]dec-1-ylmethyl)-benzamide, hydrochloride salt, (+/−)-2-Chloro-5-(3-pyrrolidinyloxy)-N-(tricyclo[3.3.1.1$^{3,7}$]dec-1-ylmethyl)-benzamide, hydrochloride salt, (+/−)-5-(3-Amino-1-piperidinyl)-2-chloro-N-(tricyclo[3.3.1.1$^{3,7}$]dec-1-ylmethyl)-benzamide, (+/−)-2-Chloro-5-(3-piperidinylamino)-N-(tricyclo[3.3.1.1$^{3,7}$]dec-1-ylmethyl)-benzamide, 2-Chloro-5-[hexahydropyrrolo[3,4-c]pyrrol-2(1H)-yl]-N-(tricyclo[3.3.1.1$^{3,7}$]dec-1-ylmethyl)-benzamide, N-[2-methyl-5-(4-piperidinyloxy)phenyl]-tricyclo[3.3.1.1$^{3,7}$]decane-1-acetamide, hydrochloride salt, N-[2-chloro-5-(4-piperidinyloxy)phenyl]-tricyclo[3.3.1.1$^{3,7}$]decane-1-acetamide, hydrochloride salt, 2-Chloro-5-[(4-piperidinylamino)methyl]-N-(tricyclo[3.3.1.1$^{3,7}$]dec-1-ylmethyl)-benzamide, dihydrochloride salt,
5-[[[4-(Aminomethyl)cyclohexyl]amino]methyl]-2-chloro-N-(tricyclo[3.3.1.1$^{3,7}$]dec-1-ylmethyl)-benzamide, dihydrochloride salt,
5-[[(4-Aminocyclohexyl)amino]methyl]-2-chloro-N-(tricyclo[3.3.1.1$^{3,7}$]dec-1-ylmethyl)-benzamide, dihydrochloride salt,
5-[(1-Azabicyclo[2.2.2]oct-3-ylamino)methyl]-2-chloro-N-(tricyclo[3.3.1.1$^{3,7}$]dec-1-ylmethyl)-benzamide,
N-[4-(3-Aminopyrrolidin-1-yl)-2-methylphenyl]-2-(tricyclo[3.3.1.1$^{3,7}$]dec-1-yl)acetamide, dihydrochloride salt,
N-(2-Methyl-4-piperazin-1-ylphenyl)-2-(tricyclo[3.3.1.1$^{3,7}$]dec-1-yl)acetamide, dihydrochloride salt,
cis-4-(3-Amino-cyclopentyloxy)-2-chloro-N-(tricyclo[3.3.1.1$^{3,7}$]dec-1-ylmethyl)-benzamide, hydrochloride salt,
2-Chloro4-(4-piperidinyloxy)-N-(tricyclo[3.3.1.13,7]dec-1-ylmethyl)-benzamide, hydrochloride salt,
(+/−)-2-Chloro-4-(pyrrolidin-3-yloxy)-N-(tricyclo[3.3.1.1$^{3,7}$]dec-1-ylmethyl)-benzamide,
2-Chloro-4-(piperidin-3-yloxy)-N-(tricyclo[3.3.1.1$^{3,7}$]dec-1-ylmethyl)-benzamide, hydrochloride salt,
2-Chloro4-(4-piperazin-1-yl)-N-(tricyclo[3.3.1.1$^{3,7}$]dec-1-ylmethyl)-benzamide, hydrochloride salt,
2-Chloro-4-(3-pyrrolidinylamino)-N-(tricyclo[3.3.1.1$^{3,7}$]dec-1-ylmethyl)-benzamide, hydrochloride salt,
2-Chloro-4-(hexahydro-1H-1,4-diazepin-1-yl)-N-(tricyclo[3.3.1.1$^{3,7}$]dec-1-ylmethyl)-benzamide, hydrochloride salt,
(±)-5-[(3-Amino-1-piperidinyl)methyl]-2-chloro-N-(tricyclo[3.3.1.1$^{3,7}$]dec-1-ylmethyl)-benzamide, hydrochloride salt,
2-Chloro-5-(2,5-diazabicyclo[2.2.1]hept-2-ylmethyl)-N-(tricyclo[3.3.1.1$^{3,7}$]dec-1-ylmethyl)-benzamide, hydrochloride salt,
2-Chloro-5-(9-oxa-3,7-diazabicyclo[3.3.1]non-3-ylmethyl)-N-(tricyclo[3.3.1.1$^{3,7}$]dec-1-ylmethyl)-benzamide, hydrochloride salt,
2-Chloro-5-(3,7-diazabicyclo[3.3.1]non-3-ylmethyl)-N-(tricyclo[3.3.1.1$^{3,7}$]dec-1-ylmethyl)-benzamide, hydrochloride salt,
trans-2-Chloro-5-[[8-(methylamino)-3-azabicyclo[3.2.1]oct-3-yl]methyl]-N-(tricyclo[3.3.1.1$^{3,7}$]dec-1-ylmethyl)-benzamide, hydrochloride salt,
cis-2-Chloro-5-[(hexahydropyrrolo[3,4-c]pyrrol-2(1H)-yl)methyl]-N-(tricyclo[3.3.1.1$^{3,7}$]dec-1-ylmethyl)-benzamide, hydrochloride salt,
2-Chloro-5-(4-piperidinylidenemethyl)-N-(tricyclo[3.3.1.1$^{3,7}$]dec-1-ylmethyl)-benzamide, hydrochloride salt,
2-Chloro-5-(4-piperidinylmethyl)-N-(tricyclo[3.3.1.1$^{3,7}$]dec-1-ylmethyl)-benzamide, hydrochloride salt,
2-Chloro-5-(4-hydroxy-piperidin-4-yl)-N-(tricyclo[3.3.1.1$^{3,7}$]dec-1-ylmethyl)-benzamide, hydrochloride salt,
2-Chloro-5-(1,2,3,6-tetrahydro-pyridin-4-yl)-N-(tricyclo[3.3.1.1$^{3,7}$]dec-1-ylmethyl)-benzamide, hydrochloride salt,
2-Ethyl-5-piperazin-1-ylmethyl-N-(tricyclo[3.3.1.1$^{3,7}$]dec-1-ylmethyl)-benzamide, hydrochloride salt,
2-Chloro-5-(piperidin-4-ylsulfanyl)-N-(tricyclo[3.3.1.1$^{3,7}$]dec-1-ylmethyl)-benzamide, hydrochloride salt,
2-Chloro-5-(piperidin4-ylsulfinyl)-N-(tricyclo[3.3.1.1$^{3,7}$]dec-1-ylmethyl)-benzamide,
2-Chloro-5-(piperidin4-ylsulfonyl)-N-(tricyclo[3.3.1.1$^{3,7}$]dec-1-ylmethyl)-benzamide, hydrochloride salt,
2-Chloro-5-(piperidin4-ylmethylsulfanyl)-N-(tricyclo[3.3.1.1$^{3,7}$]dec-1-ylmethyl)-benzamide, hydrochloride salt,
2-Chloro-5-(piperidin4-ylmethanesulfonyl)-N-(tricyclo[3.3.1.1$^{3,7}$]dec-1-ylmethyl)-benzamide, hydrochloride salt,
2-Chloro-5-(piperazine-1-carbonyl)-N-(tricyclo[3.3.1.1$^{3,7}$]dec-1-ylmethyl)-benzamide, hydrochloride salt,
2-Chloro-5-([1,4]diazepane-1-carbonyl)-N-(tricyclo[3.3.1.1$^{3,7}$]dec-1-ylmethyl)-benzamide, hydrochloride salt,
4-Chloro-N$^1$-(piperidin4-yl-)-N$^2$-(tricyclo[3.3.1.1$^{3,7}$]dec-1-ylmethyl)-isophthalamide, hydrochloride salt,
2-Chloro-5-(hydroxy4-piperidinylmethyl)-N-(tricyclo[3.3.1.1$^{3,7}$]dec-1-ylmethyl)-benzamide, hydrochloride salt,
(±)-2-Chloro-5-(hydroxy-3-piperidinylmethyl)-N-(tricyclo[3.3.1.1$^{3,7}$]dec-1-ylmethyl)-benzamide, hydrochloride salt,
2-Bromo-5-piperazin-1-ylmethyl-N-(tricyclo[3.3.1.1$^{3,7}$]dec-1-ylmethyl)-benzamide, hydrochloride salt,
2-Chloro-5-[2-(1-piperazinyl)ethyl]-N-(tricyclo[3.3.1.1$^{3,7}$]dec-1-ylmethyl)-benzamide, hydrochloride salt,
2-Chloro-5-[2-(2,5-diazabicyclo[2.2.1]hept-2-yl)ethyl]-N-(tricyclo[3.3.1.1$^{3,7}$]dec-1-ylmethyl)-benzamide, hydrochloride salt,
5-[2-(4-Amino-1-piperidinyl)ethyl]-2-chloro-N-(tricyclo[3.3.1.1$^{3,7}$]dec-1-ylmethyl)-benzamide, hydrochloride salt,
2-Chloro-5-[2-(3-piperidinylamino)ethyl]-N-(tricyclo[3.3.1.1$^{3,7}$]dec-1-ylmethyl)-benzamide, dihydrochloride salt,
5-[2-(3-Amino-1-piperidinyl)ethyl]-2-chloro-N-(tricyclo[3.3.1.1$^{3,7}$]dec-1-ylmethyl)-benzamide, hydrochloride salt,
2-Chloro-5-[2-(3-pyrrolidinylamino)ethyl]-N-(tricyclo[3.3.1.1$^{3,7}$]dec-1-ylmethyl)-benzamide, dihydrochloride salt,
5-[2-[(3R)-3-Aminopyrrolidinyl]ethyl]-2-chloro-N-(tricyclo[3.3.1.1$^{3,7}$]dec-1-ylmethyl)-benzamide, hydrochloride salt,
2-Chloro-5-[2-[2-(hydroxymethyl)-1-piperazinyl]ethyl]-N-(tricyclo[3.3.1.1$^{3,7}$]dec-1-ylmethyl)-benzamide, hydrochloride salt,
2-Chloro-5-(hexahydro-1H-1,4-diazepin-1-yl)-N-(2-tricyclo[3.3.1.1$^{3,7}$]dec-1-ylethyl)-benzamide, hydrochloride salt,
(+/−)-5-(3-Amino-1-pyrrolidinyl)-2-chloro-N-(2-tricyclo[3.3.1.1$^{3,7}$]dec-1-ylethyl)-benzamide, hydrochloride salt,
2-Chloro-5-(4-piperidinylcarbonyl)-N-(tricyclo[3.3.1.1$^{3,7}$]dec-1-ylmethyl)-benzamide, hydrochloride salt,
2-Chloro-5-[1-hydroxy-1-(4-piperidinyl)ethyl]-N-(tricyclo[3.3.1.1$^{3,7}$]dec-1-ylmethyl)-benzamide, hydrochloride salt,
2-Chloro-5-[2-(1-piperazinyl)ethoxy)-N-(tricyclo[3.3.1.1$^{3,7}$]dec-1-ylmethyl)-benzamide, hydrochloride salt,
2-Chloro-5-[2-(4-piperidinyl)ethoxy)-N-(tricyclo[3.3.1.1$^{3,7}$]dec-1-ylmethyl)-benzamide, hydrochloride salt,
2-Chloro-5-[2-(4-piperidinyloxy)ethoxy)-N-(tricyclo[3.3.1.1$^{3,7}$]dec-1-ylmethyl)-benzamide, hydrochloride salt,
2-Chloro-5-[2-[2-(1-piperazinyl)ethoxy]ethoxy]-N-(tricyclo[3.3.1.1$^{3,7}$]dec-1-ylmethyl)-benzamide, hydrochloride salt,
2-Chloro-5-[(5,6-dihydro-1(4H)-pyrimidinyl)methyl]-N-(tricyclo[3.3.1.1$^{3,7}$]dec-1-ylmethyl)-benzamide,
2-Chloro-5-[[4-[(2-hydroxyethyl)amnino]-1-piperidinyl]methyl]-N-(tricyclo[3.3.1.1$^{3,7}$]dec-1-ylmethyl)-benzamide, hydrochloride salt, 2-Chloro-5-[[4-hydroxy4-[[(1-methylethyl)amino]methyl]-1-piperidinyl]methyl]-N-(tricyclo[3.3.1.1$^{3,7}$dec-1-ylmethyl)-benzamide, 2-Chloro-5-[(1,2,3,6-tetrahydro-3-pyridinyl)methyl]-N-(tricyclo[3.3.1.1$^{3,7}$]dec-1-ylmethyl)-benzamide, hydrochloride salt, 2-Chloro-5-(3-piperidinylmethyl)-N-(tricyclo[3.3.1.1$^{3,7}$]dec-1-ylmethyl)-benzamide, acetate salt, 2-bromo-5-[[4-[(2-hydroxyethyl)amino]-1-piperidinyl]methyl]-N-(tricyclo[3.3.1.1$^{3,7}$]dec -1-ylmethyl-benzamide, and 2-Chloro-5-[(E)-3-piperidinylidenemethyl]-N-(tricyclo[3.3.1.1$^{3,7}$]dec-1-ylmethyl)-benzamide.

The present invention further provides a process for the preparation of a compound of formula (I) as defined above which comprises:

(i) when X represents a CH$_2$ group, R$^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, C$_1$–C$_6$ alkyl, C$_1$–C$_6$ hydroxyalkyl, —NR$^6$R$^7$, —(CH$_2$)$_r$NR$^6$R$^7$ and —CONR$^6$R$^7$ and R$^4$is linked to X through a nitrogen atom, reacting a compound of general formula

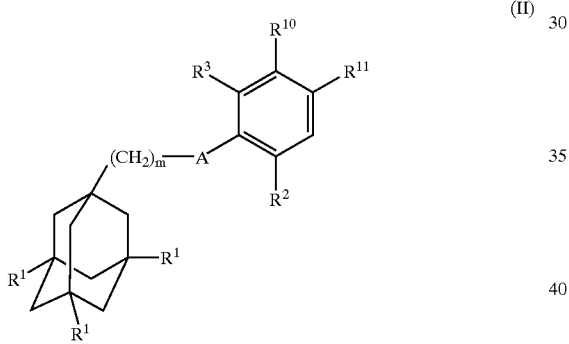

(II)

wherein one of R$^{10}$ and R$^{11}$ represents a hydrogen atom and the other of R$^{10}$ and R$^{11}$ represents a group —CH$_2$L$^1$ in which L$^1$ represents a leaving group (e.g. a halogen atom) and m, A, R$^1$, R$^2$ and R$^3$ are as defined in formula (I), with a compound of general formula

R$^{4'}$—H          (III)

in the presence of a base (e.g. diisopropylethylamine), wherein R$^{4'}$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, C$_1$–C$_6$ alkyl, C$_1$–C$_6$ hydroxyalkyl, —NR$^6$R$^7$, —(CH$_2$)$_r$NR$^6$R$^7$ and —CONR$^6$R$^7$ and wherein R$^6$ and R$^7$ are as defined in formula (I); or (ii) when X represents an oxygen atom or a group O(CH$_2$)$_{1-6}$, O(CH$_2$)$_{2-6}$O, O(CH$_2$)$_{2-3}$O(CH$_2$)$_{1-3}$, O(CH$_2$)$_{2-6}$NR$^5$ or O(CH$_2$)$_{2-3}$NR$^5$(CH$_2$)$_{1-3}$, reacting a compound of general formula

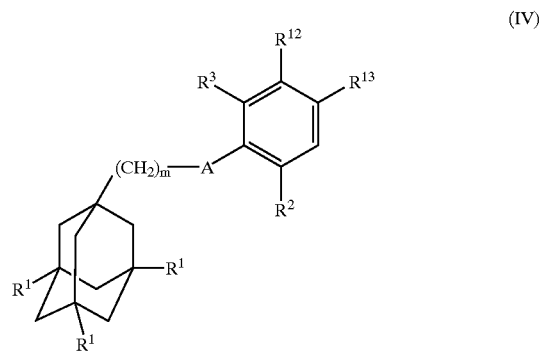

(IV)

wherein one of R$^{12}$ and R$^{13}$ represents a hydrogen atom and the other of R$^{12}$ and R$^{13}$ represents a hydroxyl group and m, A, R$^1$, R$^2$ and R$^3$ are as defined in formula (I), with a compound of general formula

R$^4$—Y—OH          (V)

wherein Y represents a bond or a group (CH$_2$)$_{1-6}$, O(CH$_2$)$_{2-6}$, (CH$_2$)$_{1-3}$O(CH$_2$)$_{2-3}$, NR$^5$(CH$_2$)$_{2-6}$ or (CH$_2$)$_{1-3}$NR$^5$(CH$_2$)$_{2-3}$ and R$^4$ is as defined in formula (I), in the presence of 1,1-(azodicarbonyl) dipiperidine and tributylphosphine (under conditions of the Mitsunobu reaction: Tetrahedron Lett. (1993), 34, 1639); or (iii) when X represents a bond, an oxygen atom or a group O(CH$_2$)$_{1-6}$, O(CH$_2$)$_{2-6}$O, O(CH$_2$)$_{2-3}$O(CH$_2$)$_{1-3}$, NR$^5$, NR$^5$(CH$_2$)$_{1-6}$, NR$^5$(CH$_2$)$_{2-6}$O or NR$^5$(CH$_2$)$_{2-3}$O(CH$_2$)$_{1-3}$ and A is NHC(O), reacting a compound of general formula

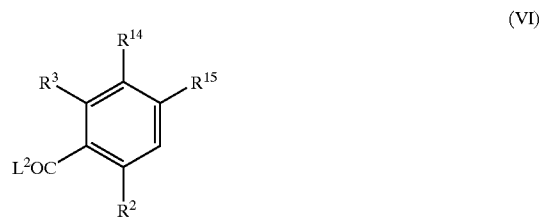

(VI)

wherein one of R$^{14}$ and R$^{15}$ represents a group —X'—R$^4$ and the other of R$^{14}$ and R$^{15}$ represents a hydrogen atom, X' represents a bond, an oxygen atom or a group O(CH$_2$)$_{1-6}$, O(CH$_2$)$_{2-6}$O, O(CH$_2$)$_{2-3}$O(CH$_2$)$_{1-3}$, NR$^5$, NR$^5$(CH$_2$)$_{1-6}$, NR$^5$(CH$_2$)$_{2-6}$O or NR$^5$(CH$_2$)$_{2-3}$O(CH$_2$)$_{1-3}$, L$^2$ represents a leaving group (e.g. a hydroxyl or chloride leaving group) and R$^2$, R$^3$, R$^4$ and R$^5$ are as defined in formula (I), with a compound of general formula

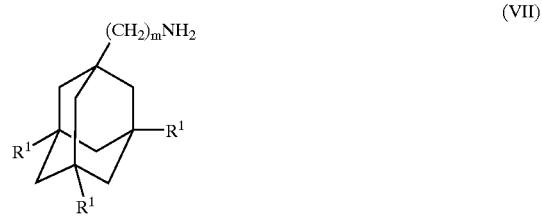

(VII)

wherein m and R$^1$ are as defined in formula (I), optionally in the presence of a coupling agent (e.g. 1,1'-carbonyldiimidazole); or (iv) when X represents a bond, an oxygen atom or a group O(CH$_2$)$_{1-6}$, O(CH$_2$)$_{2-6}$O, O(CH$_2$)$_{2-3}$O(CH$_2$)$_{1-3}$, NR$^5$, NR$^5$(CH$_2$)$_{1-6}$, NR$^5$(CH$_2$)$_{2-6}$O or NR$^5$(CH$_2$)$_{2-3}$O(CH$_2$)$_{1-3}$ and A is C(O)NH, reacting a compound of general formula

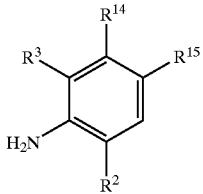

(VIII)

wherein R$^2$ and R$^3$ are as defined in formula (I) and R$^{14}$ and R$^{15}$ are as defined in formula (VI) in (iii) above, with a compound of general formula

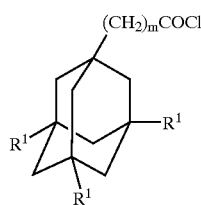

(IX)

wherein m and R$^1$ are as defined in formula (I), in the presence of a base (e.g. diisopropylamine); or (v) when X represents a bond or a group NR$^5$, NR$^5$(CH$_2$)$_{1-6}$, NR$^5$(CH$_2$)$_{2-6}$O or NR$^5$(CH$_2$)$_{2-3}$O(CH$_2$)$_{1-3}$, reacting a compound of general formula

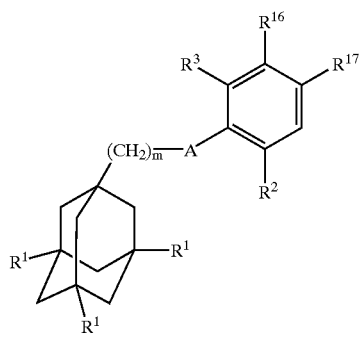

(X)

wherein one of R$^{16}$ and R$^{17}$ represents a leaving group, L$^3$, such as a halogen atom and the other of R$^{16}$ and R$^{17}$ represents a hydrogen atom and m, A, R$^1$, R$^2$ and R$^3$ are as defined in formula (I), with a compound of general formula

R$^4$—Z (XI)

wherein Z represents a hydrogen atom or a group NHR$^5$, (CH$_2$)$_{1-6}$NHR$^5$, O(CH$_2$)$_{2-6}$NHR$^5$ or a group (CH$_2$)$_{1-3}$O(CH$_2$)$_{2-3}$NHR$^5$ and R$^4$ and R$^5$ are as defined in formula (I), optionally in the presence of a palladium catalyst (e.g. palladium acetate), a phosphine ligand (e.g. BINAP) and a base (e.g. cesium carbonate); or (vi) when X represents a group CH$_2$O, reacting a compound of formula (II) as defined in (i) above with a compound of formula (V) as defined in (ii) above wherein Y represents a bond, in the presence of a base (e.g. sodium hydride) or in the presence of a metal salt (e.g. silver trifluoromethanesulfonate); or (vii) when X represents a group CH$_2$NR$^5$, reacting a compound of formula (II) as defined in (i) above with a compound of formula (XI) as defined in (v) above wherein Z represents a group NHR$^5$; or (viii) when X represents a group CH$_2$O(CH$_2$)$_{1-3}$ or CH$_2$O (CH$_2$)$_{2-3}$O, reacting a compound of formula (II) as defined in (i) above with a compound of formula (V) as defined in (ii) above wherein Y represents a group (CH$_2$)$_{1-3}$ or O(CH$_2$)$_{2-3}$, in the presence of a base (e.g. sodium hydride) or in the presence of a metal salt (e.g. silver trifluoromethanesulfonate); or (ix) when X represents a group CH$_2$NR$^5$CH$_2$ or CH$_2$NR$^5$ (CH$_2$)$_{2-3}$O reacting a compound of formula (II) as defined in (i) above with a compound of formula (XI) as defined in (v) above wherein Z represents a group CH$_2$NHR$^5$ or O(CH$_2$)$_{2-3}$NHR$^5$; or (x) when X represents a group CH$_2$ and R$^4$ represents an unsubstituted 4- to 6-membered saturated aliphatic heterocyclic ring system containing one nitrogen atom, reacting a compound of formula (II) as defined in (i) above, with a compound of general formula

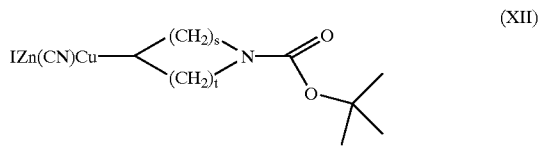

(XII)

wherein s and t independently represent 1 or 2; or (xi) when X represents a group CO, CONR$^5$, NR$^5$CO, SO$_2$, NR$^5$SO$_2$ or SO$_2$NR$^5$ and A is NHC(O), reacting a compound of general formula

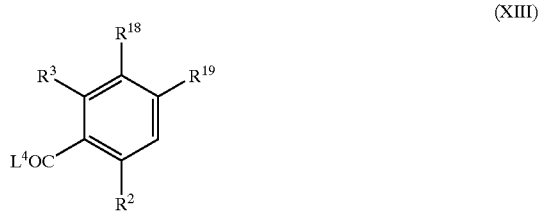

(XIII)

wherein one of R$^{18}$ and R$^{19}$ represents a group —X"—R$^4$ and the other of R$^{18}$ and R$^{19}$ represents a hydrogen atom, X" represents a group CO, CONR$^5$, NR$^5$CO, SO$_2$, NR$^5$SO$_2$ or SO$_2$NR$^5$, L$^4$ represents a leaving group (e.g. a hydroxyl or chloride leaving group) and R$^2$, R$^3$, R$^4$ and R$^5$ are as defined in formula (I), with a compound of formula (VI) as defined in (iii) above, optionally in the presence of a coupling agent (e.g. 1,1'-carbonyldiimidazole); or (xii) when X represents a group CO, CONR$^5$, NR$^5$CO, SO$_2$, NR$^5$SO$_2$ or SO$_2$NR$^5$ and A is C(O)NH, reacting a compound of general formula

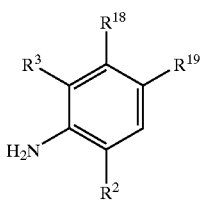

(XIV)

wherein $R^2$ and $R^3$ are as defined in formula (I) and $R^{18}$ and $R^{19}$ are as defined in formula (XII) in (xi) above, with a compound of formula (IX) as defined in (iv) above, in the presence of a base (e.g. diisopropylamine); or (xiii) when X represents a sulfur atom, reacting a compound of formula (X) as defined in (v) above, with an organolithium reagent such as n-butyllithium (e.g. at −70° C.) and then with a compound of general formula $$R^4\text{—}S\text{—}SO_2\text{—}Tol \quad (XV)$$

wherein Tol represents a tolyl group (4-methylphenyl) and $R^4$ is as defined in formula (I); or (xiv) when X represents a CHOH or $CH_2$ group, reacting a compound of formula (X) as defined in (v) above, with an organolithium reagent (e.g. methyllithium/t-butyllithium or n-butyllithium at −70° C.) and then with a compound of general formula $$R^4\text{—}CHO \quad (XVI)$$

wherein $R^4$ is as defined in formula (I), optionally followed by a reduction reaction, e.g. with methyloxalylchloride and triethylamine followed by tributyltin hydride in the presence of azobisisobutyronitrile; or (xv) when X represents a bond, reacting a compound of formula (X) as defined in (v) above, with an organolithium reagent such as n-butyllithium (e.g. at −70° C.) and then with a compound of general formula $$R^4\text{=}O \quad (XVII)$$

wherein $R^4$ is as defined in formula (I), optionally followed by a reduction reaction, e.g. with methyloxalylchloride and triethylamine followed by tributyltin hydride in the presence of azobisisobutyronitrile;

(xvi) when X represents a group SO, oxidising a corresponding compound of formula (I) in which X represents a sulphur atom (e.g. using, as oxidising agent, 3-chloroperoxybenzoic acid or potassium peroxymonosulphate (commercially sold under the trade mark "OXONE")); or to (xvii) when X represents a group $SCH_2$, reacting a compound of formula (X) as defined in (v) above, with an organolithium reagent (e.g. methyllithium and/or t-butyllithium at −70° C.) and then with a compound of general formula

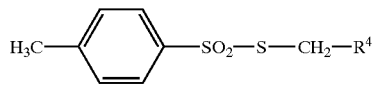

(XVIII)

wherein $R^4$ is as defined in formula (I); or (xviii) when X represents a group $SOCH_2$ or $SO_2CH_2$, oxidising a corresponding compound of formula (I) in which X represents a group $SCH_2$ (e.g. using, as oxidising agent, 3-chloroperoxybenzoic acid or potassium peroxymonosulphate (commercially sold under the trade mark "OXONE")); or (xix) when X represents a group CH=, reacting a compound of formula (II) as defined in (i) above with trimethyl phophite and then with a compound of formula (XVII) as defined in (xv) above in the presence of a base (e.g. lithium diisopropylamide); or (xx) when X represents a group $(CH_2)_{1-6}$, reacting a compound of general formula

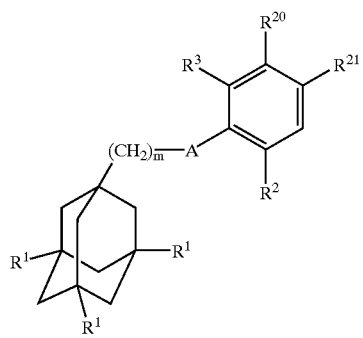

(XIX)

wherein one of $R^{20}$ and $R^{21}$ represents a group CHO or a group $(CH_2)_{1-5}CHO$ and the other of $R^{20}$ and $R^{21}$ represents a hydrogen atom, and m, A, $R^1$, $R^2$ and $R^3$ are as defined in formula (I), with a compound of general formula (XX), $R^4$—H, wherein $R^4$ is as defined in formula (I), in the presence of a reducing agent (e.g. sodium triacetoxyborohydride, in a suitable solvent such as dichloroethane); or (xxi) when X represents a group $(CH_2)_{1-6}NR^5$, $(CH_2)_{1-3}NR^5(CH_2)_{1-3}$ or $(CH_2)_{1-3}NR^5(CH_2)_{2-3}O$, reacting a compound of formula (XIX) as defined in (xx) above, with a compound of general formula (XXI), $R^4$—Z', wherein Z' represents a group $NHR^5$, $(CH_2)_{1-3}NHR^5$, $O(CH_2)_{2-3}NHR^5$ and $R^4$ and $R^5$ are as defined in formula (I), in the presence of a reducing agent (e.g. sodium triacetoxyborohydride, in a suitable solvent such as dichloroethane); or (xxii) when X represents a group $(CH_2)_{1-3}O(CH_2)_{1-3}$ or $(CH_2)_{1-3}O(CH_2)_{2-3}O$, reacting a compound of formula (XIX) as defined in (xx) above in which one of $R^{20}$ and $R^{21}$ represents a group CHO or a group $(CH_2)_{1-2}CHO$ and the other of $R^{20}$ and $R^{21}$ represents a hydrogen atom, with a reducing agent (such as sodium borohydride), followed by reaction with a compound of general formula (XXII), $R^4$—E, wherein E represents a group $(CH_2)_{1-3}L^5$ or $O(CH_2)_{2-3}L^5$, $L^5$ is a leaving group (such as a halogen atom or a sulphonate ester group, e.g. p-toluenesulphonate) and $R^4$ is as defined in formula (I), in the presence of a base (such as sodium hydride); or (xxiii) when X represents a group $(CH_2)_{1-6}$, reacting a compound of formula (II) as defined in (i) above with trimethylphosphite and then with a compound of formula (XVI) as defined in (xiv) above, a compound of formula (XVII) as defined in (xv) above or a compound of general formula (XVIA), $R^4(CH_2)_{1-4}CHO$ in which $R^4$ is as defined in formula (I), in the presence of a base (e.g. lithium diisopropylamide), followed by a reduction reaction (for example, with hydrogen and a platinum oxide catalyst); or (xxiv) when X represents a group $(CH_2)_{2-6}O$, reacting a compound of general formula

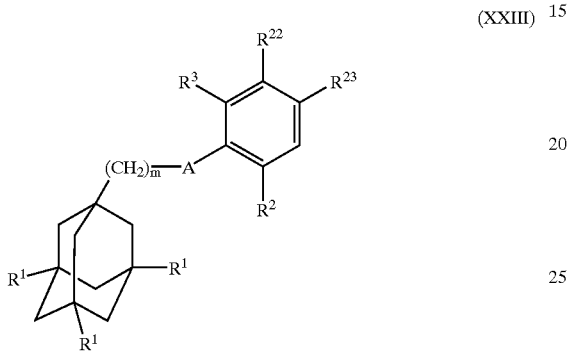

(XXIII)

wherein one of $R^{22}$ and $R^{23}$ represents a group $(CH_2)_{2-6}L^6$ and the other of $R^{20}$ and $R^{21}$ represents a hydrogen atom, $L^6$ represents a leaving group (e.g. a halogen atom or a sulphonate ester group such as p-toluenesulphonate) and m, A, $R^1$, $R^2$ and $R^3$ are as defined in formula (I), with a compound of formula (V) as defined in (ii) above in which Y represents a bond; or (xxv) when X represents a group CR'(OH) in which R' is a $C_1-C_6$ alkyl group, oxidising a corresponding compound of formula (I) in which X represents CH(OH) (e.g. using the oxidant dimethylsulphoxide/oxalyl chloride), followed by reaction with a $C_1-C_6$ alkyl-lithium reagent; or (xxvi) when X represents a group $CH_2S$, reacting a compound of formula (II) as defined in (i) above with a compound of general formula (XXIV), $R^4$—SH, wherein $R^4$ is as defined in formula (I), in the presence of a base (e.g. sodium hydride); or (xxvii) when X represents a group $CH_2SO$ or $CH_2SO_2$, oxidising a corresponding compound of formula (I) in which X represents a group $CH_2S$ (e.g. using, as oxidising agent, 3-chloroperoxybenzoic acid or potassium peroxymonosulphate (commercially sold under the trade mark "OXONE")); or (xxviii) when X represents a group $CH_2$ and $R^4$ represents a 3-piperidinyl or 2-piperazinyl group, reacting a compound of formula (II) as defined in (i) above with a reagent formed by combining pyridine or pyrazine with an aluminium hydride reagent (e.g. lithium aluminium hydride), followed by a reduction reaction (e.g. with hydrogen and a platinum catalyst); or (xxix) when X represents a group CH= and $R^4$ represents a 3-piperidinyl group, reacting a compound of general formula

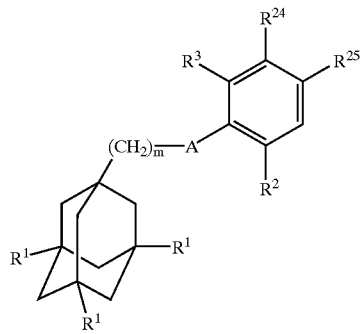

(XXV)

wherein one of $R^{24}$ and $R^{25}$ represents an aldehyde group —CHO, and the other of $R^{24}$ and $R^{25}$ represents a hydrogen atom and m, A, $R^1$, $R^2$ and $R^3$ are as defined in formula (I), with 2,3,4,5-tetrahydropyridine (Bull. Chem.Soc.Jpn. 1983, 56, 3199), followed by a reduction reaction (e.g. with sodium borohydride in a protic solvent such as methanol); or (xxx) when X represents a bond, $NR^5$ or $NR^5(CH_2)_{1-6}$ and $R^4$ represents a carbon-linked piperidyl or piperazinyl group, reducing a compound of general formula

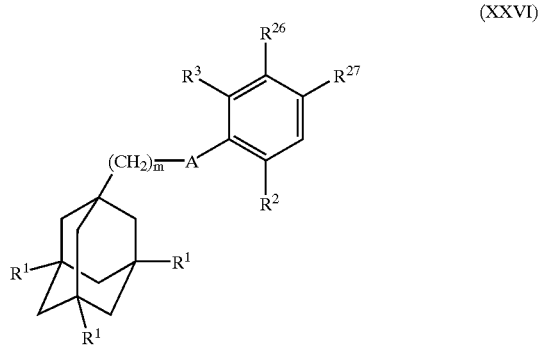

(XXVI)

wherein one of $R^{26}$ and $R^{27}$ represents a pyridyl, pyrazinyl, $NR^5$-pyridyl, $NR^5$-pyrazinyl, $NR^5(CH_2)_{1-6}$-pyridyl or $NR^5(CH_2)_{1-6}$-pyrazinyl group and the other of $R^{26}$ and $R^{27}$ represents a hydrogen atom, and m, A, $R^1$, $R^2$ and $R^3$ are as defined in formula (I), with a source of hydrogen and a hydrogenation catalyst (such as platinum oxide); or (xxxi) when X represents a group $CH_2O(CH_2)_{1-3}$ or $CH_2O(CH_2)_{2-3}O$ and A is NHC(O), reacting a compound of general formula

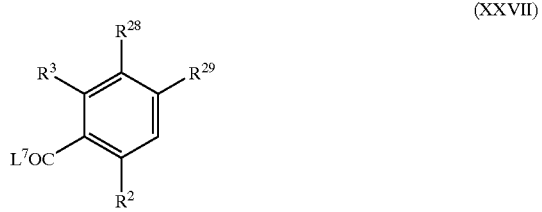

(XXVII)

wherein one of $R^{28}$ and $R^{29}$ represents a group —X'''—$R^4$ and the other of $R^{28}$ and $R^{29}$ represents a hydrogen atom, X''' represents a group $CH_2O(CH_2)_{1-3}$ or $CH_2O(CH_2)_{2-3}O$, is $L^7$ represents a leaving group (e.g. a hydroxyl or chloride leaving group) and $R^2$, $R^3$ and $R^4$ are as defined in formula (I), with a compound of formula (VII) as defined in (iii) above, optionally in the presence of a coupling agent (e.g. 1,1'-carbonyldiimidazole); or (xxxii) when X represents a group $CH_2O(CH_2)_{1-3}$ or $CH_2O(CH_2)_{2-3}O$ and A is C(O)NH, reacting a compound of general formula

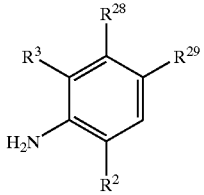
(XXVIII)

wherein $R^2$ and $R^3$ are as defined in formula (I) and $R^{28}$ and $R^{29}$ are as defined in formula (XXVII) in (xxxi) above, with a compound of formula (IX) as defined in (iv) above, in the presence of a base (e.g. diisopropylamine);

and optionally after (i), (ii), (iii), (iv), (v), (vi), (vii), (viii), (ix), (x), (xi), (xii), (xiii), (xiv), (xv), (xvi), (xvii), (xviii), (xix), (xx), (xxi), (xxii), (xxiii), (xxiv), (xxv), (xxvi), (xxvii), (xxviii), (xxix), (xxx), (xxxi) or (xxxii) converting the compound of formula (I) to a further compound of formula (I) and, if desired, forming a pharmaceutically acceptable salt or solvate of the compound of formula (I).

The processes of the invention may conveniently be carried out in a solvent, e.g. an organic solvent such as dichloromethane, dichloroethane, tetrahydrofuran, dioxane, xylene or dimethylformamide, at a temperature, e.g. in the range from 0 to 200° C., preferably in the range from 0 to 150° C.

Compounds of formula (II) in which A is NHC(O) may be prepared by reacting a compound of general formula

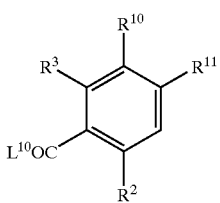
(XXX)

wherein $L^{10}$ represents a leaving group (e.g. a hydroxyl or chloride leaving group) and $R^2$ $R^3$, $R^{10}$ and $R^{11}$ are as defined in formula (II), with a compound of formula (VII) as defined above, optionally in the presence of a coupling agent (e.g. 1,1'-carbonyldiimidazole).

Compounds of formula (XXX) in which one of $R^{10}$ and $R^{11}$ represents a hydrogen atom and the other of $R^{10}$ and $R^{11}$ represents a group —$CH_2L^1$ and $L^1$ represents a bromine atom can be prepared by reacting a compound of general formula

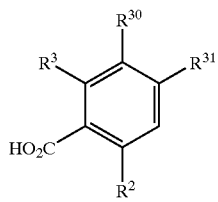
(XXXI)

wherein one of $R^{30}$ and $R^{31}$ represents a hydrogen atom and the other of $R^{30}$ and $R^{31}$ represents a methyl group and $R^2$ and $R^3$ are as defined in formula (I), with N-bromosuccinimide and catalytic azobisisobutyronitrile or dibenzoylperoxide, optionally followed by chlorination with oxalyl chloride and catalytic dimethylformamide or with thionyl chloride.

Compounds of formula (II) in which A is C(O)NH and $L^1$ represents, for example, a bromine atom may be prepared by reacting a compound of general formula

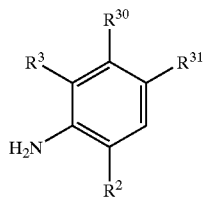
(XXXII)

wherein $R^2$ and $R^3$ are as defined in formula (I) and $R^{30}$ and $R^{31}$ are as defined in formula (XXXI) above, with a compound of formula (IX) as defined above, in the presence of a base (e.g. diisopropylethylamine), followed by reaction with N-bromosuccinimide and catalytic azobisisobutyronitrile or dibenzoylperoxide.

Compounds of formula (IV) in which A is NHC(O) may be prepared in an analogous manner to compounds of formula (II) in which A is NHC(O), using instead of the intermediate compound of formula (XXX), an intermediate compound of general formula

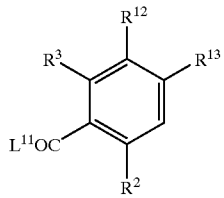
(XXXIII)

wherein $L^{11}$ represents a leaving group (e.g. a hydroxyl or chloride leaving group) and $R^2$, $R^3$, $R^{12}$ and $R^{13}$ are as defined in formula (IV).

Compounds of formula (IV) in which A is C(O)NH may be prepared by reacting a compound of general formula

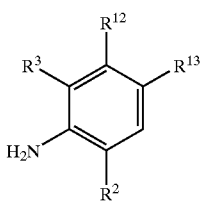
(XXXIV)

wherein $R^2$, $R^3$, $R^{12}$ and $R^{13}$ are as defined in formula (IV), with a compound of formula (IX) as defined above, optionally in the presence of a base (e.g. diisopropylethylamine).

Compounds of formula (VI) can be prepared by reacting a compound of general formula

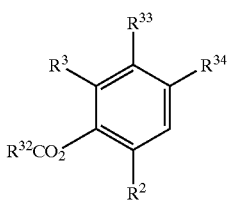
(XXXV)

wherein $R^{32}$ represents a hydrogen atom or a $C_1$–$C_6$ alkyl group, one of $R^{33}$ and $R^{34}$ represents a leaving group, $L^{12}$, such as a halogen atom (e.g. bromine or iodine) or a trifluoromethanesulfonate group and the other of $R^{33}$ and $R^{34}$ represents a hydrogen atom, and $R^2$ and $R^3$ are as defined in formula (VI), with a compound of general formula

H—X'—R⁴    (XXXVI)

wherein X' and $R^4$ are as defined in formula (VI), in the presence of a palladium catalyst (e.g. palladium acetate), a phosphine ligand (e.g. BINAP) and a base (e.g. cesium carbonate) (1996 *J. Am. Chem. Soc.*, 7215–6; 1997 *J. Am. Chem. Soc.*, 3395), followed by a hydrolysis reaction (e.g. with sodium hydroxide) and optionally a chlorination reaction (e.g. with oxalyl chloride and catalytic dimethylformamide or with thionyl chloride).

Compounds of formula (VII) may conveniently be prepared by reacting a compound of formula (VI) in which $L^2$ represents a hydroxyl group with diphenylphosphoryl azide in the presence of a base such as triethylamine.

Compounds of formula (X) in which A is NHC(O) may be prepared in an analogous manner to compounds of formula (II) in which A is NHC(O), using instead of the intermediate compound of formula (XXX), an intermediate compound of general formula

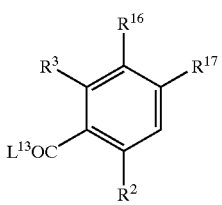
(XXXVII)

wherein $L^{13}$ represents a leaving group (e.g. a hydroxyl or chloride leaving group) and $R^2$, $R^3$, $R^{16}$ and $R^{17}$ are as defined in formula (X).

Compounds of formula (X) in which A is C(O)NH may be prepared in an analogous manner to compounds of formula (IV) in which A is C(O)NH, using instead of the intermediate compound of formula (XXXIV), an intermediate compound of general formula

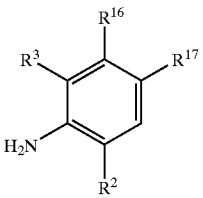
(XXXVIII)

wherein $R^2$, $R^3$, $R^{16}$ and $R^{17}$ are as defined in formula (X).

Compounds of formula (XII) can be prepared as described in Syn. Lett. (1998)379–380.

Compounds of formula (XIII) in which X" represents a group CO, CONR⁵, SO₂ or SO₂NR⁵ can be prepared by reacting a compound of general formula

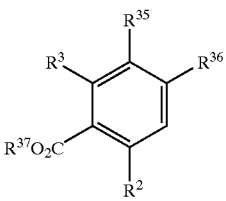
(XXXIX)

wherein one of $R^{35}$ and $R^{36}$ represents a group $COL^{14}$ or $SO_2L^{14}$ and the other of $R^{25}$ and $R^{26}$ represents a hydrogen atom, $L^{14}$ represents a leaving group (e.g. a halogen atom), $R^{37}$ represents a hydrogen atom or a $C_1$–$C_6$ alkyl group, and $R^2$ and $R^3$ are as defined in formula (XIII), with a compound of formula (XXXVI) in which X' represents a bond or a group NR⁵, in the presence of a base such as diisopropylethylamine and catalytic dimethylaminopyridine, followed by a hydrolysis reaction (e.g. sodium hydroxide) and, optionally, a chlorination reaction (e.g. with oxalyl chloride and catalytic dimethylformamide or with thionyl chloride).

Compounds of formula (XIII) in which X" represents a group represents a group NR⁵CO or NR⁵SO₂ can be prepared by reacting a compound of general formula

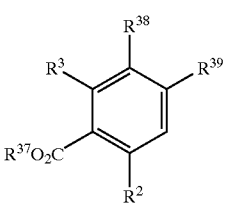
(XL)

wherein one of $R^{38}$ and $R^{39}$ represents a group NHR⁵ and the other of $R^{38}$ and $R^{39}$ represents a hydrogen atom, $R^{37}$ is as defined for compound (XXXIX), and $R^2$ and $R^3$ are as defined in formula (XIII), with a compound general formula (XLI), R⁴—J, wherein J represents a group COCl or SO₂Cl and $R^4$ is as defined in formula (I), in the presence of a base such as diisopropylethylamine.

Compounds of formula (XIV) may conveniently be prepared by reacting a compound of formula (XIII) in which $L^4$ represents a hydroxyl group with diphenylphosphoryl azide in the presence of a base such as triethylamine.

Compounds of formula (XIX) in which one of $R^{20}$ and $R^{21}$ represents a group $(CH_2)_{1-5}CHO$ and the other of $R^{20}$ and $R^{21}$ represents a hydrogen atom can be prepared by oxidising a compound of general formula

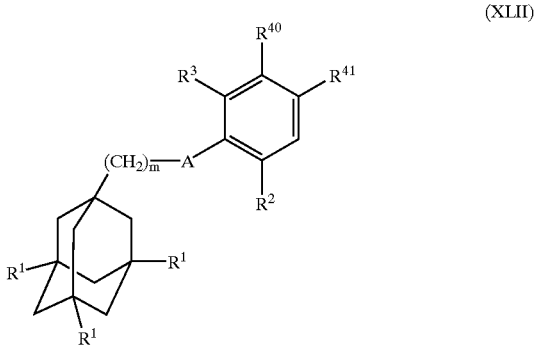

(XLII)

wherein one of $R^{40}$ and $R^{41}$ represents a group $(CH_2)_{2-6}OH$ and the other of $R^{40}$ and $R^{41}$ represents a hydrogen atom, and m, A, $R^1$, $R^2$ and $R^3$ are as defined in formula (I), using as the oxidising agent, for example, Dess Martin Periodinane reagent.

Compounds of formula (XLII) in which one of $R^{40}$ and $R^{41}$ represents a group $(CH_2)_2OH$ and the other of $R^{40}$ and $R^{41}$ represents a hydrogen atom can be prepared from a compound of general formula (X) as defined above, an organolithium reagent such as methyllithium (at −70° C.) followed by n-butyllithium (at −70° C.), and then treatment with ethylene oxide.

Compounds of formula (XLII) in which one of $R^{40}$ and $R^{41}$ represents a group $(CH_2)_{3-6}OH$ and the other of $R^{40}$ and $R^{41}$ represents a hydrogen atom can be prepared by reacting a compound of general formula (X) as defined above with a compound of general formula

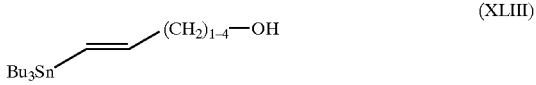

(XLIII)

in the presence of a palladium catalyst such as tetrakis(triphenylphosphine)palladium(0), followed by reduction with, for example, hydrogen and a platinum oxide catalyst.

Compounds of formula (XIX) in which one of $R^{20}$ and $R^{21}$ represents a group CHO and the other of $R^{20}$ and $R^{21}$ represents a hydrogen atom (which are equivalent to compounds of formula (XXV)) can be prepared from a compound of general formula (X) as defined above, with an organolithium reagent such as methyllithium (at −70° C.) followed by n-butyllithium (at −70° C.) and then with dimethylformamide.

Compounds of formula (XXIII) in which $L^6$ represents an iodine atom or p-toluenesulphonyloxy group may be prepared by reacting a compound of formula (XLII) as defined above with iodine/triphenylphosphine/imidazole or with a sulphonyl chloride such as p-toluenesulphonyl chloride, in the presence of a base such as diisopropylethylamine.

Compounds of formula (XXVI) in which one of $R^{26}$ and $R^{27}$ represents a pyridyl or pyrazinyl group and the other of $R^{26}$ and $R^{27}$ represents a hydrogen atom can be prepared from a compound of formula (X) as defined above by reaction with a pyridyl or pyrazinyl boronic acid in the presence of a palladium catalyst such as tetrakis(triphenylphosphine)palladium(0).

Compounds of formula (XXVI) in which one of $R^{26}$ and $R^{27}$ represents a $NR^5$-pyridyl, $NR^5$-pyrazinyl, $NR^5(CH_2)_{1-6}$-pyridyl or $NR^5(CH_2)_{1-6}$-pyrazinyl group and the other of $R^{26}$ and $R^{27}$ represents a hydrogen atom can be prepared from a compound of formula (X) as defined above by reaction with a compound $NHR^5$pyridyl, $NHR^5$pyrazinyl, $NHR^5(CH_2)_{1-6}$-pyridyl or $NHR^5(CH_2)_{1-6}$-pyrazinyl, in the presence of a palladium catalyst (e.g. palladium acetate), a phosphine ligand (e.g. BINAP) and a base (e.g. cesium carbonate).

Compounds of formulae (III), (V), (VII), (IX), (XI), (XV), (XVI), (XVIA), (XVII), (XVII), (XX), (XXI), (XXII), (XXIV), (XXVII), (XXVIII), (XXXI), (XXXII), (XXXIII), (XXXIV), (XXXV), (XXXVI), (XXXVII), (XXXVIII), (XXXIX), (XL), (XLI), (XLII) and (XLIII) are either commercially available, are well known in the literature or may be prepared easily using known techniques.

Compounds of formula (I) can be converted into further compounds of formula (I) using standard procedures. For example, compounds of formula (I) in which one of $R^2$ and $R^3$ represents a nitro group can be converted to compounds of formula (I) in which one of $R^2$ and $R^3$ represents an amino group by reduction using iron powder and ammonium chloride in ethanol/water under reflux conditions. The latter compounds can in turn be converted into compounds of formula (I) in which one of $R^2$ and $R^3$ represents a halogen atom, e.g. chlorine, by diazotization (e.g. with sodium nitrite) and reaction with copper chloride. Compounds of formula (I) in which $R^6$ or $R^7$ represents a hydrogen atom can be converted to compounds of formula (I) in which $R^6$ or $R^7$ represents a $C_1$–$C_6$ alkyl, $C_2$–$C_6$ hydroxyalkyl, $C_3$–$C_8$ cycloalkyl or a 3- to 8-membered saturated heterocyclic ring by standard chemical procedures.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity. They are therefore indicated as pharmaceuticals for use in the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, burn injury, ischaemic heart disease, stroke and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples.

EXAMPLE 1

2-Nitro-3-piperazin-1-yl-N-(tricyclo[3.3.1.1$^{3,7}$]dec-1-ylmethyl)-benzamide

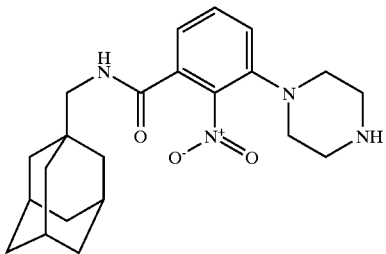

a) 3-Chloro-2-nitro-N-(tricyclo[3.3.1.1$^{3,7}$]dec-1-ylmethyl)-benzamide

To a suspension of 3-chloro-2-nitrobenzoic acid (2.68 g) in dichloromethane (10 ml) at 0° C. was added oxalyl chloride (3 ml) and dimethylformamide (1 drop). The resulting mixture was stirred at room temperature under a nitrogen atmosphere for 1 hour, then concentrated under reduced pressure to yield a solid. The solid was dissolved in dichloromethane (10 ml) and cooled to 0° C. A solution of 1-adamantanemethylamine (2.19 g) and N,N-diisopropylethylamine (11 ml) in dichloromethane (10 ml) was added portion-wise and the resulting solution allowed to stir at room temperature under a nitrogen atmosphere for 2 h. The reaction mixture was poured into water and the organic phase separated and washed with 2N hydrochloric acid, 10% aqueous sodium hydroxide and saturated brine. The organic phase was then dried over sodium sulfate, filtered and concentrated under reduced pressure and the resulting solid recrystallized from iso-propanol to afford the subtitle compound as a solid (3.52 g).

MS (APCI+ve) 349 (M+H)$^+$ $^1$H NMR (DMSO-d$_6$) δ 8.74 (1H, t); 7.89 (1H, m); 7.75–7.69 (2H, m); 2.91 (2H, d), 1.93 (3H, bs); 1.64 (6H, dd); 1.47 (6H, d)

b) 3-(4-{1,1-dimethylethyl}oxycarbonyl]-piperazin-1-yl)-2-nitro-N-(tricyclo[3.3.1.1$^{3,7}$]dec-1-ylmethyl)-benzamide A mixture of 3-chloro-2-nitro-N-(tricyclo[3.3.1.1$^{3,7}$]dec-1-ylmethyl)-benzamide (2.80 g, Example 1a) and piperazine-1-carboxylic acid, tert-butyl ester (7.47 g) in dry dimethyl sulfoxide (10 ml) was heated at 120° C. under a nitrogen atmosphere for 24 h. The cooled reaction mixture was diluted with water and extracted thrice with ethyl acetate. The combined extracts were washed with water, dried over sodium sulfate, filtered, and the filtrate concentrated under reduced pressure to give a solid. Purification by chromatography over silica gel, eluting with iso-hexane/ethyl acetate (2:1) gave the subtitle compound as a solid (3.8 g).

MS (APCI+ve) 499 (M+H)$^+$ $^1$H NMR (DMSO-d$_6$) δ 8.55 (1H, t); 7.62–7.59 (2H, m); 7.43 (1H, dd); 3.38 (4H, bt); 2.90–2.84 (6H, m), 1.93 (3H, bs); 1.63 (6H, dd); 1.47 (6H, d); 1.41 (9H, s)

c) 2-Nitro-3-piperazin-1-yl-N-(tricyclo[3.3.1.1$^{3,7}$] dec-1-ylmethyl)-benzamide A solution of 3-(4-{1,1-dimethylethyl}oxycarbonyl]-piperazin-1-yl)-2-nitro-N-(tricyclo[3.3.1.1$^{3,7}$]-dec-1- ylmethyl)-benzamide (0.58 g, Example 1b) and hydrochloric acid (6.4 ml, 4N in dioxane) in tetrahydrofuran (20 ml) was stirred at room temperature under a nitrogen atmosphere for 18 h. The reaction mixture was concentrated under reduced pressure and the residue dissolved in water, made basic with solid sodium bicarbonate and extracted with dichloromethane three times. The combined organic extracts were dried over magnesium sulfate, filtered and the filtrate concentrated under reduce pressure to give a solid. Purification by chromatography over silica gel, eluting with 10% methanol in dichloromethane afforded the title compound as a solid (0.165 g).

MS (APCI+ve) 399 (M+H)+

$^1$H NMR (DMSO-d$_6$) δ 8.52 (1H, t); 7.59 (1H, t); 7.51 (1H d); 7.35 (1H, d); 2.88 (2H, d); 2.81 (4H, m); 2.37 (4H, m); 1.93 (3H, bs); 1.67 (3H, d); 1.60 (3H, d); 1.47 (6H, s)

EXAMPLE 2

2-Amino-3-piperazin-1-yl-N-(tricyclo[3.3.1.1$^{3,7}$]dec-1-ylmethyl)-benzamide, dihydrochloride salt

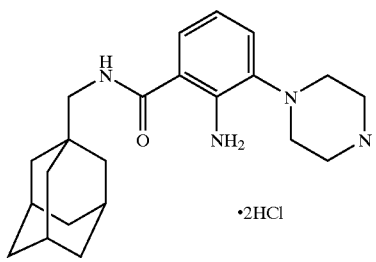

a) 2-Amino-3-(4-{1,1-dimethylethyl}oxycarbonyl]-piperazin-1-yl)-N-(tricyclo[3.3.1.1$^{3,7}$]dec-1-ylmethyl)-benzamide A suspension of 3-(4-{1,1-dimethylethyl}oxycarbonyl]-piperazin-1-yl)-2-nitro-N-(tricyclo[3.3.1.1$^{3,7}$]dec-1-ylmethyl)-benzamide (3.8 g, Example 1b), iron powder (2.13 g) and ammonium chloride (2.04 g) in 2:1 ethanol/water (90 ml) was heated at reflux, under a nitrogen atmosphere, for 2 h. The cooled reaction mixture was filtered and the filtrate partitioned between water and ethyl acetate. The organic layer was separated and washed with water twice further, dried over magnesium sulfate, filtered and the filtrate concentrated under reduced pressure to give a residue. Purification of the residue by chromatography over silica gel, eluting with 20% ethyl acetate in iso-hexane, yielded the subtitle compound as a solid (2.27 g).

MS (APCI+ve) 469 (M+H)+ b) 2-Amino-3-piperazin-1-yl-N-(tricyclo[3.3.1.1$^{3,7}$]dec-1-ylmethyl)-benzamide, dihydrochloride salt Prepared as described in Example 1c) using 2-amino-3-(4-{1,1-dimethyl ethyl}oxycarbonyl]-piperazin-1-yl)-N-(tricyclo[3.3.1.1$^{3,7}$]dec-1-ylmethyl)-benzamide (0.2 g, Example 2a) and hydrochloric acid (5 ml, 4N in dioxane). The reaction mixture was concentrated under reduced pressure to give a solid which when triturated with diethyl ether gave the title compound as a solid (0.2 g).

MS (APCI+ve) 369 (M−2HCl)+

$^1$H NMR (DMSO-d$_6$) δ 9.16 (2H, bs); 8.14 (1H, t); 7.37 (1H, d); 7.07 (1H, d); 6.64 (1H, t); 3.27 (4H, bs); 2.98 (4H, bs); 2.95 (2H, d); 1.93 (3H, bs); 1.67 (3H, d); 1.59 (3H, d); 1.48 (6H, s).

EXAMPLE 3

2-Chloro-3-piperazin-1-yl-N-(tricyclo[3.3.1.1$^{3,7}$]dec-1-ylmethyl)-benzamide

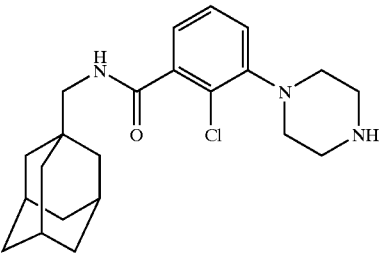

a) 2-Chloro-3-(4-{1,1-dimethylethyl}oxycarbonyl]-piperazin-1-yl)N-(tricyclo[3.3.1.1$^{3,7}$]dec-1-ylmethyl)-benzamide To a solution of 2-amino-3-(4-{1,1-dimethylethyl}oxycarbonyl]-piperazin-1-yl)-N-(tricyclo[3.3.1.1$^{3,7}$]dec-1-ylmethyl)-benzamide (1 g, Example 2a) in tetrahydrofuran (23 ml) was added 1M aqueous hydrochloric acid (2.78 ml) and water (10 ml). The solution was cooled to 0° C. and sodium nitrite (1.91 g) added portion-wise, whilst maintaining the internal temperature below 5° C. After stirring at 0–5° C. for 0.5 h, a pre-cooled suspension of copper (I) chloride (10.58 g) and copper (II) chloride in water (20 ml) was added portion-wise to the pale yellow suspension. The mixture was stirred at 0° C. for 0.5 h then at room temperature for 0.5 h. The reaction mixture was poured into a mixture of water and dichloromethane and 1/1:0.88 ammonia/water was added until the aqueous phase was homogeneous. The layers were separated and the aqueous phase extracted twice further with dichloromethane. The combined organic extracts were washed with 1/1:0.88 ammonia/water until the aqueous layer was colourless, dried over sodium sulfate, filtered and concentrated under reduced pressure to yield an oil. Purification by chromatography on silica gel, eluting with 20–35% ethyl acetate/iso-hexane gave the subtitle compound as a solid (0.45 g).

MS (APCI+ve) 388 (M−BOC)+

$^1$H NMR (DMSO-d$_6$) δ 8.27 (1H, t); 7.32 (1H, t); 7.19 (1H, d); 7.04 (1H, d); 3.48 (4H, m); 2.93–2.91 (6H, m); 1.94 (3H, bs); 1.64 (3H, d); 1.59 (3H, d); 1.52 (6H, s); 1.43 (9H, s).

b) 2-Chloro-3-piperazin-1-yl-N-(tricyclo[3.3.1.1$^{3,7}$dec-1-ylmethyl)-benzamide To a solution of 2-Chloro-3-(4-{1,1-dimethylethyl}oxycarbonyl]-piperazin-1-yl)-N-(tricyclo[3.3.1.1$^{3,7}$]dec-1-ylmethyl)-benzamide (0.45 g, Example 3a) in dichloromethane (10 ml) was added trifluoroacetic acid (5 ml). After stirring at room temperature under a nitrogen atmosphere the reaction mixture was concentrated under reduced pressure to give a gum. The gum was partitioned between water and dichloromethane and made basic with solid sodium bicarbonate. The layers were separated and the aqueous layer extracted twice further with dichloromethane. The combined organic extracts were washed twice with water, saturated brine then dried over magnesium sulfate, filtered and the filtrate concentrated under reduced pressure to give a foam. The foam was purified by normal phase HPLC (0–20% ethanol/dichloromethane) and chromatography over silica gel, eluting 10% methanol in dichloromethane, to afford the title compound as a foam (0.05 g).

MS (APCI+ve) 388/90 (M+H)+

$^1$H NMR (DMSO-$d_6$) δ 8.24 (1H, t); 7.31 (1H, t); 7.15 (1H, d); 7.00 (1H, d); 2.96–2.87 (10H, m); 1.93 (3H, bs); 1.67 (3H, d); 1.59 (3H, d); 1.52 (6H, s).

EXAMPLE 4

2-Chloro-5-piperazin-1-yl-N-(tricyclo[3.3.1.1$^{3,7}$]dec-1-ylmethyl)-benzamide

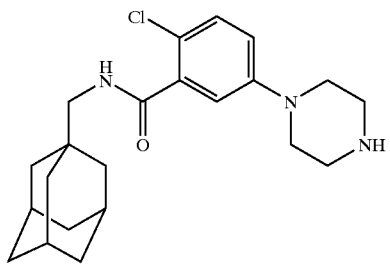

a) 2-Chloro-5-nitro-N-(tricyclo[3.3.1.1$^{3,7}$]dec-1-ylmethyl)-benzamide

To a solution of 2-chloro-5-nitrobenzoic acid (1.22 g) in N,N-dimethylformamide (1.5 ml) was added carbonyldiimidazole (1.0 g). The resulting reaction mixture was stirred for 2.5 h and then 1-adamantanemethylamine (1.0 g) was added. After 14 h the reaction mixture was partitioned between ethyl acetate and water and the organic layer was separated, washed with water and brine and then dried over sodium sulphate (Na$_2$SO$_4$). The organic layer was concentrated under reduced pressure to give a residue which was purified by silica gel chromatography (eluting with 3–10% methanol in dichloromethane) to yield the subtitle compound as a yellow solid (1.7 g).

MS (APCI+ve) 348/350 (M+H)+

$^1$H NMR (CDCl$_3$) δ 8.53 (1H, d), 8.2 (1H, dd), 7.6 (1H, d), 6.2 (1H, bs), 3.2 (2H, d), 2.0 (3H,bs), 1.8 (12H, m)

b) 5-Amino-2-chloro-N-(tricyclo[3.3.1.1$^{3,7}$]dec-1-ylmethyl)-benzamide

A solution of the nitro compound from Example 4a, (0.50 g) and ammonium chloride (0.5 g) were dissolved in 50% aqueous ethanol. Iron powder (0.5 g) was added and the mixture stirred at reflux temperature for 3 hr before being cooled and solids removed by filtration. The mother liquors were treated with 10% sodium hydroxide solution and the product extracted into ethyl acetate. The organic solution was washed with brine, dried over sodium sulphate (Na$_2$SO$_4$) and concentrated to give a residue which was purified by silica gel chromatography to give the title compound as a white solid (0.4 g).

MS (APCI+ve) 319/21 (M+H)+

$^1$H NMR (DMSO-$d_6$) δ 8.14 (1H, t); 7.03 (1H, dd); 6.56 (2H, m); 5.36 (2H, s); 2.89 (2H, d); 1.95 (3H, s); 1.7 (12H, m)

c) 2-Chloro-5-Piperazin-1-yl-N-(tricyclo[3.3.1.1$^{3,7}$]dec-1-ylmethyl)-benzamide To a solution of 5-amino-2-chloro-N-(tricyclo[3.3.1.1$^{3,7}$]dec-1-ylmethyl)-benzamide (1.00 g, Example 4b) in xylene (20 ml) was added bis-(2-chloroethyl)amine hydrochloride salt (0.620 g). The mixture was heated at 150° C. for 12 h (a dark solution is obtained). The cold solution was washed with 2M HCl, the aqueous layer washed with ethyl acetate then basified with sodium bicarbonate and extracted twice with dichloromethane. The organic layer was dried over magnesium sulfate, filtered and the filtrate concentrated under reduced pressure to give a foam. The crude material was purified on silica gel (0–10% ethanol/dichloromethane), to afford the title compound as a white solid (0.90 g).

MS (APCI+ve) 388/90 (M+H)+

$^1$H NMR (DMSO-$d_6$) δ 8.22 (1H, t); 7.22 (1H, d); 6.96 (1H, dd); 6.84 (1H, d); 3.50–3.20 (7H, m); 3.00–2.90 (2H, t); 2.91 (2H, d); 1.94 (3H, bs); 1.67 (3H, d); 1.59 (3H, d); 1.52 (6H, s).

EXAMPLE 5

2-Chloro-5-(hexahydro-1H-1,4-diazepin-1-yl)-N-(tricyclo[3.3.1.1$^{3,7}$]dec-1-ylmethyl)-benzamide, hydrochloride salt

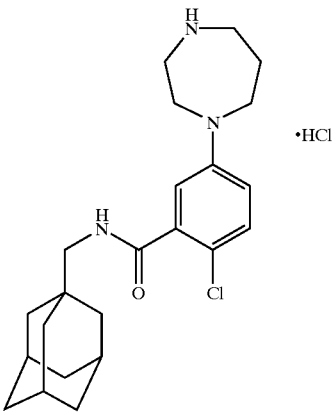

a) 4-[4-Chloro-3-(ethoxycarbonyl)phenyl] hexahydro-1H-1,4-diazepine-1-carboxylic acid, 1,1-dimethylethyl ester A mixture of 5-bromo-2-chloro-benzoic acid, ethyl ester (0.50 g), hexahydro-1H-1,4-diazepine-1-carboxylic acid, 1,1-dimethylethyl ester (0.46 g), cesium carbonate (0.86 g), palladium (II) acetate (8.5 mg) and (R)-BINAP (35 mg) in toluene (3 ml) was heated at 100° C. for 14 h in a pressure vessel flushed with nitrogen. The cooled reaction mixture was poured into water and extracted (3 times) with ethyl acetate. The combined organic extracts were washed with saturated sodium chloride solution and then dried over magnesium sulfate. Evaporation under reduced pressure gave an oil which was purified by chromatography over silica gel, eluting with 20% ethyl acetate in iso-hexane to yield the subtitle compound as an oil (0.21 g).

MS (APCI+ve) 282/284 (M–BOC)+ b) 4-(3-Carboxy-4-chlorophenyl)hexahydro-1H-1,4-diazepine-1-carboxylic acid, 1,1-dimethylethyl ester A suspension of 4-[4-chloro-3-(ethoxycarbonyl)phenyl] hexahydro-1H-1,4-diazepine-1-carboxylic acid, 1,1-dimethylethyl ester (Example 5a, 0.21 g), lithium hydroxide monohydrate (1.05 ml of 3M solution in water) in 1:1 ethanol/water (7 ml) was stirred at room temperature for 14 h. More lithium hydroxide monohydrate (0.55 ml of 3M solution in water) was added followed by tetrahydrofuran (1 ml). The resulting solution was stirred for 4 h at room temperature then poured into water and extracted with diethyl ether. The aqueous phase was separated, acidified with 2M hydrochloric acid and then extracted with dichloromethane three times. The combined dichloromethane layers were dried over magnesium sulfate and evaporated under reduced pressure to yield the subtitle compound as a glass.

MS (APCI+ve) 298/300 (M−$^t$Bu)$^+$ c) Hexahydro4-[4-methyl-3-[[(tricyclo[3.3.1.1$^{3,7}$]dec-1-ylmethyl)amino]carbonyl]-phenyl]1H-1,4-diazepine-1-carboxylic acid, 1,1-dimethylethyl ester A solution of 4-(3-carboxy-4-chlorophenyl)hexahydro-1H-1,4-diazepine-1-carboxylic acid, 1,1-dimethylethyl ester (Example 5b, 0.10 g) and N,N'-carbonyldiimidazole (0.045 g) in dimethylformamide (3 ml) was stirred at room temperature for 2 h. 1-Adamantanemethylamine (0.050 ml) was then added and stirring continued for 14 h. The reaction mixture was poured into water and extracted with ethyl acetate three times. The ethyl acetate layers were combined and washed with 2M hydrochloric acid, 10% aqueous sodium hydroxide and brine, then dried over magnesium sulfate and concentrated under reduced pressure. Purification by chromatography on silica gel, eluting with 20–30% ethyl acetate in iso-hexane, gave the subtitle product as a gum which crystallised on standing.

MS (APCI+ve) 502/504 (M+H)$^+$ d) 2-Chloro-5-(hexahydro-1H-1,4-diazepin-1-yl)-N-(tricyclo[3.3.1.1$^{3,7}$]dec-1-ylmethyl)-benzamide, hydrochloride salt Hexahydro-4-[4-methyl-3-[[(tricyclo[3.3.1.1$^{3,7}$]dec-1-ylmethyl)amino]carbonyl]-phenyl]-1H-1,4-diazepine-1-carboxylic acid, 1,1-dimethylethyl ester (from Example 5c) was dissolved in methanol (5 ml) and hydrochloric acid (0.5 ml of a 4N solution in dioxane) was added. After stirring at room temperature for 14 h, the mixture was evaporated to ⅔ original volume under reduced pressure. Diethyl ether was gradually added to the solution and the resulting precipitate collected by filtration, washed with diethyl ether and dried in vacuo to afford the title compound as a solid (0.027 g)

MS (APCI+ve) 402/404 (M+H)+

$^1$H NMR (DMSO-d$_6$) δ 9.11 (2H, bs); 8.18 (1H,t); 7.24 (1H, d); 6.81 (1H, dd); 6.71 (1H, d); 3.71 (2H, t); 3.50 (2H,t); 3.19 (2H, bs); 2.93 (2H, bs); 2.92 (2H, d); 2.08 (2H, m); 1.94 (3H, bs); 1.67 (3H, d); 1.59 (3H, bs); 1.52 (6H, s)

EXAMPLE 6

5-(4-Amino-1-piperidinyl)-2-chloro-N-(tricyclo[3.3.1.1$^{3,7}$]dec-1-ylmethyl)-benzamide, hydrochloride salt

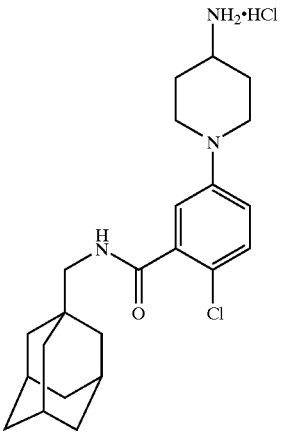

a) 2-Chloro-5-[4-[[(1,1-dimethylethoxy)carbonyl]amino])-1-piperidinyl]-benzoic acid, ethyl ester Prepared as described in Example 5a) using 5-bromo-2-chloro-benzoic acid, ethyl ester (0.50 g), 4-piperidinyl-carbamic acid, 1,1-dimethylethyl ester (0.46 g), cesium carbonate (0.86 g), palladium (II) acetate (8.5 mg) and (R)-BINAP (35 mg) and toluene (3 ml) to afford the subtitle compound as an oil (0.17 g).

MS (APCI+ve) 383/385 (M+H)$^+$ b) 2-Chloro-5-[4-[[(1,1-dimethylethoxy)carbonyl]amino]-1-piperidinyl]-benzoic acid Prepared as described in example 5b) using 2-chloro-5-[4-[[(1,1-dimethylethoxy)-carbonyl]amino]-1-piperidinyl]-benzoic acid, ethyl ester (Example 6a, 0.17 g), lithium hydroxide monohydrate (0.88 ml of a 3M solution in water), 1:1 ethanol/water (7 ml) and tetrahydrofuran (1 ml) to give the subtitle compound as a solid (0.14 g).

MS (APCI+ve) 354/356 (M+H)$^+$ c) [1-[4-Chloro-3-[[(tricyclo[3.3.1.1$^{3,7}$]dec-1-ylmethyl)amino]carbonyl]phenyl]-4-piperidinyl]-carbamic acid, 1,1-dimethylethyl ester Prepared as described in Example 5c) using 2-chloro-5-[4-[[(1,1-dimethylethoxy)carbonyl]amino]-1-piperidinyl]-benzoic acid (Example 6b, 0.065 g), N,N'-carbonyldiimidazole (0.030 g), 1-adamantanemethylamine (0.032 ml) and dimethylformamide (3 ml) to give the subtitle compound as a solid.

MS (APCI+ve) 501/503 (M+H)$^+$ d) 5-(4-Amino-1-piperidinyl)-2-chloro-N-(tricyclo[3.3.1.1$^{3,7}$]dec-1-ylmethyl)-benzamide, hydrochloride salt Prepared as described in example 5d) above using [1-[4-chloro-3-[[(tricyclo[3.3.1.1$^{3,7}$]dec-1-ylmethyl)amino]carbonyl]phenyl]-4-piperidinyl]-carbamic acid, 1,1-dimethylethyl ester (Example 6c), hydrochloric acid (0.5 ml of a 4N solution in dioxane) and methanol (10 ml). The mixture was heated at reflux for 15 min. to complete the reaction. After evaporation to two-thirds of the original volume, a solid crystallised on standing which was collected by filtration and dried in vacuo to give the title compound as a solid (0.025 g).

MS (APCI+ve) 402/404 (M−HCl)+

¹H NMR (DMSO-d₆) δ 8.23 (1H, t); 8.11 (1H,bs); 7.28 (1H, d); 7.03 (1H, dd); 6.94 (1H, s); 3.74 (2H, d); 3.20 (1H, m); 2.91 (2H, d); 2.83 (2H, t); 1.98 (2H, bs); 1.69–1.58 (8H, m); 1.52 (6H, s)

EXAMPLE 7

(+/−)-5-(3-Amino-1-pyrrolidinyl)-2-chloro-N-(tricyclo[3.3.1.1³,⁷]dec-1-ylmethyl)-benzamide, hydrochloride salt

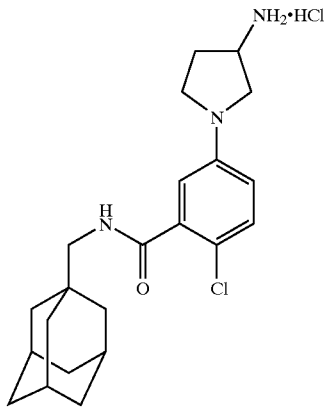

a) (+/−)-2-Chloro-5-[3-[[(1,1-dimethylethoxy)carbonyl]amino]-1-pyrrolidinyl]-benzoic acid, ethyl ester Prepared as described in Example 5a) using 5-bromo-2-chloro-benzoic acid, ethyl ester (0.50 g), 3-pyrrolidinyl-carbamic acid 1,1-dimethylethyl ester (0.42 g), cesium carbonate (0.86 g), palladium (II) acetate (21 mg) and (R)-BINAP (88 mg) and toluene (3 ml) to afford the subtitle compound as an oil (0.25 g).

MS (APCI+ve) 311/313 (M−BOC)+ b) (+/−)-2-Chloro-5-[3-[[(1,1-dimethylethoxy)carbonyl]amino]-1-pyrrolidinyl]-benzoic acid Prepared as described in Example 5b) using (+/−)-2-chloro-5-[3-[[(1,1-dimethylethoxy)carbonyl]amino]-1-pyrrolidinyl]-benzoic acid, ethyl ester (Example 7a, 0.25 g), lithium hydroxide monohydrate (1.36 ml of a 3M solution in water), 1:1 ethanol/water (7 ml) and tetrahydrofuran (1 ml) to give the subtitle compound as a solid (0.23 g).

MS (APCI+ve) 284/286 (M−BOC)+ c) (+/−)-[1-[4-chloro-3-[[(tricyclo[3.3.1.13,7]dec-1-ylmethyl)amino]carbonyl]phenyl]-3-pyrrolidinyl]-carbamic acid, 1,1-dimethylethyl ester Prepared as described in Example 5c) using (+/−)-2-chloro-5-[3-[[(1,1-dimethylethoxy)carbonyl]amino]-1-pyrrolidinyl]-benzoic acid (Example 7b, 0.070 g), N,N'-carbonyldiimidazole (0.033 g), 1-adamantanemethylamine (0.036 ml) and dimethylformamide (3 ml) to give the subtitle compound as a gum.

MS (APCI+ve) 487/489 (M+H)+ d) (+/−)-5-(3-Amino-1-pyrrolidinyl)-2-chloro-N-(tricyclo[3.3.1.1³,⁷]dec-1-ylmethyl)-benzamide, hydrochloride salt Prepared as described in example 5d) above using (+/−)-[1-[4-chloro-3-[[(tricyclo[3.3.1.1³,⁷]dec-1-ylmethyl)amino]carbonyl]phenyl]-3-pyrrolidinyl]-carbamic acid, 1,1-dimethylethyl ester (Example 7c), hydrochloric acid (0.5 ml of a 4N solution in dioxane) and methanol (5 ml). Evaporation under reduced pressure gave a solid on trirtuation with diethyl ether. Recrystallisation from methanol/diethyl ether gave the title compound as a solid (0.030 g).

MS (APCI+ve) 388/390 (M+H)+

¹H NMR (DMSO-d₆) δ 8.24 (3H, bs); 8.20 (1H, t); 7.25 (1H, d); 6.61 (1H, dd); 6.51 (1H, d); 3.94 (1H, m); 3.55–3.32 (2H, m); 3.29 (2H, m); 2.92 (2H, d); 2.37–2.27 (1H, m); 2.13–2.05 (1H, m); 1.94 (3H, bs); 1.68(3H, d); 1.59 (3H, d); 1.52 (6H, s)

EXAMPLE 8

2-Chloro-5-piperazin-1-ylmethyl-N-(tricyclo[3.3.1.1³,⁷]dec-1-ylmethyl)-benzamide, hydrochloride salt

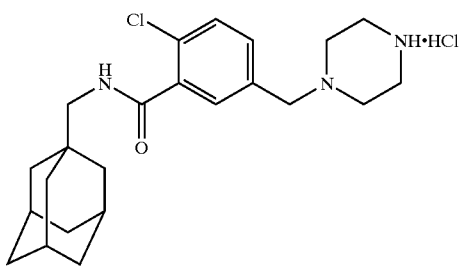

a) 5-Bromomethyl-2-chloro-benzoic acid

To a stirred solution of 2-chloro-5-methyl-benzoic acid (25 g) in chloroform (500 ml) at 50° C. was added N-bromosuccinimide (27.40 g). The flask was purged with nitrogen and azobisisobutyronitrile (0.10 g) added in one portion. The solution was heated at reflux for 1 h. Further azobisisobutyronitrile (0.10 g) was added and the mixture heated a further 3 h. The solution was concentrated in vacuo, redissolved in diethyl ether and filtered to remove insoluble succinimide. The ether solution was washed with 2N aqueos hydrochloric acid solution followed by brine then dried over magnesium sulphate. The solution was concentrated to a volume of 150 ml then diluted with isohexane. After further partial concentration crystallization started. The mixture was allowed to stand in an ice-bath for 1 h. The resulting crystals were filtered, washed with isohexane and dried in vacuo to give the subtitle compound (17 g).

b) 5-Bromomethyl-2-chloro-N-(tricyclo[3.3.1.13,7]dec-1-ylmethyl)-benzamide

To a stirred solution of 5-bromomethyl-2-chloro-benzoic acid (Example 8a, 12.4 g) in dichloromethane (250 ml) and dimethylformamide (0.12 ml) at 0° C. was added oxalyl chloride (8.7 ml). The cooling bath was removed and the solution allowed to warm to room temperature. Once gas evolution had ceased the solution was concentrated in vacuo. The residue was redissolved in dichloromethane (300 ml), cooled to 0° C. and treated with diisopropylethylamine (12.4 ml) and adamantylmethylamine (7.54 ml). After 15 min. at 0° C. the solution was poured into diethyl ether (1 L) and washed with 1N aqueous hydrochloric acid followed by brine. The organics were dried over magnesium sulphate and concentrated in vacuo to give the title compound as a white powder (19 g)

MS (APCI+ve) 396/398 (M+H)$^+$ $^1$H NMR (DMSO-d$_6$) δ 8.39 (1H, t); 7.50–7.40 (2H, m); 4.74 (2H, s); 2.92 (2H, d); 2.50 (3H, s); 1.94 (3H, bs); 1.67 (3H, d); 1.59 (3H, d); 1.52 (6H, s).

c) 2-Chloro-5-(4-[{1,1-dimethylethyl}oxycarbonyl]-piperazin-1-yl)methyl-N-(tricyclo[3.3.1.1$^{3,7}$]dec-1-ylmethyl)-benzamide A mixture of 5-bromomethyl-2-chloro-N-(tricyclo [3.3.1.1$^{3,7}$]dec-1-ylmethyl)-benzamide (Example 8b, 0.130 g), 1-tertbutyloxycarbonylpiperazine (0.074 g) and diisopropylethylamine (6.3 ml) in dimethylformamide (3 ml) was heated at 60° C. for 3 h. The mixture was diluted with water (10 ml) and extracted with ethyl acetate (3×10 ml). The organic layer was dried over magnesium sulfate, filtered and the filtrate concentrated under reduced pressure. The crude material was purified on a silica gel eluting with dichloromethane/ethanol (0–20% gradient) to afford the title compound as a white foam (0.112 g).

MS (APCI+ve) MW 502/504 (M+H)$^+$ $^1$H NMR (DMSO-d$_6$) δ 8.28 (1H, t); 7.40 (1H, d); 7.32 (1H, dd); 7.29 (1H, d); 3.74 (2H, s); 3.28 (4H, t); 2.90 (2H, d); 2.31 (4H, t); 1.92 (3H, bs); 1.70–1.50 (6H, m); 1.59 (6H, d); 1.37 (9H, s).

d) 2-Chloro-5-piperazin-1-ylmethyl-N-(tricyclo [3.3.1.1$^{3,7}$]dec-1-ylmethyl)-benzamide, hydrochloride salt 2-Chloro-5-(4-[{1,1-dimethylethyl}oxycarbonyl]-piperazin-1-yl)methyl-N-(tricyclo[3.3.1.1$^{3,7}$]dec-1-ylmethyl)-benzamide, (Example 8c, 0.080 g) was dissolved in methanol (3 ml), 4N HCl in dioxane (1 ml) was added and the mixture stirred at room temperature for 1.5 h. The solvent was removed under vacuum and the resulting solid was triturated with ether to afford the title compound as a white powder (0.062 g).

MS (APCI+ve) MW 402/404 (M+H)$^+$ $^1$H NMR (DMSO-d$_6$) δ 8.30 (1H, t); 7.63 (2H, bs); 7.55 (1H, d); 4.33 (1H, bs); 4.05 (4H, m); 3.50–3.00 (4H, m); 3.50–3.40 (1H, m); 2.92 (2H, d); 1.92 (3H, bs); 1.70–1.50 (6H, m); 1.57 (6H, bs).

According to the procedure described in Example 8, the following compounds were prepared.

EXAMPLE 9

2-Chloro-5-[(hexahydro-1H-1,4-diazepin-1-yl) methyl]-N-(tricyclo[3.3.1.1$^{3,7}$]dec-1-ylmethyl)-benzamide, hydrochloride salt

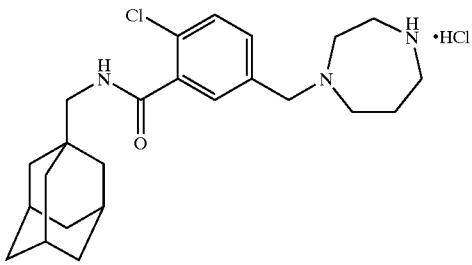

MS (APCI+ve) MW 416/418 (M+H)$^+$ $^1$H NMR (DMSO-d$_6$) δ 11.62 (bs, 1H), 9.57 (bs, 1H); 9.30 (bs, 1H); 8.34 (1H, t); 7.80–7.60 (2H, m); 7.59 (1H, d); 4.50–4.30 (bs, 2H); 3.80–3.00 (m, 8H); 2.94 (2H, d); 2.25–2.10 (m, 2H); 1.94 (3H, bs); 1.66 (3H, d); 1.58 (3H, d); 1.54 (6H, s).

EXAMPLE 10

5-[(4-Amino-1-piperidinyl)methyl]-2-chloro-N-(tricyclo[3.3.1.$^{3,7}$]dec-1-ylmethyl)-benzamide, hydrochloride salt

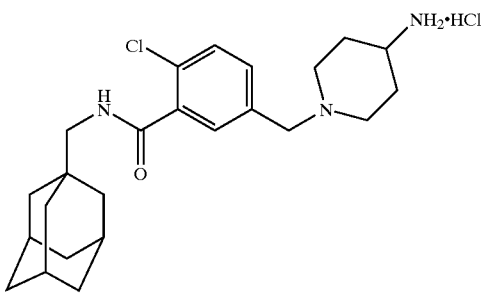

MS (APCI+ve) MW 416/418 (M+H)$^+$ $^1$H NMR (DMSO-d$_6$) δ 8.35 (1H, t); 8.30 (2H, bs); 7.66 (1H, d); 7.65 (1H, s); 7.59 (1H, d); 4.28 (d, 2H); 3.65–3.18 (m, 4H); 3.10–2.90 (1H, m); 2.95 (2H, d); 2.15–2.05 (2H, m); 2.05–1.90 (1H, m); 1.94 (3H, bs); 1.68 (3H, d); 1.61 (3H, d); 1.54 (6H, s).

EXAMPLE 11

5-[(3-Amino-1-pyrrolidinyl)methyl]-2-chloro-N-(tricyclo[3.3.1.1$^{3,7}$]dec-1-ylmethyl)-benzamide, hydrochloride salt

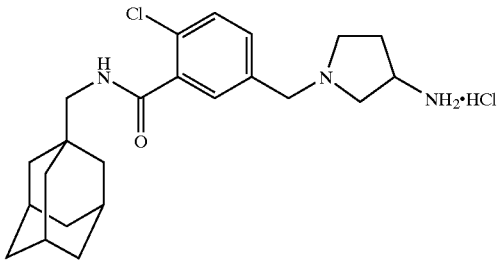

MS (APCI+ve) MW 402/404 (M+H)$^+$ $^1$H NMR (DMSO-$_6$) δ 8.56 (1H, bs); 8.42 (2H, bs); 8.35 (1H, t); 7.66 (2H, bs); 7.59 (1H, d); 4.60–4.40 (m, 2H); 4.20–3.00 (m, 5H); 2.94 (2H, d); 2.35–1.95 (m, 2H); 1.95 (3H, bs); 1.68 (3H, d); 1.61 (3H, d); 1.54 (6H, s).

EXAMPLE 12

2-Chloro-5-(4-piperidinyloxy)-N-(tricyclo[3.3.1.1$^{3,7}$]dec-1-ylmethyl)-benzamide, hydrochloride salt

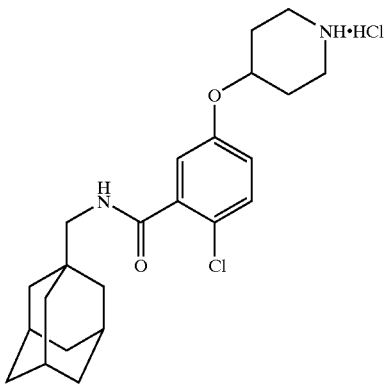

a) 2-Chloro-5-hydroxy-N-(tricyclo[3.3.1.13,7]dec-1-ylmethyl)-benzamide

To a solution of 2-chloro-5-hydroxybenzoic acid (3.12 g) in N,N-dimethylformamide (50 ml) was added 1,1'-carbonyldiimidazole (3.0 g). The resulting reaction mixture was stirred for 2.5 h and then 1-adamantanemethylamine (3.0 g) was added. Stirring was continued for 14 h. The reaction mixture was partitioned between ethyl acetate and water and the organic layer was separated, washed with water and brine and then dried over sodium sulphate (Na$_2$SO$_4$). The organic layer was concentrated under reduced pressure to give a residue which was purified by silica gel chromatography (eluting with 3–10% methanol in dichloromethane) to yield the subtitle compound as a white solid (0.15 g).

MS (APCI+ve) 319/321 (M+H)$^+$ $^1$H NMR (DMSO-d$_6$) δ 9.85(1H,s), 8.25 (1H, t), 7.24(1H, d), 6.76–6.82(2H, m), 2.90 (2H,d), 1.93(3H, s), 1.67 (3H, d), 1.57 (3H, d), 1.51 (6H, s)

b) 2-Chloro-5-(4-piperidinyloxy)-N-(tricyclo[3.3.1.1$^{3,7}$]dec-1-ylmethyl)-benzamide, hydrochloride salt To a solution of 2-chloro-5-hydroxy-N-(tricyclo[3.3.1.1$^{3,}$ $_7$]dec-1-methyl)-benzamide (0.20 g, Example 12a), 4-hydroxy-1-piperidinecarboxylic acid, 1,1-dimethylethyl ester (0.19 g) and tributylphosphine (0.23 ml) in dry tetrahydrofuran (6 ml) was added 1-[[(1-piperidinylcarbonyl)azo]carbonyl]-piperidine (0.24 g). The orange solution was heated at 60° C. under a nitrogen atmosphere for 2 h. At this point additional 4-hydroxy-1-piperidinecarboxylic acid, 1,1-dimethylethyl ester (0.19 g), tributylphosphine (0.23 ml) and 1-[[(1-piperidinylcarbonyl)azo]carbonyl]-piperidine (0.24 g) were added. Heating was continued and the process described above repeated until reaction was complete as judged by LC/MS. The cooled reaction mixture was diluted with diethyl ether then filtered. The filtrate was concentrated and purified by normal phase HPLC (0–2% methanol/dichloromethane) followed by chromatography on silica gel (0–2% methanol/dichloromethane) to give the t-butyloxycarbonyl (BOC)-protected compound as a colourless foam. The foam was dissolved in methanol (5 ml) and 4N hydrochloric acid in dioxane (0.25 ml) added. The solution was stirred at room temperature under a nitrogen atmosphere until the reaction was complete as judged by LC/MS. Evaporation of solvent followed by trituration with diethyl ether gave the title compound as a colourless solid (0.15 g).

MS (APCI+ve) 417/419 (M+H)+

$^1$H NMR (DMSO-d$_6$) δ 8.65 (2H, bs); 8.30 (1H, t); 7.39 (1H, d); 7.07 (1H, dd); 6.99 (1H, d); 4.72–4.67 (1H, m); 3.21 (2H, bm); 3.07 (2H, bm); 2.92 (2H, d); 2.12–2.07 (2H, m); 1.94 (3H,bs); 1.88–1.80 (2H, m); 1.67 (3H, d); 1.59 (3H, d); 1.52 (6H, s)

EXAMPLE 13

(R)-2-Chloro-5-(2-pyrrolidinylmethoxy)-N-(tricyclo[3.3.1.1$^{3,7}$]dec-1-ylmethyl)-benzamide, hydrochloride salt

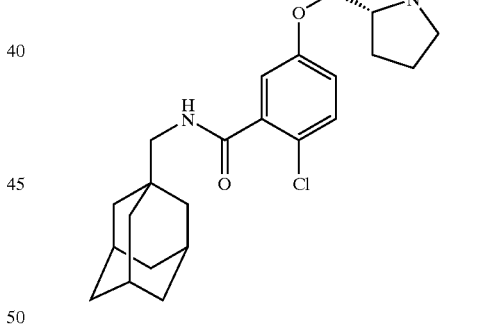

Prepared as described in Example 12b using 2-chloro-5-hydroxy-N-(tricyclo[3.3.1.1$^{3,7}$]dec-1-methyl)-benzamide (0.20 g, Example 12a), N-tBOC-D-prolinol (0.19 g) and tributylphosphine (0.23 ml), dry tetrahydrofuran (6 ml) and 1-[[(1-piperidinylcarbonyl)azo]carbonyl]-piperidine (0.24 g) to obtain the butyloxycarbonyl (BOC)-protected compound, followed by treatment with 4N hydrochloric acid in dioxane (0.4 ml) and methanol (5 ml) to yield the title compound as colourless solid (0.14 g)

MS (APCI+ve) 403/405 (M+H)+

$^1$H NMR (CD$_3$OD) δ 8.45 (1H, bt); 7.46 (1H, d); 7.14–7.10 (2H, m); 4.41 (1H, dd); 4.18 (1H, t); 4.10–4.04 (1H, m); 3.41 (2H, t); 3.10 (2H, m); 2.36–2.28 (1H, m); 2.25–2.08 (2H, d); 2.03 (3H, s); 2.00–1.90 (1H, m); 1.83 (3H, m); 1.74 (3H, d); 1.68 (6H, s)

EXAMPLE 14

(S)-2-Chloro-5-(2-pyrrolidinylmethoxy)-N-(tricyclo[3.3.1.1<sup>3,7</sup>]dec-1-ylmethyl)-benzamide, hydrochloride salt

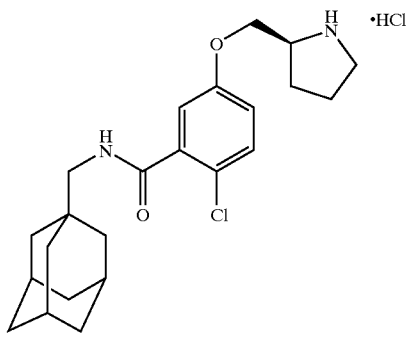

Prepared as described in Example 12b using 2-chloro-5-hydroxy-N-(tricyclo[3.3.1.1<sup>3,7</sup>]dec-1-methyl)-benzamide (0.20 g- Example 12a), N-tBOC-L-prolinol (0.19 g) and tributylphosphine (0.23 ml), dry tetrahydrofuran (6 ml) and 1-[[(1-piperidinylcarbonyl)azo]carbonyl]-piperidine (0.24 g) to obtain the t-butyloxycarbonyl (BOC)-protected compound, followed by treatment with 4N hydrochloric acid in dioxane (0.5 ml) and methanol (5 ml) to yield the title compound as colourless solid (0.07 g)

MS (APCI+ve) 403/405 (M+H)+

$^1$H NMR (CD$_3$OD) δ 8.45 (1H, bt); 7.46 (1H, d); 7.14–7.10 (2H, m); 4.41 (1H, dd); 4.18 (1H, t); 4.10–4.04 (1H, m); 3.41 (2H, t); 3.10 (2H, m); 2.36–2.28 (1H, m); 2.25–2.08 (2H, d); 2.03 (3H, s); 2.00–1.90 (1H, m); 1.83 (3H, m); 1.74 (3H, d); 1.68 (6H, s)

EXAMPLE 15

2-Chloro-5-(3-piperidinylmethoxy)-N-(tricyclo[3.3.1.1<sup>3,7</sup>]dec-1-ylmethyl)-benzamide, hydrochloride salt

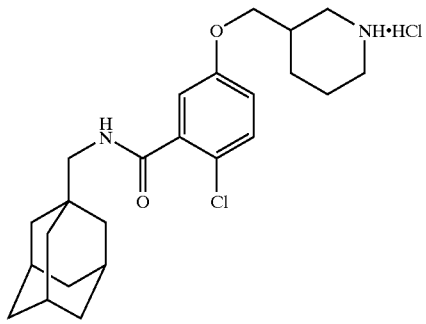

Prepared as described in Example 12b using 2chloro-5-hydroxy-N-(tricyclo[3.3.1.13,7]dec-1-methyl)-benzamide (0.20 g- Example 12a), 3-piperidinemethanol (0.20 g) and tributylphosphine (0.23 ml), dry tetrahydrofuran (6 ml) and 1-[[(1-piperidinylcarbonyl)azo]carbonyl]-piperidine (0.24 g) to obtain the t-butyloxycarbonyl (BOC)-protected compound. This compound was treated with 4N hydrochloric acid in dioxane (0.5 ml) and methanol (5 ml) to yield the title compound as colourless solid (0.09 g).

MS (APCI+ve) 417/19 (M+H)+

$^1$H NMR (DMSO-d6) δ 8.34 (2H, bs); 8.29 (1H, t); 7.38 (1H, d); 7.01 (1H, dd); 6.93 (1H, d); 3.99–3.95 (1H, m); 3.91–3.87 (1H, m); 3.34 (1H, m); 3.23 (1H, bd); 2.92 (2H, d); 2.82–2.71 (2H, m), 2.22 (1H, m); 1.94 (3H, s); 1.82 (2H, d); 1.72–1.66 (4H, m); 1.59 (3H, d); 1.52 (6H, s); 1.39–1.32 (1H, m)

EXAMPLE 16 cis-5-[(4-Aminocyclohexyl)oxy]-2-chloro-N-(tricyclo[3.3.1.1<sup>3,7</sup>]dec-1-ylmethyl)-benzamide, hydrochloride salt

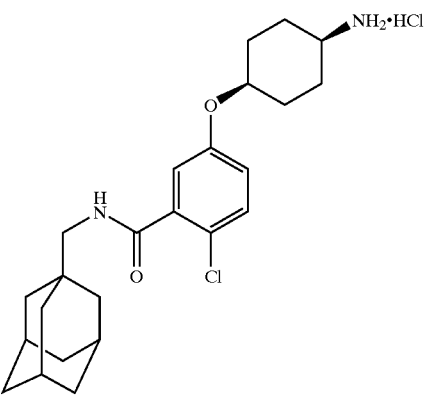

Prepared as described in Example 12b using 2-chloro-5-hydroxy-N-(tricyclo[3.3.1.1<sup>3,7</sup>]dec-1-methyl)-benzamide (0.20 g, Example 12a), trans4-amino-cyclohexanol (0.20 g) and tributylphosphine (0.23 ml), dry tetrahydrofuran (6 ml) and 1-[[(1-piperidinylcarbonyl)azo]carbonyl]-piperidine (0.24 g) to obtain the t-butyloxycarbonyl (BOC)-protected compound. This compound was treated with 4N hydrochloric acid in dioxane (0.5 ml) and methanol (5 ml) to yield the title compound as colourless solid (0.065 g).

MS (APCI+ve) 417/19 BP 417

$^1$H NMR (DMSO-d6) δ 8.30 (1H, t); 7.97 (3H, bs); 7.38 (1H, d); 7.02 (1H, dd); 6.92 (1H, d); 4.62 (1H, bs); 3.11 (1H, bs); 2.92 (2H, d); 1.94 (5H, s); 1.76–1.58 (12H, m); 1.52 (6H, s).

EXAMPLE 17

2-Methyl-5-(1-piperazinylmethyl)-N-(tricyclo[3.3.1.1<sup>3,7</sup>]dec-1-ylmethyl)-benzamide, hydrochloride salt

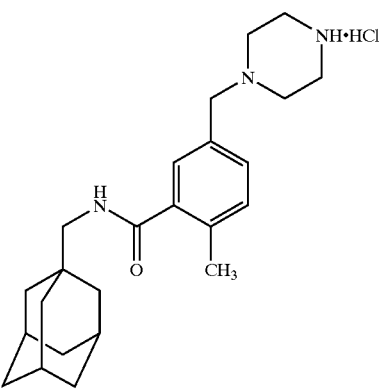

To a solution of 2-bromo-5-(4-[{1,1-dimethylethyl}oxycarbonyl]-piperazin-1-yl)methyl-N-

(tricyclo[3.3.1.1$^{3,7}$]dec-1-ylmethyl)-benzamide (0.20 g, Example 65b) and tetrakis(triphenylphosphine)palladium(0) (2 mg) in dry toluene (6 ml) was added tetramethyltin (0.2 ml). The solution was heated at 130° C. in a sealed tube for 18 hrs. The cooled reaction mixture was evaporated and the residue was treated with 10% KF solution in acetone and stirred for 45min. The mixture was concentrated and chromatographed on silica gel (isohexane then 60% ethyl acetate/40% isohexane) to give the t-butyloxycarbonyl (BOC)-protected compound as a colourless oil. The oil was dissolved in methanol (2 ml) and 4N hydrochloric acid in dioxane (1 ml) added. The solution was stirred at room temperature under a nitrogen atmosphere until the reaction was complete as judged by LC/MS. Evaporation of solvent followed by trituration with diethyl ether gave the title compound as a colourless solid (0.03 g).

MS (APCI+ve) 382 (M+H)+

$^1$H NMR (CD$_3$OD) δ 7.61 (1H, s); 7.55(1H, d); 7.39 (1H, d); 4.45 (2H, s); 3.67–3.46 (8H, bm); 3.08 (2H, s); 2.45 (3H, s); 1.99(3H, s); 1.78 (3H, d); 1.71 (3H, d); 1.62 (6H, s)

EXAMPLE 18

2-Chloro-5-(1-piperazinylmethyl)-N-(2-tricyclo [3.3.1.1$^{3,7}$]dec-1-ylethyl)-benzamide, hydrochloride salt

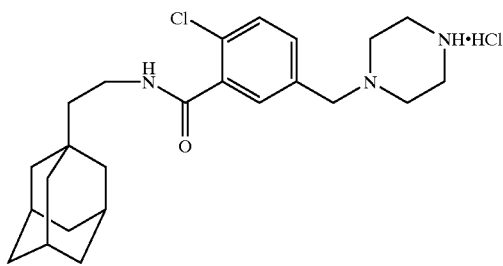

a) 5-(bromomethyl)-2-chloro-N-(2-tricyclo[3.3.1.1$^{3,7}$]dec-1-ylethyl)-benzamide To a solution of 2-chloro-5-(bromomethyl)-benzoic acid (1.0 g) in dichloromethane (25 ml) at 0° C. was added dimethylformamide (0.05 ml) followed by oxalyl chloride (0.52 ml). The reaction was allowed to warm to room temperature and stirred for 30 min. The volatiles were removed under vacuum and the residue dried under high vacuum. The acylchloride was dissolved in dichloromethane (20 ml) and added to a solution of 2-adamantanethylamine hydrochloride salt (0.95 g) in dichloromethane (20 ml) and diisopropylethylamine (2 ml) at 0° C. The reaction was allowed to warm to room temperature and stirred for 2 h. The organics were washed with water (20 ml) then saturated aqueous ammonium chloride solution and the organic layer dried over magnesium sulfate then filtered. The filtrate was concentrated under reduced pressure to a solid. The crude material was recrystallised from dichloromethane/hexane to afford the subtitle compound as a white solid (1.3 g).

b) 4-[[4-Chloro-3-[[(2-tricyclo[3.3.1.1$^{3,7}$]dec-1-ylethyl)amino]carbonyl]-phenyl]methyl]-1-piperazinecarboxylic acid, 1,1-dimethylethyl ester A mixture 5-(bromomethyl)-2-chloro-N-(2-tricyclo [3.3.1.1$^{3,7}$]dec-1-ylethyl)-benzamide (Example 18a, 0.35 g), 1-tertbutyloxycarbonylpiperazine (0.213 g), potassium carbonate (0.20 g) and potassium iodide (10 mg) in acetone (5 ml) was heated at 60° C. for 2 h. The acetone was removed under vacuum, the residue taken into dichlorometane and the solid removed by filtration. The crude material was purified on a silica gel eluting with dichloromethane/ethanol (0–10% gradient) to afford the subtitle compound as a white foam (0.383 g).

MS (APCI+ve) MW 516/518 (M+H)+

$^1$H NMR (CDCl$_3$) δ 7.63 (1H, bs); 7.34 (2H, bs); 6.09 (1H, bs); 3.60–3.30 (8H, m); 2.50–2.30 (4H, bs); 1.97 (3H, bs); 1.72 (3H, d); 1.68 (3H, d); 1.56 (6H, bs); 1.44 (9H, s); 1.50–1.35 (2H, m)

c) 2-Chloro-5-(1-piperazinylmethyl)-N-(2-tricyclo [3.3.1.1$^{3,7}$]dec-1-ylethyl)-benzamide, hydrochloride salt 4-[[4-chloro-3-[[(2-tricyclo[3.3.1.1$^{3,7}$]dec-1-ylethyl) amino]carbonyl]phenyl]methyl]-1-piperazinecarboxylic acid, 1,1-dimethylethyl ester, (Example 18b, 0.270 g) was dissolved in methanol (3 ml), 4N HCl in dioxane (2 ml) was added and the mixture stirred for 14 h at room temperature. The solvent was removed under vacuum and the resulting solid was triturated with ether to afford the title compound as a white powder (0.207 g).

MS (APCI+ve) MW 416/418 (M+H)+

$^1$H NMR (CD$_3$OD) δ 7.69 (1H, s); 7.66 (1H, d); 7.60 (1H, d); 4.86 (2H, s); 3.70–3.50 (8H, m); 3.50–3.35 (2H, m); 1.98 (3H, bs); 1.78 (3H, d); 1.70 (3H, d); 1.62 (6H, bs); 1.50–1.35 (2H, m).

EXAMPLE 19

(+/−)2-Chloro-5-(3-pyrrolidinyloxy)-N-(tricyclo [3.3.1.1$^{3,7}$]dec-1-ylmethyl)-benzamide, hydrochloride salt

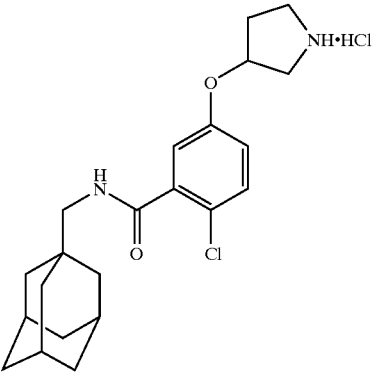

Prepared as described in Example 12b using 2-chloro-5-hydroxy-N-(tricyclo[3.3.1.1$^{3,7}$]dec-1-ylmethyl)-benzamide (0.155 g, Example 12a), tributylphosphine (0.23 ml), (+/−)-3-hydroxy-1-pyrrolidinecarboxylic acid, 1,1-dimethylethyl ester (0.19 g), 1-[[(1-piperidinylcarbonyl)azo]carbonyl]-piperidine (0.24 g) and dry tetrahydrofuran (10 ml) to give the t-butyloxycarbonyl (BOC)-protected compound as a colourless foam. This compound was treated with 4N hydrochloric acid in dioxane (0.5 ml) and methanol (5 ml) to yield the title compound as a colourless solid (0.075 g).

MS (APCI+ve) 389/391 (M+H)+

$^1$H NMR (CD$_3$OD) δ 8.42 (1H, bt); 7.42 (1H, d); 7.09–7.03 (2H, m); 5.23 (1H, bm); 3.59–3.41 (4H, m); 3.07 (2H, d); 2.36–2.30 (2H, m); 1.99 (3H, bs); 1.79 (3H, d); 1.70 (3H, d); 1.63 (6H, d)

EXAMPLE 20

(+/−)-2-Chloro-5-(3-piperidinyloxy)-N-(tricyclo[3.3.1.1³,⁷]dec-1-ylmethyl)-benzamide, hydrochloride salt

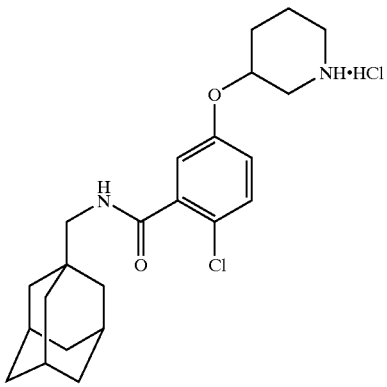

Prepared as described in Example 12b using 2-chloro-5-hydroxy-N-(tricyclo[3.3.1.1³,⁷]dec-1-ylmethyl)-benzamide (0.15 g, Example 12a), tributylphosphine (2×0.18 ml), 3-hydroxy-1-piperidinecarhoxylic acid, 1,1I-dimethylethyl ester (2×0.14 g), 1-[[(1-piperidinylcarbonyl)azo]carbonyl]-piperidine (2×0.18 g) and dry tetrahydrofuran (6 ml) to give the t-butyloxycarbonyl (BOC)-protected compound as a colourless foam. This compound was treated with 4N hydrochloric acid in dioxane (0.25 ml) and methanol (5 ml) to yield the title compound as a colourless foam (0.042 g).

MS (APCI+ve) 403/405 (M+H)+

¹H NMR (CD₃OD) δ 8.42 (1H, t); 7.41 (1H, d); 7.14–7.10 (2H, m); 4.82 (1H, bm); 3.51–3.39 (1H, m); 3.38 (2H, m); 3.20–3.17 (1H, m); 3.06 (2H, d); 2.10–2.04 (2H, m); 2.00 (3H, bs); 1.94–1.89 (1H, m); 1.84–1.68 (7H, d); 1.64 (6H, d)

EXAMPLE 21 trans-5-[(4-Amninocyclohexyl)oxy]-2-chloro-N-(tricyclo[3.3.1.1³,⁷]dec-1-ylmethyl)-benzamide

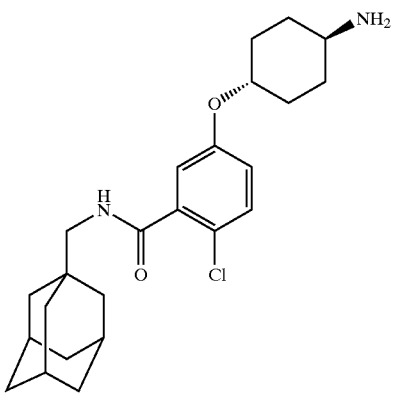

Prepared as described in Example 12b using 2-chloro-5-hydroxy-N-(tricyclo[3.3.1.1³,⁷]dec-1-ylmethyl)-benzamide (0.15 g, Example 12a), tributylphosphine (3×0.18 ml), cis-(4-hydroxycyclohexyl)-carbamic acid, 1,1-dimethylethyl ester (3×0.15 g), 1-[[(1-piperidinylcarbonyl)azo]carbonyl]-piperidine (3×0.18 g) and dry tetrahydrofuran (6 ml) to give the t-butyloxycarbonyl (BOC)-protected compound as a colourless foam. This compound was treated with 4N hydrochloric acid in dioxane (0.5 ml) and methanol (3 ml) to yield the title compound as a colourless foam (0.080 g).

MS (APCI+ve) 417/419 (M+H)+

¹H NMR (CD₃OD) δ 8.38 (1H, t); 7.34 (1H, d); 6.98 (1H, dd); 6.96 (1H, d); 4.30 (1H, m); 3.17 (1H, m); 3.04 (2H, d); 2.22 (2H, bm); 2.09 (2H, m); 1.98 (3H, bs); 1.77 (3H, d); 1.68 (3H, d); 1.62 (6H, s); 1.55 (4H, m)

EXAMPLE 22 cis-(+/−)-5-[(3-Aminocyclopentyl)oxy]-2-chloro-N-(tricyclo[3.3.1.1³,⁷]dec-1-ylmethyl)-benzamide

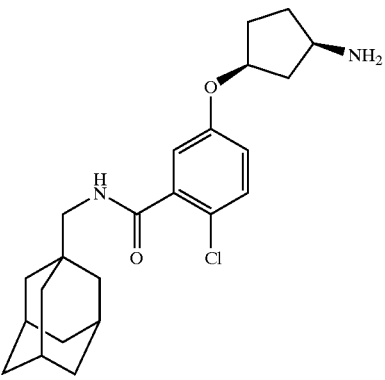

Prepared as described in Example 12b using 2-chloro-5-hydroxy-N-(tricyclo[3.3.1.1³,⁷]dec-1-ylmethyl)-benzamide (0.20 g, Example 12a), tributylphosphine (0.24 ml), trans-(+/−)-(3-hydroxycyclopentyl)-carbamic acid, 1,1-dimethylethyl ester (0.19 g), 1-[[(1-piperidinylcarbonyl)azo]carbonyl]-piperidine (0.24 g) and dry tetrahydrofuran (3 ml) to give the t-butyloxycarbonyl (BOC)-protected compound as a colourless foam. This compound was treated with 4N hydrochloric acid in dioxane (0.5 ml) and methanol (5 ml) to yield the title compound as a colourless foam (0.15 g).

MS (APCI+ve) 403/405 (M+H)+

¹H NMR (CD₃OD) δ 7.36 (1H, d); 7.02–6.98 (2H, m); 4.94–4.90 (1H, m); 3.75–3.68 (1H, m); 3.04 (2H, s); 2.55 (1H, m); 2.24–2.17 (1H, m); 2.09–2.03 (2H, m); 1.98–1.86 (5H, m); 1.76 (3H, d); 1.68 (3H, d); 1.62 (6H, d)

EXAMPLE 23

(S,S)-2-Chloro-5-(2,5-diazabicyclo[2.2.1]hept-2-yl)-
N-(tricyclo[3.3.1.1$^{3,7}$]dec-1-ylmethyl)-benzamide,
hydrochloride salt

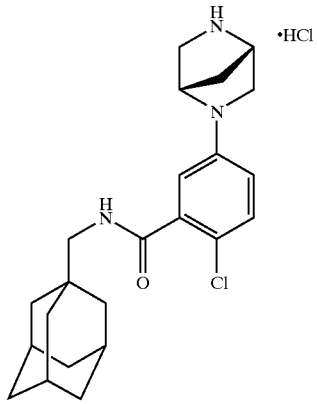

a) 5-Bromo-2-chloro-N-(tricyclo[3.3.1.1$^{3,7}$]dec-1-ylmethyl)-benzamide

Prepared as in Example 1a from 5-bromo-2-chlorobenzoic acid (7.17 g), oxalyl chloride (5.3 ml), dichloromethane (150 ml), dimethylformamide (0.05 ml), diisopropylethylamine (6 ml) and adamantylmethylamine (5 ml) to give the subtitle compound as white colourless needles (7.3 g).

MS (APCI-ve) 382/384 (M−H)+ b) (S,S)-2-Chloro-5-(2,5-diazabicyclo[2.2.1]hept-2-yl)-N-(tricyclo[3.3.1.1$^{3,7}$]dec-1-ylmethyl)-benzamide, hydrochloride salt A mixture of 5-bromo-2-chloro-N-(tricyclo[3.3.1.1$^{3,7}$]dec-1-ylmethyl)-benzamide (1.70 g, Example 23a), 2,5-diazabicyclo[2.2.1]heptane-2-carboxylic acid, 1,1-dimethylethyl ester (1.06 g), cesium carbonate (2.20 g), (R)-(+)-2,2'-bis(diphenylphosphino)-1,1'-binaphthyl ((R)-(+)-BINAP, 0.20 g), and palladium (II) acetate (0.050 g) in dry toluene (10 ml) was heated at 100° C. under nitrogen for 24 h. The cooled reaction mixture was filtered, washing the residue with ethyl acetate. The filtrate was washed with water and brine, dried (MgSO$_4$) and evaporated under reduced pressure to give an orange oil. The oil was purified by chromatography on silica gel, eluting with 0.5% methanol/dichloromethane to yield the t-butyloxycarbonyl (BOC) protected compound as a colourless foam. The foam was dissolved in methanol (20 ml) and 4N hydrochloric acid in dioxane (2.5 ml) added. The solution was stirred at room temperature until reaction was complete (LCMS). The solution was then evaporated under reduced pressure and the residue triturated with diethyl ether to afford the title compound as an off-white solid (0.92 g).

MS (APCI+ve) 400/402 (M−HCl)+

$^1$H NMR (CD$_3$OD) δ 8.32 (1H, t); 7.30 (1H, d); 6.77–3.70 (2H, m); 4.69 (1H, s); 4.50 (1H, s); 3.73 (1H, dd); 3.67 (2H, s); 3.06 (2H, d); 2.30 (1H, bd); 2.06 (1H, bd); 1.99 (3H, bs); 1.78 (3H, d); 1.70 (3H, d); 1.64 (6H, s); 1.55 (4H, m) Methanol peak masks other $^1$H signal.

EXAMPLE 24

2-Chloro-5-(2-methyl-1-piperazinyl)-N-(tricyclo[3.3.1.1$^{3,7}$]dec-1-ylmethyl)-benzamide,
hydrochloride salt

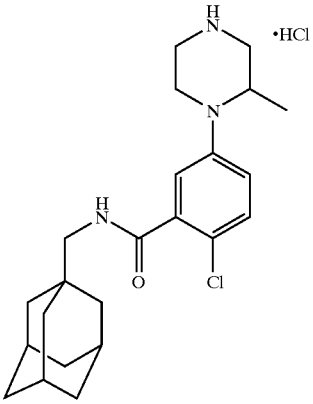

Prepared as described in Example 23 above from 5-bromo-2-chloro-N-(tricyclo[3.3.1.1$^{3,7}$]dec-1-ylmethyl)-benzamide (0.30 g, Example 23a), 3-methyl-1-piperazinecarboxylic acid, 1,1-dimethylethyl ester (0.20 g), cesium carbonate (0.36 g), (R)-(+)-2,2'-bis(diphenylphosphino)-1,1'-binaphthyl ((R)-(+)-BINAP, 0.036 g), palladium (II) acetate (0.009 g) and dry toluene (10 ml) to yield the t-butyloxycarbonyl (BOC)-protected compound. This compound was treated with 4N hydrochloric acid in dioxane (0.5 ml) and methanol (5 ml) to yield the title compound as a solid (0.025 g).

MS (APCI+ve) 402/404 (M−HCl)+

$^1$H NMR (CD$_3$OD) δ 8.40 (1H, t); 7.37 (1H, d); 7.11 (1H, dd); 7.07 (1H, d); 4.00–3.96 (1H, m); 3.43–3.39 (3H, m); 3.28–3.19 (3H, m); 3.06 (2H, d); 1.98 (3H, bs); 1.77 (3H, d); 1.70 (3H, d); 1.63 (6H, s); 1.10 (3H, d).

EXAMPLE 25

(+/−)-2-Chloro-5-(3-pyrrolidinylamino)-N-(tricyclo[3.3.1.1$^{3,7}$]dec-1-ylmethyl)-benzamide,
hydrochloride salt

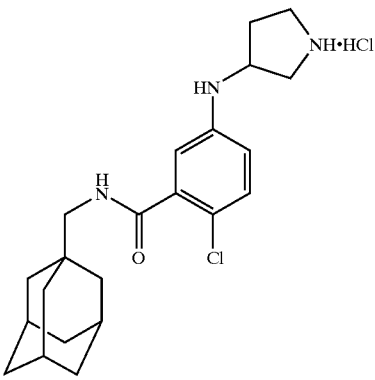

Prepared as described in Example 23 above from 5-bromo-2-chloro-N-(tricyclo[3.3.1.1$^{3,7}$]dec-1-ylmethyl)-benzamide (0.30 g, Example 23a), 3-amino-1-pyrrolidinecarboxylic acid, 1,1-dimethylethyl ester (0.18 g), cesium carbonate (0.36 g), (R)-BINAP (0.036 g), anhydrous toluene (3 ml) and palladium (II) acetate (0.009 g); the mixture was heated for 14 h in a pressure vessel flushed with nitrogen. Additional (R)-BINAP (0.036 g) and palladium (II) acetate (0.009 g) were added and heating continued for a further 24 h. The cooled reaction mixture was poured into water and extracted with ethyl acetate three times. The organic fractions were combined and washed with water then brine, and dried (MgSO$_4$). Evaporation under reduced pressure gave an oil which was purified by normal phase HPLC (0–5% methanol/dichloromethane) to yield the t-butyloxycarbonyl (BOC)- protected compound as a colourless foam. The foam was dissolved in methanol (5 ml) and 4N hydrochloric acid in dioxane (0.5 ml) added. The solution was stirred at room temperature under a nitrogen atmosphere until the reaction was complete as judged by LCMS. Evaporation followed by trituration with diethyl ether and methanol yielded the title compound as an off-white solid/foam (0.040 g).

MS (APCI+ve) 388/390 (M−HCl)+

$^1$H NMR (CD$_3$OD) δ 8.20 (1H, bt); 7.12 (1H, d); 6.63–6.60 (2H, m); 4.76–4.08 (1H, m); 3.43–3.38 (2H, m); 3.35–3.28 (1H, m); 3.25 (1H, m); 2.94 (2H, s); 2.31–2.22 (1H, m); 2.01–1.94 (1H, m); 1.89 (3H, bs), 1.67 (3H, d); 1.60 (3H, d); 1.53 (6H, s)

EXAMPLE 26

(+/−)-5-(3-Amino-1-piperidinyl)-2-chloro-N-(tricyclo[3.3.1.1$^{3,7}$]dec-1-ylmethyl)-benzamide

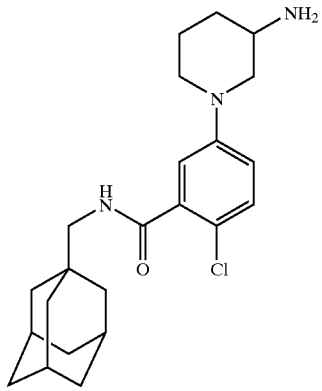

Prepared as described in Example 23 above from 5-bromo-2-chloro-N-(tricyclo[3.3.1.1$^{3,7}$]dec-1-ylmethyl)-benzamide (0.20 g, Example 23a), 3-piperidinyl-carbamic acid, 1,1-dimethylethyl ester (0.12 g), cesium carbonate (0.24 g), (R)-(+)-2,2'-bis(diphenylphosphino)-1,1'-binaphthyl ((R)-(+)-BINAP, 0.024 g), palladium (II) acetate (0.006 g) and dry toluene (3 ml) to yield the t-butoxycarbonyl (BOC)-protected compound. The t-butoxycarbonyl (BOC)-protected compound was dissolved in methanol (5 ml) and hydrochloric acid (0.5 ml of a 4N solution in dioxane). After stirring at room temperature for 24 h the mixture was evaporated and the residue partitioned between ethyl acetate and saturated sodium bicarbonate. The layers were separated and the aqueous phase acidified with 2M hydrochloric acid and extracted with ethyl acetate. The organic phase was dried over magnesium sulfate and then evaporated under reduced pressure to give a gum. Purification by chormatography on silica gel, eluting with 4–10% methanol in dichloromethane/aqueous ammonia afforded the title compound as a solid (0.036 g).

MS (APCI+ve) 402/404 (M+H)+

$^1$H NMR (CD$_3$OD) δ 7.25 (1H, d); 7.00 (1H, dd); 6.96 (1H, d); 3.59 (1H, dd); 3.48–3.45 (1H, m); 3.04 (2H, d); 2.91–2.85 (1H, m); 2.82–2.75 (1H, m); 2.58 (1H, dd); 1.98–1.93 (4H, m); 1.85–1.75 (3H, d); 1.70–1.62 (10H, d); 1.34–1.25 (1H, d).

EXAMPLE 27

(+/−)-2-Chloro-5-(3-piperidinylamino)-N-(tricyclo[3.3.1.1$^{3,7}$]dec-1-ylmethyl)-benzamide

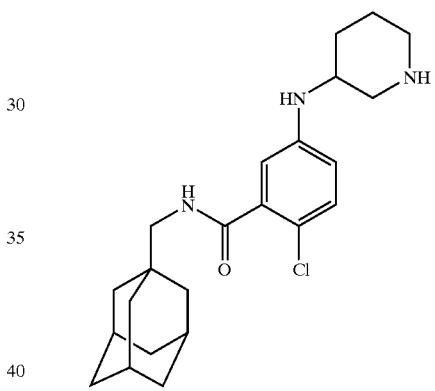

Prepared as described in Example 23 above from 5-bromo-2-chloro-N-(tricyclo[3.3.1.1$^{3,7}$]dec-1-ylmethyl)-benzamide (0.30 g, Example 23a), 3-amino-1-piperidinecarboxylic acid, 1,1-dimethylethyl ester (0.19 g), cesium carbonate (0.36 g), (R)-(+)-2,2'-bis(diphenylphosphino)-1,1'-binaphthyl ((R)-(+)-BINAP, 0.036 g), palladium (II) acetate (0.008 g) and dry toluene (3 ml) to yield the t-butyloxycarbonyl (BOC)-protected compound. This compound was treated with methanol (5 ml) and hydrochloric acid (0.5 ml of a 4 M solution in dioxane) followed by an acid/base work-up. Purification by chromatography on silica gel, eluting with 4–10% methanol in dichloromethane/aqueous ammonia afforded the title compound as a solid (0.008 g).

MS (APCI+ve) 402/404 (M+H)+

1H NMR (CD$_3$OD) δ 7.14 (1H, d); 6.68–6.65 (2H, m); 3.47–3.40 (1H, m); 3.25 (1H, m); 3.05–3.02 (3H, m); 2.72–2.65 (1H, m); 2.52–2.47 (1H, m); 2.08–2.04 (1H, m); 1.97 (3H, bs); 1.89–1.82 (1H, m); 1.77 (3H, d); 1.70–1.62 (10H, d); 1.50–1.40 (1H, m).

EXAMPLE 28

2-Chloro-5-[hexahydropyrrolo[3,4-c]pyrrol-2(1H)-yl]-N-(tricyclo[3.3.1.1^{3,7}]dec-1-ylmethyl)-benzamide

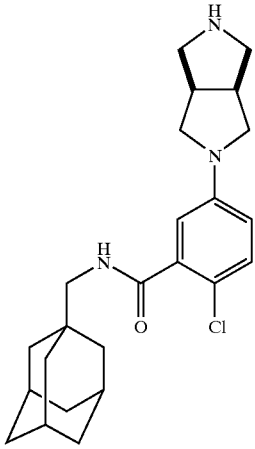

Prepared as described in Example 23 above from 5-bromo-2-chloro-N-(tricyclo[3.3.1.1$^{3,7}$]dec-1-ylmethyl)-benzamide (0.15 g, Example 23a), hexahydro-pyrrolo[3,4-c]pyrrole-2(1H)-carboxylic acid, 1,1-dimethylethyl ester (0.17 g), cesium carbonate (0.33 g), (R)-(+)-2,2'-bis(diphenylphosphino)-1,1'-binaphthyl ((R)-(+)-BINAP, 0.018 g), palladium (II) acetate (0.004 g) and dry toluene (2 ml) to yield the t-butyloxycarbonyl (BOC)-protected compound. This compound was treated with methanol (5 ml) and hydrochloric acid (0.5 ml of a 4 M solution in dioxane) followed by an acid/base work-up. Trituration of the residue with dichloromethane afforded the title compound as a solid (0.020 g).

MS (APCI+ve) 414/416(M+H)+

$^1$H NMR (CD$_3$OD) δ 8.17 (1H, t); 7.20(1H, d); 6.63 (1H, dd); 6.54 (1H, d); 3.36 (2H, m); 3.02 (2H, dd); 2.95–2.90 (4H, m); 2.80 (2H, m); 2.60 (2H, dd)); 1.94 (3H, bs); 1.67 (3H, d); 1.59 (3H, d); 1.52 (6H, d).

EXAMPLE 29

N-[2-methyl-5-(4-piperidinyloxy)phenyl]-tricyclo[3.3.1.1$^{3,7}$]decane-1-acetamide, hydrochloride salt

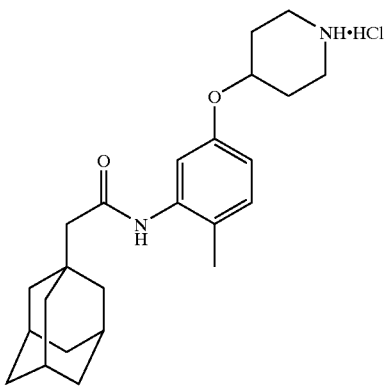

Prepared as described in Example 12b using N-(5-hydroxy-2-methylphenyl)-tricyclo[3.3.1.1$^{3,7}$]decane-1-acetamide (0.51 g, Example 12, WO 99/29660), tributylphosphine (0.64 ml), 1-[[(1-piperidinylcarbonyl)azo]carbonyl]-piperidine (0.65 g), 4-hydroxy-1-piperidinecarboxylic acid, 1,1-dimethyl ethyl ester (0.52 g) and dry tetrahydrofuran (10 ml) to give the t-butyloxycarbonyl (BOC) protected compound as a colourless solid. This compound was treated with 4N hydrochloric acid in dioxane (0.5 ml) and methanol (5 ml) to yield the title compound as a colourless solid (0.13 g).

MS (APCI+ve) 383 (M–HCl)+

$^1$H NMR (CD$_3$OD) δ 7.19 (1H, d); 7.12 (1H, d); 6.83 (1H, dd); 4.71–466 (1H, m); 3.46–3.40 (2H, m); 3.28–3.22 (2H, m); 2.25 (3H, s); 2.21 (1H, s); 2.21–2.14 (2H, m); 2.11–2.04 (5H, m); 1.84–1.73 (12H, m).

EXAMPLE 30

N-[2-chloro-5-(4-piperidinyloxy)phenyl]-tricyclo[3.3.1.1$^{3,7}$]decane-1-acetamide, hydrochloride salt

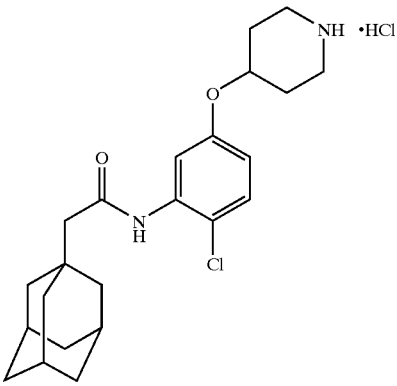

Prepared as described in Example 12b using N-(2-chloro-5-hydroxyphenyl)-tricyclo[3.3.1.1$^{3,7}$]decane-1-acetamide (0.25 g, Example 28, WO 99/29660), tributylphosphine (0.29 ml), 1-[[(1-piperidinylcarbonyl)azo]carbonyl]-piperidine (0.30 g), 4-hydroxy-1-piperidinecarboxylic acid, 1,1-dimethylethyl ester (0.24 g) and dry tetrahydrofuran (10 ml) to give the t-butyloxycarbonyl (BOC) protected compound as a colourless solid. This compound was treated with 4N hydrochloric acid in dioxane (1 ml) and methanol (20 ml) to yield the title compound as a colourless solid (0.08 g).

MS (APCI+ve) 375/377 (M–HCl)+

$^1$H NMR (CD$_3$OD) δ 7.55 (1H, d); 7.41 (1H, d); 6.88 (1H, dd); 4.76–4.70 (1H, m); 3.48–3.39 (2H, m); 3.30–3.22 (2H, m); 2.25 (2H, s); 2.22–2.16 (2H, m); 2.14–2.03 (2H, m); 1.84–1.72 (12H, m).

EXAMPLE 31

2-Chloro-5-[(4-piperidinylamino)methyl]-N-(tricyclo[3.3.1.1$^{3,7}$]dec-1-ylmethyl)-benzamide, dihydrochloride salt

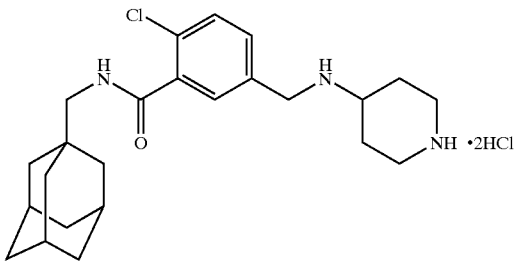

a) 2-Chloro-5-formyl-N-(tricyclo[3.3.1.1$^{3,7}$]dec-1-ylmethyl)-benzamide

A solution of 5-bromo-2-chloro-N-(tricyclo[3.3.1.1$^{3,7}$]dec-1-ylmethyl)-benzamide (3.25 g, Example 23a) in anhydrous tetrahydrofuran (150 ml) was cooled to −78° C. under a nitrogen atmosphere. A solution of methyllithium (1.4M in diethyl ether, 6.1 ml) was added over 2 min. The mixture was stirred at −78° C. for 10 min, then a solution tert-butyllithium (1.7M in pentane, 10.0 ml) was added dropwise. The mixture was stirred at −78° C. for a further 10 min, then dimethylformamide (1.0 ml) was added. The resulting solution was stirred at −78° C. for 30 min., quenched with saturated aqueous ammonium chloride solution (100 ml) and extracted with ethyl acetate. The combined extracts were dried over anhydrous magnesium sulfate, filtered, and the filtrate concentrated under reduced pressure to give the subtitle compound as a solid (2.76 g).

MS (APCI+ve) 332 (M+H)+

$^1$H NMR (DMSO-d6) δ 10.04 (1H, s); 8.49 (1H, t); 7.96–7.91 (2H, m); 7.74 (1H, d); 2.96 (2H, d), 1.95 (3H, s); 1.64 (6H, AB); 1.53 (6H, d).

b) 4-[4-Chloro-3-[(tricyclo[3.3.1.1$^{3,7}$]dec-1-ylmethyl)amino]carbonyl]phenyl]methyl]amino]-1-piperidinecarboxylic acid, 1,1-dimethylethyl ester 2-Chloro-5-formyl-N-(tricyclo [3.3.1.1$^{3,7}$]dec-1-ylmethyl)-benzamide (0.270 g, Example 31a) and 3-amino-1-pyrrolidinecarboxylic acid, 1,1-dimethylethyl ester (0.325 g, Journal of Medicinal Chemistry, 1998, 41(22), 4273–4278) were dissolved in 1,2-dichloroethane (30 ml), under a nitrogen atmosphere. Sodium triacetoxyborohydride (0.24 g) was added and the mixture was stirred for 14 h at room temperature. Water and dichloromethane were added and the layers were partitioned. The organic extracts were dried over anhydrous magnesium sulfate, filtered and concentrated under reduced pressure. The residue was purified by HPLC eluting with a gradient of 0–10% of ethanol in dichloromethane, then by chromatography over silica gel eluting with ethyl acetate: iso-hexane (1:1) then ethyl acetate: ethanol (98:2) to give the subtitle compound as a colourless oil (0.158 g).

MS (APCI+ve) 516 (M+H)+ c) 2-Chloro-5-[(4-piperidinylamino)methyl]-N-(tricyclo[3.3.1.1$^{3,7}$]dec-1-ylmethyl)-benzamide, dihydrochloride salt Prepared from 4-[[[4chloro-3-[[(tricyclo[3.3.1.1$^{3,7}$]dec-1-ylmethyl)amino]carbonyl]phenyl]methyl]amino]-1-piperidinecarboxylic acid, 1,1-dimethylethyl ester (0.158 g, Example 31b) methanol (3 ml) and 4N hydrochloric acid solution in dioxane (2 ml). Solvents were removed under reduced pressure and the residue was triturated with ethyl acetate, iso-hexane and diethyl ether to give the title compound as a white solid (0.126 g).

MS (APCI+ve) 416 (M+H-2HCl)+

$^1$H NMR (CD$_3$OD) δ 8.47 (1H, t); 7.62–7.56 (3H, m), 4.33 (2H, s); 3.58–3.55 (3H, m); 3.12 (2H, t); 3.07 (2H, d); 2.44 (2H, d); 2.03–1.92 (5H, m); 1.73 (6H, q); 1.63 (6H, d).

EXAMPLE 32

5-[[[4-(Aminomethyl)cyclohexyl]amino]methyl]-2-chloro-N-(tricyclo[3.3.1.1$^{3,7}$]dec-1-ylmethyl)-benzamide, dihydrochloride salt

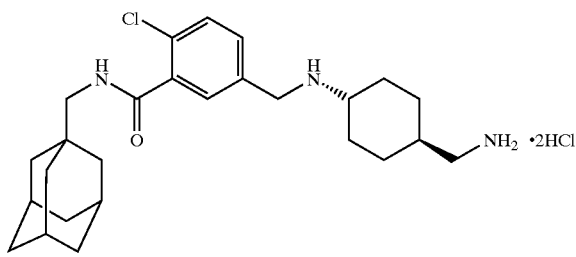

a) [[4-[[[4-Chloro-3-[[(tricyclo[3.3.1.1$^{3,7}$]dec-1-ylmethyl)amino]carbonyl]phenyl]methyl]amino]cyclohexyl]methyl]-carbamic acid, 1,1-dimethylethyl ester Prepared according to the method described in Example 31b from 2-chloro-5-formyl-N-(tricyclo [3.3.1.1$^{3,7}$]dec-1-ylmethyl)-benzamide (0.30 g, Example 31a), [(4-aminocyclohexyl)methyl]-carbamic acid, 1,1-dimethylethyl ester (0.207 g, WO 97/32882), sodium triacetoxyborohydride (0.135 g) and 1,2-dichloroethane (10 ml). The residue was purified by chromatography over silica gel eluting with ethyl acetate: iso-hexane (1:1) then ethyl acetate: ethanol (9:1) to give the subtitle compound as a colourless oil (0.26 g).

MS (APCI+ve) 544 (M+H)+ b) 5-[[[4-(Aminomethyl)cyclohexyl]amino]methyl]-2-chloro-N-(tricyclo[3.3.1.1$^{3,7}$]dec-1-ylmethyl)-benzamide, dihydrochloride salt Prepared from [[4-[[[4chloro-3-[[(tricyclo[3.3.1.1$^{3,7}$]dec-1-ylmethyl)amino]carbonyl]phenyl]methyl]amino]cyclohexyl]methyl]-carbamic acid, 1,1-dimethylethyl ester (0.26 g, Example 32a) methanol (5 ml) and 4N hydrochloric acid solution in dioxane (2 ml). Solvents were removed under reduced pressure and the residue was triturated with diethyl ether to give the title compound as a white powder (0.191 g).

MS (APCI+ve) 444 (M+H-2HCl)+

$^1$H NMR (CD$_3$OD) δ 7.60–7.58 (3H, m), 4.29 (2H, s); 3.28–3.12 (1H, m); 3.09 (2H, s); 2.84 (2H, d); 2.31 (2H, bd); 2.00 (5H, bs); 1.75 (6H, q); 1.65 (6H, d); 1.71–1.65 (1H, m); 1.63–1.44 (2H, m); 1.31–1.12 (2H, m).

EXAMPLE 33

5-[[(4-Aminocyclohexyl)amino]methyl]-2-chloro-N-(tricyclo[3.3.1.1³,⁷]dec-1-ylmethyl)-benzamide, dihydrochloride salt

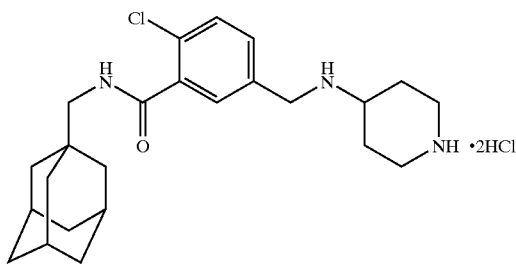

a) [4-[[[4-chloro-3-[[(tricyclo[3.3.1.1³,⁷]dec-1-ylmethyl)amino]carbonyl]phenyl]-methyl]amino]cyclohexyl]-carbamic acid, 1,1-dimethylethyl ester Prepared according to the method described in Example 31b from 2-chloro-5-formyl-N-(tricyclo[3.3.1.1³,⁷]dec-1-ylmethyl)-benzamide (0.30 g, Example 31a), (4-aminocyclohexyl)-carbamic acid, 1,1-dimethylethyl ester (0.194 g, Journal of Organic Chemistry, 1996, 61(25), 8811–8818), sodium triacetoxyborohydride (0.135 g) and 1,2-dichloroethane (10 ml). The residue was purified by chromatography over silica gel eluting with ethyl acetate: iso-hexane (1:1) then ethyl acetate: ethanol (95:5) to give the subtitle compound as a colourless oil (0.24 g).

MS (APCI+ve) 530 (M+H)+ b) 5-[[(4-Aminocyclohexyl)amino]methyl]-2-chloro-N-(tricyclo[3.3.1.1³,⁷]dec-1-ylmethyl)-benzamide, dihydrochloride salt Prepared from [4-[[[4-chloro-3-[[(tricyclo[3.3.1.1³,⁷]dec-1-ylmethyl)amino]carbonyl]phenyl]methyl]amino]cyclohexyl]-carbamic acid, 1,1-dimethylethyl ester (0.26 g, Example 33a), methanol (5 ml) and 4N hydrochloric acid solution in dioxane (1 ml). Solvents were removed under reduced pressure and the residue was triturated with diethyl ether to give the title compound as a white powder (0.190 g).

MS (APCI+ve) 430 (M+H-2HCl)+

¹H NMR (CD₃OD) δ 7.61–7.59 (3H, m), 4.30 (2H, s); 3.28–3.11 (2H, m); 3.08 (2H, s); 2.40–2.32 (2H, m); 2.21–2.17 (2H, m); 2.00 (3H, s); 1.74 (6H, q); 1.64 (6H, d); 1.63–1.48 (4H, m).

EXAMPLE 34

5-[(1-Azabicyclo[2.2.2]oct-3-ylamino)methyl]-2-chloro-N-(tricyclo[3.3.1.1³,⁷]dec-1-ylmethyl)-benzamide

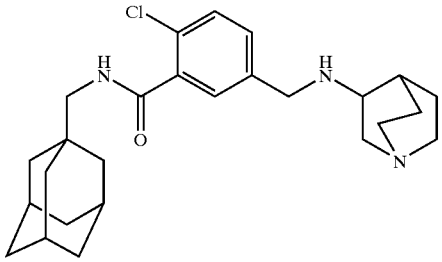

Prepared according to the method described in Example 31b from 2-chloro-5-formyl-N-(tricyclo[3.3.1.1³,⁷]dec-1-ylmethyl)-benzamide (0.30 g, Example 31a), 1-azabicyclo[2.2.2]octan-3-amine dihydrochloride salt (0.18 g), sodium triacetoxyborohydride (0.135 g) and 1,2-dichloroethane (10 ml). The residue was purified by chromatography over silica gel eluting with ethyl acetate: iso-hexane (1:1) followed by ethyl acetate: ethanol (95:5). Repurification by chromatography over silica gel eluting with dichloromethane: methanol (95:5) then (9:1) gave the title compound as a white gum (0.013 g).

MS (APCI+ve) 442 (M+H)+

¹H NMR (CDCl₃) δ 7.68 (1H, d); 7.39 (1H, d); 7.31 (1H, dd); 6.41 (1H, t); 3.75 (2H, s); 3.42–3.31 (2H, m); 3.25–3.09 (6H, m); 2.94 (1H, d); 2.38–2.23 (2H, m); 2.22–2.14 (1H, m); 2.01 (3H, s); 1.92–1.83 (2H, m); 1.69 (6H, q); 1.59 (6H, d).

EXAMPLE 35

N-[4-(3-Aminopyrrolidin-1-yl)-2-methylphenyl]-2-(tricyclo[3.3.1.13,7]dec-1-yl)acetamide, dihydrochloride salt

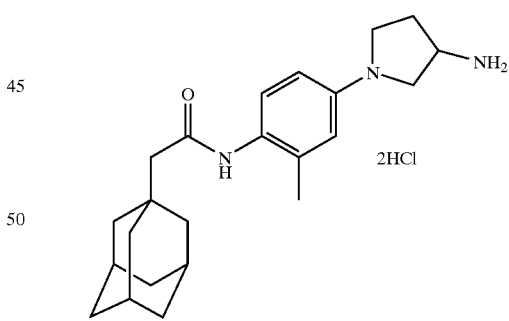

a) [1-(3-Methyl-4-nitrophenyl)-pyrrolidin-3-yl]-carbamic acid tert-butyl ester

4-Fluoro-2-methyl-1-nitrobenzene (1 g), pyrrolidin-3-ylcarbamic acid tert-butyl ester (1.2 g), potassium carbonate (1.79 g) and dimethyl sulfoxide (10 ml) were heated together at 80° C. under nitrogen for 15 h. The mixture was then cooled, diluted with ethyl acetate (200 ml), washed with 2N aqueous hydrochloric acid (200 ml), dried (MgSO₄) then concentrated. Purification of the residue by silica gel chromatography (eluting with 20% ethyl acetate in isohexane) gave the subtitle compound (1.744 g).

<sup>1</sup>H NMR (DMSO-d6) δ 8.03–8.00 (1H, d), 7.28–7.21 (1H, br d), 6.51–6.47 (2H, m), 4.20–4.12 (1H, br m), 3.61–3.16 (4H, m), 2.56 (3H, s), 2.20–2.08 (1H, m), 1.98–1.85 (1H, m), 1.39 (9H, s).

b) [1-(4-Amino-3-methylphenyl)-pyrrolidin-3-yl]-carbamic acid tert-butyl ester

[1-(3-Methyl-4-nitrophenyl)-pyrrolidin-3-yl]-carbamic acid tert-butyl ester (1.744 g, Example 35a), iron powder (1.52 g), ammonium chloride (1.45 g), ethanol (50 ml) and water (50 ml) were refluxed together under nitrogen for 2 h. The mixture was cooled and the iron was filtered off. Water (200 ml) was added to the residue and the product extracted into ethyl acetate (3×200 ml), dried (MgSO$_4$), and concentrated to give the subtitle compound (1.56 g).

$^1$H NMR (CDCl$_3$) 6.65 (1H, br s), 6.38 (2H, br m), 4.80 (1H, m), 4.33 (2H, br m), 3.60–2.80 (5H, m), 2.31–2.17 (4H, m), 1.92–1.82 (1H, m), 1.45 (9H, br s).

c) {1-[4-(2-(tricyclo[3.3.1.1$^{3,7}$]dec-1-yl)acetylamino)-3-methylphenyl]-pyrrolidin-3-yl}-carbamic acid tert-butyl ester To a solution of adamantan-1-yl-acetic acid (0.46 g) in dichloromethane (10 ml) at 0° C. was added dimethylformamide (0.1 ml) followed by oxalyl chloride (2.50 ml). The reaction was allowed to warm to room temperature and stirred for 30 min. The volatiles were removed under vacuum and the residue dried under high vacuum. The residue was dissolved in dichloromethane (10 ml) and added to a solution of [1-(4-amino-3-methylphenyl)-pyrrolidin-3-yl]-carbamic acid tert-butyl ester (0.70 g, Example 35b) in dichloromethane (10 ml) and triethylamine (0.8 ml) at 0° C. The reaction was allowed to warm to room temperature and stirred for 3 h. The solution was washed with 2N aqueous hydrochloric acid (20 ml), then brine (20 ml) and the organic layer dried over magnesium sulfate then filtered. The filtrate was concentrated under reduced pressure. The crude material was purified by silica gel chromatography (eluting with 1% methanol in dichloromethane) to yield the subtitle compound(1.1 g).

MS (APCI+ve) MW 468 (M+H)+

$^1$H NMR (DMSO-d6) δ 8.86 (1H, s); 7.01–6.98 (1H, d); 7.18–7.14 (1H, br d); 6.33–6.27 (3H, m); 4.15–4.04 (1H, m); 3.42–3.15 (3H, m); 3.00–2.97 (1H, m); 2.12 (3H, s); 2.00 (2H, s); 1.99–1.80 (5H, m); 1.70–1.61 (12H, m); 1.39 (9H, s).

d) N-[4-(3-Aminopyrrolidin-1-yl)-2-methylphenyl]-2-(tricyclo[3.3.1.1$^{3,7}$]dec-1-yl)acetamide, dihydrochloride salt {1-[4-(2-(tricyclo[3.3.1.1$^{3,7}$]dec-1-yl)acetylamino)-3-methylphenyl]-pyrrolidin-3-yl}-carbamic acid tert-butyl ester (0.20 g, Example 35c) was dissolved in methanol (5 ml) and hydrochloric acid (0.5 ml of a 4N solution in dioxane) was added. After stirring at room temperature for 14 h, the mixture was evaporated to 2/3 original volume under reduced pressure. Diethyl ether was gradually added to the solution and the resulting precipitate collected by filtration, washed with diethyl ether and dried in vacuo to afford the title compound as a solid (0.15 g)

MS (APCI+ve) 368 (M+H)+

$^1$H NMR (DMSO-d6) δ 8.92 (1H, s); 8.21 (2H,br s); 7.07–7.04 (1H, d); 6.41–6.35 (2H, m); 3.91 (1H, br m); 3.50–3.39 (2H, m); 3.29–3.20 (2H, m); 2.37–2.27 (2H, m); 2.14 (3H, s); 2.02 (2H, s); 1.94 (3H, s); 1.70–1.58 (12H, m).

EXAMPLE 36

N-(2-Methyl-4-piperazin-1-ylphenyl)-2-(tricyclo[3.3.1.1$^{3,7}$]dec-1-yl)acetamide, dihydrochloride salt

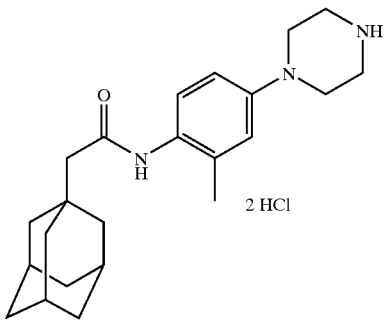

a) 4-(3-Methyl-4-nitrophenyl)piperazine-1-carboxylic acid tert-butyl ester

4-Fluoro-2-methyl-1-nitrobenzene (2 g), piperazine-1-carboxylic acid tert-butyl ester (4.8 g), potassium carbonate (3.57 g) and dimethyl sulfoxide (20 ml) were heated together at 80 ° C. under nitrogen for 15 h. The mixture was then cooled, diluted with ethyl acetate (200 ml), washed with 2N aqueous hydrochloric acid (200 ml), dried (MgSO$_4$), and concentrated to give the subtitle compound (4.10 g).

MS (APCI+ve) 321 (M)+

$^1$H NMR (DMSO-d6) δ 8.02–7.98 (1H, d), 6.89–6.86 (2H, m), 3.45 (8H, s), 2.55 (3H, s), 1.42 (9H, s).

b) 4-(4-Amino-3-methylphenyl)piperazine-1-carboxylic acid tert-butyl ester 4-(3-Methyl-4-nitrophenyl)piperazine-1-carboxylic acid tert-butyl ester (2 g, Example 36a), iron powder (1.74 g), ammonium chloride (1.67 g), ethanol (50 ml) and water (50 ml) were refluxed together under nitrogen for 2 h. The mixture was cooled and the iron was filtered off. Water (200 ml) was added to the residue and the product extracted into ethyl acetate (3×200 ml), dried (MgSO$_4$), and concentrated to give the subtitle compound (1.22 g).

$^1$H NMR (DMSO-d6) δ 6.62–6.52 (3H, m), 4.38 (2H, s), 3.41 (4H, br s), 2.83 (4H, br s), 2.02 (3H, s), 1.41 (9H, s).

c) 4-[4-(2-(tricyclo[3.3.1.1$^{3,7}$]dec-1-yl)acetylamino)-3-methylphenyl]-piperazine-1carboxylic acid tert-butyl ester To a solution of adamantan-l-yl-acetic acid (0.40 g) in dichloromethane (10 ml) at 0° C. was added dimethylformamide (0.1 ml) followed by oxalyl chloride (2.00 ml). The reaction was allowed to warm to room temperature and stirred for 30 min. The volatiles were removed under vacuum and the residue dried under high vacuum. The residue was dissolved in dichloromethane (10 ml) and added to a solution of 4-(4-amino-3-methylphenyl)piperazine-1-carboxylic acid tert-butyl ester (0.60 g, Example 36b) in dichloromethane (10 ml) and triethylamine (0.7 ml) at 0° C. The reaction was allowed to warm to room temperature and stirred for 3 h. The solution was washed with 2N aqueous hydrochloric acid (20 ml), then brine (20 ml) and the organic layer dried over magnesium sulfate then filtered. The filtrate was concentrated under reduced pressure. The crude material was was purified by silica gel chromatography (eluting with 1% methanol in dichloromethane) to yield the subtitle compound(0.42 g).

MS (APCI+ve) MW 468 (M+H)+

$^1$H NMR (DMSO-d6) δ 8.96 (1H, s); 7.14–7.11 (1H, d); 6.79–6.72 (2H, m); 3.47–3.40 (4H, m); 3.20–3.00 (4H, m); 2.14 (3H, s); 2.03 (2H, s); 1.94 (3H, br s); 1.70–1.56 (12H, m); 1.42 (9H, s).

d) N-(2-Methyl-4-piperazin-1-ylphenyl)-2-(tricyclo[3.3.1.1$^{3,7}$]dec-1-yl)acetamide, dihydrochloride salt 4-[4-(2-(tricyclo[3.3.1.1$^{3,7}$]dec-1-yl)acetylamino)-3-methylphenyl]-piperazine-1-carboxylic acid tert-butyl ester (0.05 g, Example 36c) was dissolved in methanol (2 ml) and hydrochloric acid (0.5 ml of a 4N solution in dioxane) was added. After stirring at room temperature for 14 h, the mixture was evaporated to 2/3 original volume under reduced pressure. Diethyl ether was gradually added to the solution and the resulting precipitate collected by filtration, washed with diethyl ether and dried in vacuo to afford the title compound as a solid (0.043 g)

MS (APCI+ve) 368 (M+H)+

$^1$H NMR (DMSO-d6) δ 9.01 (3H, br s); 7.18–7.15 (1H, d); 6.84–6.82 (1H, d); 6.79–6.76 (1H, dd); 3.31–3.29 (4H, m); 3.28–3.16 (4H, m); 2.16 (3H, s); 2.04 (2H, s); 1.94 (3H, br s); 1.69–1.58 (12H, m).

EXAMPLE 37 cis-4-(3-Amino-cyclopentyloxy)-2-chloro-N-(tricyclo[3.3.1.1$^{3,7}$]dec-1-ylmethyl)-benzamide, hydrochloride salt

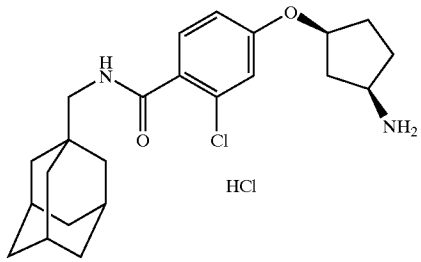

a) 2-Chloro-4-hydroxy-N-(tricyclo[3.3.1.1$^{3,7}$]dec-1-ylmethyl)-benzamide

To a solution of 2-chloro-4-hydroxybenzoic acid (3.30 g) in dimethylformamide (20 ml) was added 1,1'-carbonyldiimidazole (3.30 g). The reaction mixture was stirred for 2.5 h and then 1-adamantanethylamine (3.4 ml) was added. After 14 h the reaction mixture was partitioned between ethyl acetate and 2N aqueous hydrochloric acid and the organic layer was separated, washed with water then brine and dried (MgSO$_4$). The organic layer was concentrated under reduced pressure to give a residue which was purified by silica gel chromatography (eluting with 10–70% ethyl acetate in dichloromethane) to yield a white solid which was triturated with ethyl acetate to yield the subtitle compound as a white solid (3.6 g).

MS (APCI+ve) 320/322 (M+H)+

$^1$H NMR (DMSO-d6) δ 10.12 (1H, s), 8.10–8.06 (1H, t), 7.27–7.24 (1H, d), 6.81 (1H, d), 6.77–6.73 (1H, dd), 2.91–2.88 (2H,d), 1.93 (3H, br s), 1.69–1.56 (6H, br q), 1.50 (6H, br s).

b) cis-4-(3-Amino-cyclopentyloxy)-2-chloro-N-(tricyclo[3.3.1.1$^{3,7}$]dec-1-ylmethyl)-benzamide, hydrochloride salt To a solution of 2-chloro-4-hydroxy-N-(tricyclo[3.3.1.1$^{3,7}$]dec-1-methyl)-benzamide (0.20 g, Example 37a), trans-(3-hydroxycyclopentyl)-carbamic acid, tert-butyl ester (0.19 g) and tributylphosphine (0.23 ml) in dry tetrahydrofuran (6 ml) was added 1-[[(1-piperidinylcarbonyl)azo]carbonyl]-piperidine (0.24 g). The orange solution was heated at 60° C. under a nitrogen atmosphere for 2 h. Additional trans-(3-hydroxycyclopentyl)-carbamic acid, tert-butyl ester (0.19 g), tributylphosphine (0.23 ml) and 1-[[(1-piperidinylcarbonyl)azo]carbonyl]-piperidine (0.24 g) were added. Heating was continued and the process described above repeated until reaction was judged complete as judged by LC/MS. The cooled reaction mixture was diluted with diethyl ether then filtered. The filtrate was concentrated and purified by chromatography on silica gel (25–33% ethyl acetate/hexane) to give the t-butyloxycarbonyl (BOC)-protected compound as a colourless foam. The foam was dissolved in methanol (5 ml) and 4N hydrochloric acid in dioxane (0.25 ml) added. The solution was stirred at room temperature under a nitrogen atmosphere until the reaction was complete as judged by LC/MS. Evaporation of solvent followed by trituration with diethyl ether gave the title compound as a colourless solid (0.24 g).

MS (APCI+ve) 403/405 (M+H)+

$^1$H NMR (DMSO-d6) δ 8.18 (1H, t); 7.96 (2H, br s); 7.37–7.34 (1H, d); 7.05 (1H, m); 6.97–6.94 (1H, m); 4.87 (1H, br m); 3.72–3.40 (2H, m); 2.93–2.90 (2H, d); 2.04–1.51 (19H, m); 1.22 (2H, m).

EXAMPLE 38

2-Chloro-4-(4-piperidinyloxy)-N-(tricyclo[3.3.1.1$^{3,7}$]dec-1-ylmethyl)-benzamide, hydrochloride salt

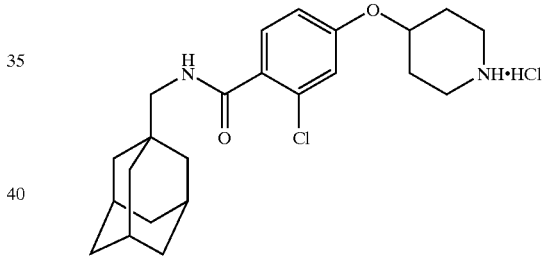

To a solution of 2-chloro-4-hydroxy-N-(tricyclo[3.3.1.1$^{3,7}$]dec-1-methyl)-benzamide (0.20 g, Example 37a), 4-hydroxy-1-piperidinecarboxylic acid, 1,1-dimethylethyl ester (0.19 g) and tributylphosphine (0.25 ml) in dry tetrahydrofuran (6 ml) was added 1-[[(1-piperidinylcarbonyl)azo]carbonyl]-piperidine (0.24 g). The orange solution was heated at 50° C. under a nitrogen atmosphere for 2 h. Additional 4-hydroxy-1-piperidinecarboxylic acid, 1,1-dimethylethyl ester (0.19 g), tributylphosphine (0.25 ml) and 1-[[(1-piperidinylcarbonyl)azo]carbonyl]-piperidine (0.24 g) were added. Heating was continued and the process described above repeated until reaction was complete as judged by LC/MS. The cooled reaction mixture was diluted with diethyl ether then filtered. The filtrate was concentrated and purified by chromatography on silica gel (3:1 iso-hexane/ethyl acetate) to give the the t-butyloxycarbonyl (BOC)-protected compound as a colourless foam. The foam was dissolved in methanol (10 ml) and 4N hydrochloric acid in dioxane (10 ml) added. The solution was stirred at room temperature under a nitrogen atmosphere until the reaction was complete as judged by LC/MS. Evaporation of solvent followed by trituration with diethyl ether gave the title compound as a colourless solid (0.165 g).

MS (APCI+ve) 403 (M+H)+

¹H NMR (DMSO-d6) δ 8.80 (2H, bs); 8.21–8.16 (1H, t); 7.37–7.34 (1H, d); 7.16(1H, m); 7.03–6.99 (1H, m); 4.80–4.68 (1H, m); 3.25–3.18 (2H, m); 3.17–3.01 (2H, m); 2.93–2.90 (2H, d); 2.17–2.02 (2H, m); 1.93 (3H, bs); 1.87–1.73 (2H, m); 1.69–1.57 (6H, AB); 1.51 (6H, s)

EXAMPLE 39

(+/−)-2-Chloro-4-(pyrrolidin-3-yloxy)-N-(tricyclo[3.3.1.1$^{3,7}$]dec-1-ylmethyl)-benzamide

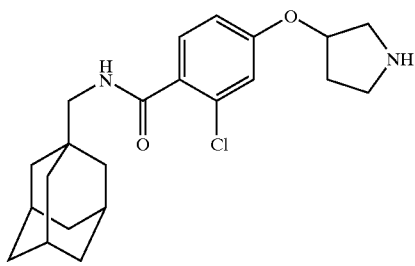

Prepared as described in Example 38 from 2-chloro-4-hydroxy-N-(tricyclo[3.3.1.1$^{3,7}$]dec-1-methyl)-benzamide (0.20 g, Example 37a), (+/−)-3-hydroxy-1-pyrrolidinecarboxylic acid, 1,1-dimethylethyl ester (0.18 g), tributylphosphine (0.25 ml), dry tetrahydrofuran (6 ml) and 1-[[(1-piperidinylcarbonyl)azo]carbonyl]-piperidine (0.24 g) to obtain the the t-butyloxycarbonyl (BOC)-protected compound. This compound was treated with 4N hydrochloric acid in dioxane (10 ml) and methanol (10 ml) to yield the title compound as colouless solid (0.165 g).

MS (APCI+ve) 389 (M+H)+

¹H NMR (DMSO-d6) δ 8.19–8.15 (1H, t); 7.35–7.32 (1H, d); 6.99 (1H, m); 6.93–6.90 (1H, m); 4.94–4.89 (1H, m); 3.24 (1H, s); 3.08–3.02 (1H, dd); 2.92–2.90 (2H, d); 2.88–2.72 (3H, m); 2.08–1.98 (1H, m); 1.93 (3H, s); 1.76–1.57 (7H, m); 1.51(6H, s).

EXAMPLE 40

2-Chloro-4-(piperidin-3-yloxy)-N-(tricyclo[3.3.1.1$^{3,7}$]dec-1-ylmethyl)-benzamide, hydrochloride salt

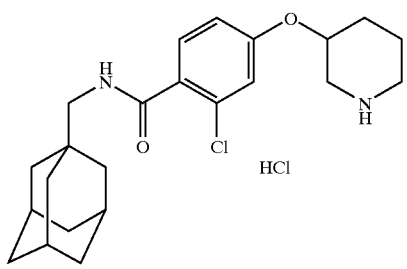

To a solution of 2-chloro-4-hydroxy-N-(tricyclo[3.3.1.1$^{3,7}$]dec-1-ylmethyl)-benzamide (0.20 g, Example 37a), 3-hydroxy-piperidine-1-carboxylic acid, tert-butyl ester (0.189 g) and tributylphosphine (0.23 ml) in dry tetrahydrofuran (6 ml) was added 1-[[(1-piperidinylcarbonyl)azo]carbonyl]-piperidine (0.24 g). The orange solution was heated at 60° C. under a nitrogen atmosphere for 2 h. Additional 3-hydroxy-piperidine-1-carboxylic acid, tert-butyl ester (0.19 g), tributylphosphine (0.23 ml) and 1-[[(1-piperidinylcarbonyl)azo]carbonyl]-piperidine (0.24 g) were added. Heating was continued and the process described above repeated until reaction was complete as judged by LC/MS. The cooled reaction mixture was diluted with diethyl ether then filtered. The filtrate was concentrated and purified by chromatography on silica gel (25% ethyl acetate: iso-hexane) followed by normal phase HPLC (0–1% ethanol in dichloromethane) to give the t-butyloxycarbonyl (BOC)-protected compound as a colourless foam. The foam was dissolved in methanol (5 ml) and 4N hydrochloric acid in dioxane (0.25 ml) added. The solution was stirred at room temperature under a nitrogen atmosphere until the reaction was complete as judged by LC/MS. Evaporation of solvent followed by trituration with diethyl ether gave the title compound as a colourless solid (0.006 g).

MS (APCI+ve) 403/405 (M+H)+

¹H NMR (DMSO-d6) δ 8.84 (2H, br s), 8.21 (1H, t); 7.38 (1H, d); 7.18 (1H, s); 7.05 (1H, dd); 4.82 (1H, br s); 3.24 (1H, d); 3.20 (1H, dd); 3.06 (2H, br s); 2.92 (2H, d); 1.94–1.51 (19H, m).

EXAMPLE 41

2-Chloro-4-(4-piperazin-1-yl)-N-(tricyclo[3.3.1.1$^{3,7}$]dec-1-ylmethyl)-benzamide, hydrochloride salt

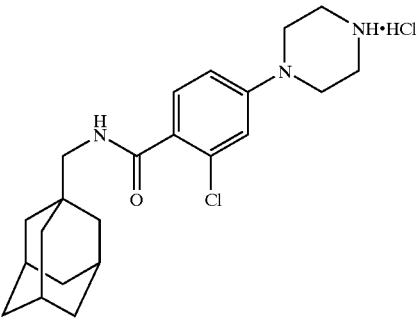

a) 4-Bromo-2-chloro-N-(tricyclo[3.3.1.1$^{3,7}$]dec-1-ylmethyl)-benzamide

To a suspension of 4-bromo-2-chlorobenzoic acid (5.00 g) in dichloromethane (25 ml) at 0° C. was added oxalyl chloride (3.7 ml) and dimethylformamide (5 drops). The resulting mixture was stirred at room temperature under a nitrogen atmosphere for 1 hour, then concentrated under reduced pressure to yield a solid. The solid was dissolved in dichloromethane (20 ml) and added dropwise to a solution of 1-adamantanemethylamine (3.36 g) and N,N-diisopropylethylamine (5.55 ml) in dichloromethane (20 ml). The resulting solution was allowed to stir at room temperature under a nitrogen atmosphere for 20 h. The reaction mixture was diluted with dichloromethane and washed with water, 10% aqueous potassium carbonate, 10% aqueous potassium hydrogen sulfate and saturated brine. The organic phase was then dried over sodium sulfate, filtered and concentrated under reduced pressure to afford the subtitle compound as a solid (4.28 g).

MS (APCI+ve) 382/384 (M+H)+

¹H NMR (DMSO-d6) δ 8.39–8.34 (1H, t); 7.78 (1H, m); 7.62–7.59 (1H, m); 7.37–7.34 (1H, d), 2.94–2.92 (2H, d); 1.94 (3H, br s); 1.69–1.57 (6H, br AB); 1.52 (6H, s).

b) 2-Chloro-4-(4-piperazin-1-yl)-N-(tricyclo[3.3.1.1$^{3,7}$]dec-1-ylmethyl)-benzamide, hydrochloride salt To a suspension of the 4-bromo-2-chloro-N-(tricyclo[3.3.1.1$^{3,7}$]dec-1-ylmethyl)-benzamide (Example 41a, 0.30 g), piperazine-1-carboxylic acid, 1,1-dimethylethyl ester (0.18 g), cesium carbonate (0.36 g) and (R)-BINAP (0.036 g) in anhydrous toluene (3 ml) was added palladium (II) acetate (0.009 g) and the mixture heated at 100 ° C. for 14 h in a pressure vessel flushed with nitrogen. The cooled reaction mixture was evaporated under reduced pressure to give an oil which was purified by chromatography on silica gel (2:1/iso-hexane: ethyl acetate) to give the t-butyloxycarbonyl (BOC)-protected compound as a colourless foam. The foam was dissolved in methanol (15 ml) and 4N hydrochloric acid in is dioxane (15 ml) added. The solution was stirred at room temperature under a nitrogen atmosphere until the reaction was complete as judged by LCMS. Evaporation followed by trituration with diethyl ether and methanol yielded the title compound as an off-white solid/foam (0.161 g).

MS (APCI+ve) 388/390 (M+H)+

$^1$H NMR (DMSO-d6) δ 8.98 (2H, bs); 8.11–8.07 (1H, t); 7.33–7.31 (1H, d); 7.05 (1H, m); 6.99–6.95 (1H, m); 3.46–3.43 (4H, m); 3.20 (4H, bs); 1.94 (3H, bs); 1.69–157 (6H, b AB); 1.51 (6H, bs).

EXAMPLE 42

2-Chloro-4-(3-pyrrolidinylamino)-N-(tricyclo[3.3.1.1$^{3,7}$]dec-1-ylmethyl)-benzamide, hydrochloride salt

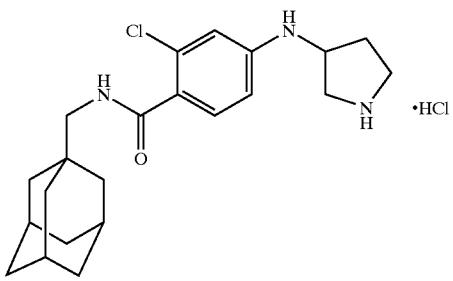

Prepared according to the method described in Example 41b from 4-bromo-2-chloro-N-(tricyclo[3.3.1.1$^{3,7}$]dec-1-ylmethyl)-benzamide (0.25 g, Example 41a), 3-amino-1-pyrrolidinecarboxylic acid, 1,1-dimethylethyl ester (0.182 g, Journal of Medicinal Chemistry, 1998, 41 (22), 4273–4278), cesium carbonate (0.347 g), (R)-(+)-2,2'-bis(diphenylphosphino)-1,1'-binaphthyl (0.036 g), palladium (II) acetate (0.009 g) and anhydrous toluene (3 ml). The residue was purified by HPLC eluting with a gradient of 0–5% ethanol in dichloromethane. The product was dissolved in methanol and stirred at room temperature for 3 h in the presence of 4N hydrochloric acid solution in dioxane (2 ml). The solution was concentrated under reduced pressure and triturated with diethyl ether to give the title compound as a white powder (0.057 g).

MS (APCI+ve) 388 (M+H–HCl)+

$^1$H NMR (CD$_3$OD) δ 7.33 (1H, d); 6.71 (1H, d); 6.63 (1H, dd); 4.27–4.21 (1H, m); 3.57–3.40 (3H, m); 3.23 (1H, dd); 3.05 (2H, s); 2.43–2.33 (1H, m); 2.33–2.01 (1H, m); 1.99 (3H, bs); 1.73 (6H, q); 1.62 (6H, d).

EXAMPLE 43

2-Chloro-4-(hexahydro-1H-1,4-diazepin-1-yl)-N-(tricyclo[3.3.1.1$^{3,7}$]dec-1-ylmethyl)-benzamide, hydrochloride salt

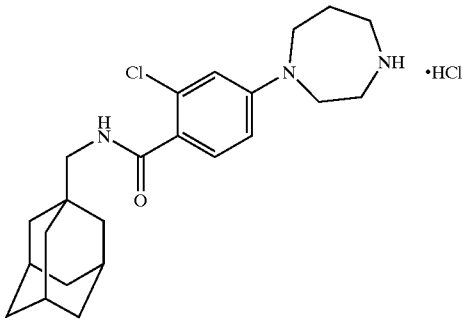

Prepared according to the method described in Example 41b from 4-bromo-2-chloro-N-(tricyclo[3.3.1.1$^{3,7}$]dec-1-ylmethyl)-benzamide (0.25 g, Example 41a), hexahydro-1H-1,4-diazepine-1-carboxylic acid, 1,1-dimethylethyl ester (0.182 g), cesium carbonate (0.347 g), (R)-(+)-2,2'-bis(diphenylphosphino)-1,1'-binaphthyl (0.036 g), palladium (II) acetate (0.009 g) and anhydrous toluene (3 ml). The residue was purified by HPLC eluting with a gradient of 0–5% ethanol in dichloromethane. The product was dissolved in methanol and stirred at room temperature for 3 h in presence of 4N hydrochloric acid solution in dioxane (2 ml). The solution was concentrated under reduced pressure and triturated with diethyl ether to give the title compound as a white powder (0.17 g).

MS (APCI+ve) 402 (M+H–HCl)+

$^1$H NMR (CD$_3$OD) δ 7.41 (1H, d); 6.88 (1H, d); 6.81 (1H, dd); 3.83 (2H, t); 3.63 (2H, t); 3.40 (2H, t); 3.30 (2H, t); 3.06 (2H, s); 2.24–2.16 (2H, m); 1.99 (3H, bs); 1.74 (6H, q); 1.63 (6H, d). p According to the procedure described in Example 8, the following compounds were prepared:

EXAMPLE 44

(±)-5-[(3-Amino-1-piperidinyl)methyl]-2-chloro-N-(tricyclo[3.3.1.1$^{3,7}$]dec-1-ylmethyl)-benzamide, hydrocloride salt

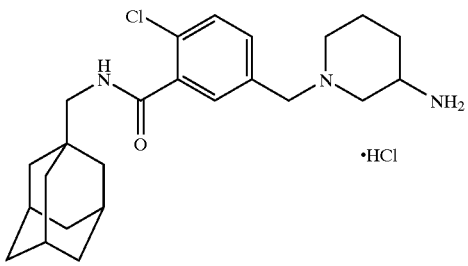

MS (APCI+ve) MW 416/418 (M+H)+

$^1$H NMR (CD$_3$OD) δ 7.70 (1H, bs); 7.67 (1H, dd); 7.60 (1H, d); 4.49 (1H, d); 4.45 (1H, d); 3.73–3.58 (2H, m); 3.57–3.45 (1H, m); 3.14–2.95 (4H, m); 2.25–2.04 (2H, m); 1.98 (4H, bs); 1.76 (3H, d); 1.73–1.58 (1H, m); 1.70 (3H, d); 1.63 (6H, bs).

EXAMPLE 45

2-Chloro-5-(2,5-diazabicyclo[2.2.1]hept-2-ylmethyl)-N-(tricyclo[3.3.1.1$^{3,7}$]dec-1-ylmethyl)-benzamide, hydrochloride salt

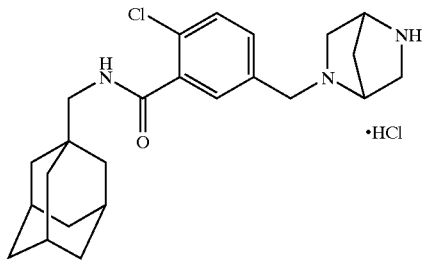

MS (APCI+ve) MW 414/416 (M+H)+

$^1$H NMR (CD$_3$OD) δ 7.74 (1H, d); 7.72 (1H, dd); 7.60 (1H, d); 4.70–4.55 (3H, m); 4.45 (1H, d); 4.00 (1H, d); 3.73 (1H, d); 3.60–3.50 (2H, m); 3.07 (2H, s); 2.71 (1H, d); 2.27 (1H, d); 1.98 (3H, bs); 1.77 (3H, d); 1.69 (3H, d); 1.63 (6H, bs).

EXAMPLE 46

2-Chloro-5-(9-oxa-3,7-diazabicyclo[3.3.1]non-3-ylmethyl)-N-(tricyclo[3.3.1.1$^{3,7}$]dec-1-ylmethyl)-benzamide, hydrochloride salt

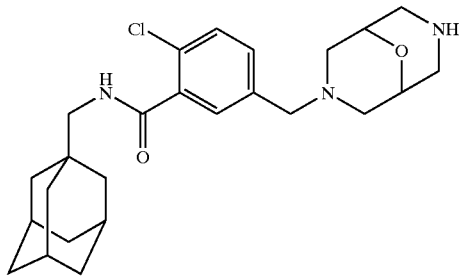

MS (APCI+ve) MW 442/446 (M+H)+

$^1$H NMR (CD$_3$OD) δ 7.60–7.40 (3H, m); 4.25–4.00 (2H, m); 3.70–3.40 (2H, m); 3.46 (4H, m); 3.07 (2H, s); 3.15–2.90 (2H, m); 2.80–2.50 (2H, m); 2.00 (3H, bs); 1.78 (3H, d); 1.71 (3H, d); 1.63 (6H, bs).

EXAMPLE 47

2-Chloro-5-(3,7-diazabicyclo[3.3.1]non-3-ylmethyl)-N-(tricyclo[3.3.1.1$^{3,7}$]dec-1-ylmethyl)-benzamide, hydrochloride salt

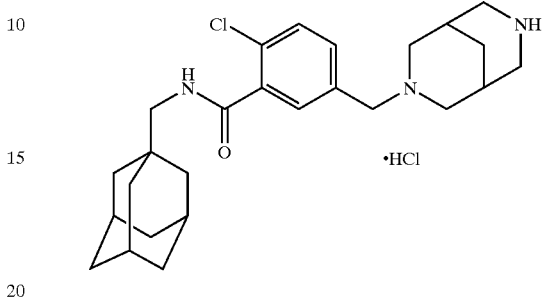

MS (APCI+ve) MW 442/444 (M+H)+

$^1$H NMR (CD$_3$OD) δ 7.91 (1H, s); 7.78 (1H, d); 7.56 (1H, d); 7.46 (1H, bs); 4.44 (2H, bs); 3.65–3.28 (8H, m); 3.08 (2H, bs); 2.48 (2H, bs); 2.05–1.90 (5H, m); 1.77 (3H, d); 1.71 (3H, d); 1.64 (6H, bs).

EXAMPLE 48 trans-2-Chloro-5-[[8-(methylamino)-3-azabicyclo[3.2.1]oct-3-yl]methyl]-N-(tricyclo[3.3.1.1$^{3,7}$]dec-1-ylmethyl)-benzamide, hydrochloride salt

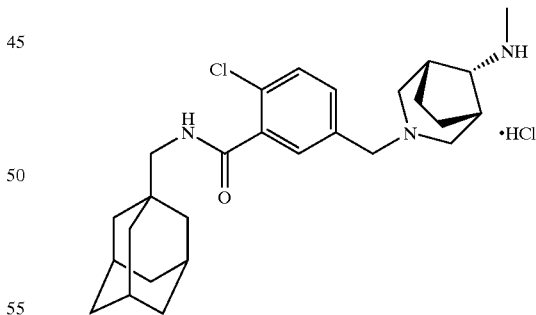

MS (APCI+ve) MW 456/458 (M+H)+

$^1$H NMR (CD$_3$OD) δ 7.79 (1H, d); 7.77 (1H, dd); 7.58 (1H, d); 4.71 (2H, bs); 3.80 (2H, d); 3.40 (1H, t); 3.25 (2H, dd); 3.07 (2H, s); 2.86 (3H, s); 2.70 (2H, bs); 2.10–1.90 (7H, m); 1.77 (3H, d); 1.70 (3H, d); 1.63 (6H, bs).

EXAMPLE 49 cis-2-Chloro-5-[(hexahydropyrrolo[3,4-c]pyrrol-2(1H)-yl)methyl]-N-(tricyclo[3.3.1.1$^{3,7}$]dec-1-ylmethyl)-benzamide, hydrochloride salt

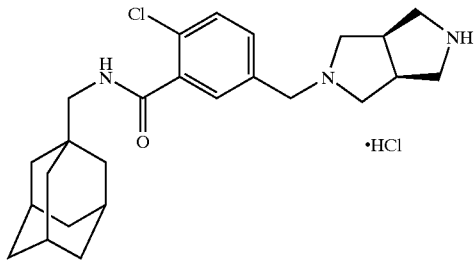

MS (APCI+ve) MW 428/430 (M+H)+

$^1$H NMR (DMSO-d6) δ 8.00 (1H, t); 7.65 (1H, s); 7.63 (1H, d); 7.52 (1H, d); 4.34 (2H, bs); 3.60–3.05 (10H, m); 2.97 (2H, d); 1.95 (3H, bs); 1.70 (3H, d); 1.63 (3H, d); 1.57 (6H, s).

EXAMPLE 50

2-Chloro-5-(4-piperidinylidenemethyl)-N-(tricyclo[3.3.1.1$^{3,7}$]dec-1-ylmethyl)-benzamide, hydrochloride salt

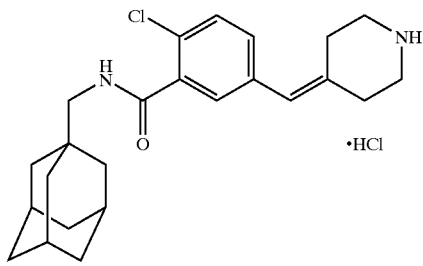

a) [[4-chloro-3-[[(tricyclo[3.3.1.1$^{3,7}$]dec-1-ylmethyl)amino]carbonyl]phenyl]-methyl]phosphonic acid, dimethyl ester 5-Bromomethyl-2-chloro-N-(tricyclo[3.3.1.1$^{3,7}$]dec-1-ylmethyl)-benzamide (5.70 g, Example 8b) in 100 ml of trimethylphosphite was heated at reflux for 15 h. The solvent was removed by azeotropic distillation with toluene under high vacuum to afford the subtitle compound as a yellow solid.

MS (APCI+ve) MW 426/428 (M+H)+

$^1$H NMR (DMSO-d6) δ 8.34 (1H, t); 7.42 (1H, d); 7.35–7.27 (2H, m); 3.63 (3H, s); 3.58 (3H, s); 3.42 (2H, d); 2.92 (2H, d); 1.94 (3H, bs); 1.67 (3H, d); 1.59 (3H, d); 1.52 (6H, bs).

b) 4-[[4-chloro-3-[[(tricyclo[3.3.1.1$^{3,7}$]dec-1-ylmethyl)amino]carbonyl]phenyl]methylene]-1-piperidinecarboxylic acid, 1,1-dimethylethyl ester To a solution of the crude [[4-chloro-3-[[(tricyclo[3.3.1.1$^{3,7}$]dec-1-ylmethyl)amino]carbonyl]phenyl]methyl]phosphonic acid, dimethyl ester (2.50 g, Example 50a) in tetrahydrofuran (50 ml) at −78 ° C. was added a solution of lithium diisopropylamide (7.30 ml, 2M in tetrahydrofuran). The reaction was allowed to warm to room temperature and stirred for 15 min. N-t-butoxycarbonylpiperidin-4-one (1.52 g) in tetrahydrofuran (5 ml) was then added and the mixture stirred for 24 h. The reaction was diluted with water and extracted with ethylacetate. The organic layer was washed with brine and dried over magnesium sulfate. The crude material was purified on a silica gel (0 to 5% methanol in dichloromethane) to afford the subtitle compound as a white foam.

MS (APCI+ve) MW 443/445 (M+H)+

$^1$H NMR (DMSO-d6) δ 7.52 (1H, d); 7.34 (1H, d); 7.16 (1H, dd); 6.30 (1H, s); 6.25 (t, 1H); 3.48 (2H, t); 3.40 (2H, t); 3.40 (2H, t); 3.18 (2H, d); 2.42 (t, 2H); 2.32 (t, 2H); 2.05 (3H, bs); 1.73 (3H, d); 1.64 (d, 3H), 1.59 (6H, s); 1.47 (9H, bs).

c) 2-Chloro-5-(4-piperidinylidenemethyl)-N-(tricyclo[3.3.1.1$^{3,7}$]dec-1-ylmethyl)-benzamide, hydrochloride salt A solution of 4-[[4-chloro-3-[[(tricyclo[3.3.1.1$^{3,7}$]dec-1-ylmethyl)amino]carbonyl]phenyl]methylene]-1-piperidinecarboxylic acid, 1,1-dimethylethyl ester (0.10 g, Example 50b) in methanol (3 ml) was treated with a 4N solution of hydrochloric acid in dioxane (1 ml) and stirred for 14 h at room temperature. The reaction mixture was concentrated under vacuum and the residue recrystallised from iso-propanol/ether to give the title compound as a white solid (0.071 g).

MS (APCI+ve) MW 399/401 (M+H)+

$^1$H NMR (DMSO-d6) δ 7.52 (1H, d); 7.34 (1H, d); 7.16 (1H, dd); 6.30 (1H, s); 6.25 (t, 1H); 3.48 (2H, t); 3.40 (2H, t); 3.40 (2H, t); 3.18 (2H, d); 2.42 (t, 2H); 2.32 (t, 2H); 2.05 (3H, bs); 1.73 (3H, d); 1.64 (d, 3H), 1.59 (6H, s); 1.47 (9H, bs).

EXAMPLE 51

2-Chloro-5-(4-piperidinylmethyl)-N-(tricyclo[3.3.1.1$^{3,7}$]dec-1-ylmethyl)-benzamide, hydrochloride salt

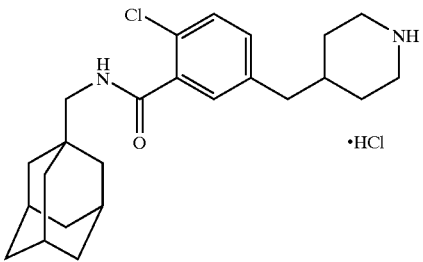

To a solution of 2-chloro-5-(4-piperidinylidenemethyl)-N-(tricyclo[3.3.1.1$^{3,7}$]dec-1-ylmethyl)-benzamide, hydrochloride salt (0.10 g, Example 50c) in ethanol (10 ml) was added platinum oxide (2 mg). The vessel was placed under 3 bars hydrogen pressure for 3 h. The catalyst was removed by filtration through a pad of Celite, washed with ethanol and the solution concentrated under vacuum. The crude material was recrystallised from iso-propanol to afford a white solid. The t-butoxycarbonyl protected compound was dissolved in methanol (10 ml) and treated with a solution of 4N HCl in dioxane (2 ml). The reaction was stirred for 14 h at room temperature, the volatiles removed under vacuum and the residue recrystallised from iso-propanol/ether to afford the hydrochloride salt as a white powder (0.065 g).

MS (APCI+ve) MW 402/404 (M+H)+

$^1$H NMR (CD$_3$OD) δ 8.38 (1H, t); 7.38 (1H, d); 7.30–7.20 (2H, m); 3.35 (2H, d); 3.05 (2H, d); 2.92 (2H, td); 2.63 (2H, d); 1.98 (3H, bs); 1.95–1.80 (1H, m); 1.85 (2H, d); 1.77 (3H, d); 1.68 (3H, d); 1.62 (6H, s); 1.40 (2H, q).

EXAMPLE 52

2-Chloro-5-(4-hydroxy-piperidin-4-yl)-N-(tricyclo[3.3.1.1$^{3,7}$]dec-1-ylmethyl)-benzamide, hydrochloride salt

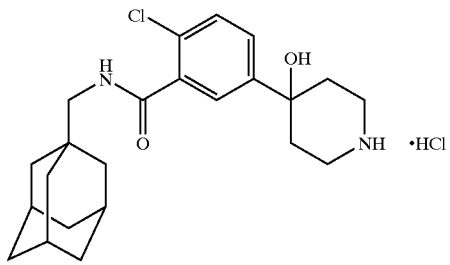

To a solution of 5-bromo-2-chloro-N-(tricyclo[3.3.1.1$^{3,7}$]dec-1-ylmethyl)-benzamide (0.30 g, Example 23a) in anhydrous tetrahydrofuran (10 ml) at −78 ° C. was added dropwise a solution of n-butyllithium in hexanes (2.5M, 0.72 ml). After 10 min. a solution of t-butoxycarbonyl4-piperidone (0.21 g) in tetrahydrofuran (2 ml) was added. The solution was stirred an additional 20 min. then treated with saturated aqueous ammonium chloride solution. The mixture was allowed to warm to room temperature then partitioned between ethyl acetate and saturated aqueous ammonium chloride solution. The organic extracts were dried over magnesium sulphate and concentrated in vacuo. The residue was chromatographed on silica (ethyl acetate: isohexane/1:4 to 1:2 gradient) to give the t-butoxycarbonyl protected product (0.153 g). This was redissolved in methanol (4 ml) and treated for 14 h with 4N HCl in dioxan (1 ml). The solution was partially concentrated in vacuo and the product precipitated with diethyl ether. The solution was filtered and the white solid washed with diethyl ether to give the title compound (0.091 g)

MS (APCI+ve) MW 403 (M+H)+

$^1$H NMR (CD$_3$OD) δ 8.43 (1H, m, br); 7.59 (1H, m); 7.55 (1H, d); 7.49 (1H, d); 3.52–3.30 (4H, m); 3.09 (2H, d); 2.23 (2H, m); 2.04–1.88 (5H, m); 1.95–1.80 (1H, m); 1.84–1.66 (6H, m); 1.65 (6H, d).

EXAMPLE 53

2-Chloro-5-(1,2,3,6-tetrahydro-pyridin4-yl)-N-(tricyclo[3.3.1.13,7]dec-1-ylmethyl)-benzamide, hydrochloride salt

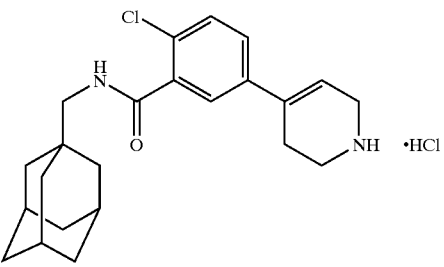

A solutuion of 2-chloro-5-(4-hydroxy-piperidin-4-yl)-N-(tricyclo[3.3.1.13$^{3,7}$]dec-1-ylmethyl)-benzamide, hydrochloride salt (0.25 g, Example 52) in concentrated hydrochloric acid (10 mn) was heated at 100° C. for 5 h. The solution was allowed to cool slowly. Colourless crystals separated. These were removed by filtration, washed with diethyl ether then acetonitrile and dried to afford the title compound (0.031 g).

MS (APCI+ve) MW 385 (M+H)+

$^1$H NMR (CD$_3$OD) δ 8.44 (1H, m, br); 7.55–7.45 (3H, m); 6.23 (1H, m); 3.85 (2H, m); 3.47 (2H, t); 3.07 (2H, d); 2.79 (2H, m); 1.98 (3H, m); 1.77 (3H, m); 1.69 (3H, m); 1.63 (6H, s,br).

EXAMPLE 54

2-Ethyl-5-piperazin-1-ylmethyl-N-(tricyclo[3.3.1.1$^{3,7}$]dec-1-ylmethyl)-benzamide, hydrochloride salt

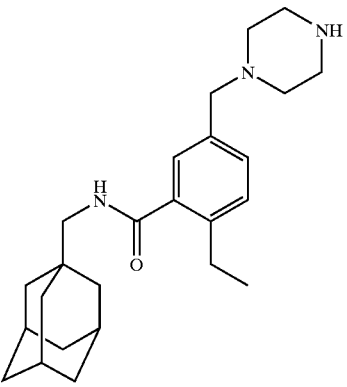

2-Bromo-5-(4-[{1,1-dimethylethyl}oxycarbonyl]-piperazin-1-yl)methyl-N-(tricyclo[3.3.1.1$^{3,7}$]dec-1-ylmethyl)-benzamide (Example 65b, 0.89 g) was dissolved in dry tetrahydrofuran. Sodium hydride (60% dispersion, 0.07 g) was added and the mixture stiired at room temperature for 5 min. The mixture was cooled to −70° C. under a nitrogen atmosphere and t-butyllithium (1.9 ml, 1.7M solution) added. After 5 min, ethyl iodide (0.5 ml) was added and the mixture stirred at −70° C. for 30 min. Aqueous ammonium chloride solution was added and the product extracted with diethyl ether, dried (MgSO$_4$) and concentrated in vacuo. Chromatography on silica gave the t-butyloxycarbonyl (BOC) protected compound as a foam. This was redissolved in methanol (5 ml) and 4N HCl in dioxane (1 ml) added. The mixture was stirred at room temperature for 14 h. The solution was partially concentrated under vacuum and the product precipitated with diethyl ether. The resulting solid was filtered and washed with ether to afford the title compound as a white powder (0.040 g).

$^1$H NMR (DMSO) δ 9.59 (2H, s, br); 8.15 (1H, t); 7.58 (2H, s, br); 7.35 (1H, d); 4.37 (2H; s, br); 3.49 (m); 3.25 (2H, m, br); 2.95 (2H, d); 2.72 (2H, q); 1.94 (3H; s, br); 1.69–1.59 (6H, m); 1.52 (6H, s); 1.165 (3H, t).

EXAMPLE 55

2-Chloro-5-(piperidin-4-ylsulfanyl)-N-(tricyclo[3.3.1.1$^{3,7}$]dec-1-ylmethyl)-benzamide, hydrochloride salt

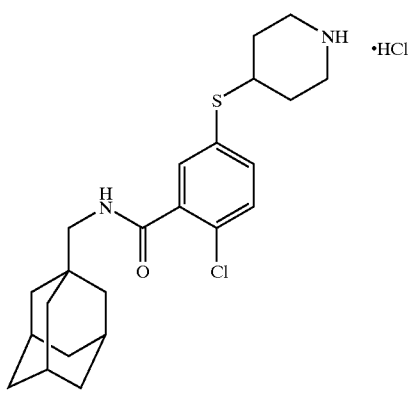

a) 4-(Toluene-4-sulfonylsulfanyl)-piperidine-1-carboxylic acid tert-butyl ester 4-Iodo-piperidine-1-carboxylic acid, tert-butyl ester (1.3 g) and potassium toluene-4-thiosulfonate (1.0 g) were combined in ethanol (10 ml) with cis-dicyclohexane 18-crown-6 (10 mg) and heated under reflux for 12 h. After cooling the reaction mixture was partitioned between ethyl acetate and water, the organic layer was separated, washed with water and brine, dried over magnesium sulfate and concentrated under reduced pressure. The residue was purified by silica gel chromatography (eluting with iso-hexane/ethyl acetate 4:1 to 7:3), to yield the subtitle compound as an oil (0.65 g).

MS (APCI+ve) 315 (M+H-tBu)+

$^1$H NMR (CDCl$_3$) δ 7.80–7.85 (2H, m), 7.30–7.40 (2H, m), 3.95–4.10 (1H, m), 3.75–3.85 (1H, m), 3.40–3.50 (1/2H, m), 3.10–3.20 (1/2H, m), 2.95–3.05 (1H, m), 2.80–2.90 (1H, m), 2.46 (3H, s), 1.90–2.10 (2H, m), 1.50–1.70 (2H, m), 1.43 & 1.45 (9H, pair s).

b) 2-Chloro-5-(4-[{1,1-dimethylethyl}oxycarbonyl]piperidine-4-ylsulfanyl)-N-(tricyclo[3.3.1.1$^{3,7}$]dec-1-ylmethyl)-benzamide To a solution of 5-bromo-2-chloro-N-(tricyclo[3.3.1.1$^{3,7}$]dec-1-ylmethyl)-benzamide (0.30 g, Example 23a) in anhydrous tetrahydrofuran (10 ml) at −78 ° C. was added dropwise a solution of n-butyllithium in hexanes (2.5M, 0.72 ml). After 10 min. a solution of 4-(toluene-4-sulfonylsulfanyl)-piperidine-1-carboxylic acid, tert-butyl ester (0.38 g, Example 55a) in tetrahydrofuran (7 ml) was added. After a further 1 hour at −78° C. the reaction mixture was warmed to ambient temperature and quenched by the addition of water (5 ml). The reaction mixture was diluted with ethyl acetate and washed twice with saturated aqueous sodium hydrogen carbonate solution, then with brine and dried over magnesium sulfate. The organic layer was concentrated under reduced pressure to give a residue which was purified by silica gel chromatography (eluting with 0–5% ethanol in dichloromethane) to yield the subtitle compound (0.20 g).

MS (APCI+ve) 419/21 (M+H−BOC)+ c) 2-Chloro-5-(piperidin-4-ylsulfanyl)-N-(tricyclo[3.3.1.1$^{3,7}$]dec-1-ylmethyl)-benzamide, hydrochloride salt 2-Chloro-5-(-(4-[{1,1-dimethylethyl}oxycarbonyl]-piperidin-4-ylsulfanyl)-N-(tricyclo[3.3.1.1$^{3,7}$]dec-1-ylmethyl)-benzamide (0.20 g, Example 55b) was dissolved in methanol (15 ml) and hydrochloric acid (1.0 ml of a 4N solution in dioxane) was added. After stirring at room temperature for 14 h, the reaction mixture was basified with saturated sodium hydrogen carbonate solution and extracted twice with dichloromethane. The organic layer was concentrated under reduced pressure to give a residue which was purified by silica gel chromatography (eluting with 0–100% methanol in dichloromethane). The residue was dissolved in dichloromethane (5 ml) and hydrochloric acid (1N in diethyl ether, 2 ml) added. Evaporation to dryness gave the title compound as the hydrochloride salt (0.050 g).

MS (APCI+ve) 419/21 (M+H)+

$^1$H NMR (DMSO-d6) δ 8.75 (2H, brd), 8.38 (1H, t), 7.48 (2H, s), 7.37 (1H, s), 3.50–3.60 (1H, m), 3.30 (2H, brd), 2.92–3.05 (4H, m), 2.06 (2H, brd), 1.94 (3H, s), 1.57–1.75 (8H, m), 1.52 (6H, s).

EXAMPLE 56

2-Chloro-5-(piperidin-4-ylsulfinyl)-N-(tricyclo[3.3.1.1$^{3,7}$]dec-1-ylmethyl)-benzamide

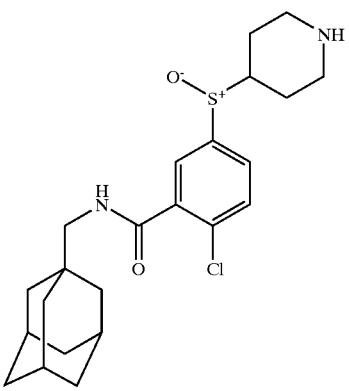

m-Chloroperoxybenzoic acid (166 mg) was added to a solution of 2-chloro-5-(piperidin-4-ylsulfanyl)-N-(tricyclo[3.3.1.1$^{3,7}$]dec-1-ylmethyl)-benzamide (0.35 g, Example 55c) in dichloromethane (5 ml). After 2 h calcium hydroxide (0.20 g) was added and 30 min. later the salts removed by filtration. The filtrate was concentrated under reduced pressure to give a residue which was purified by silica gel chromatography (eluting with 0–25% ethanol in dichloromethane). The residue was dissolved in methanol (5 ml) and hydrochloric acid (0.5 ml of a 4N solution in dioxane) was added. After stirring at room temperature for 14 h, the solution was concentrated under reduced pressure and triturated with diethyl ether to yield the title compound as the hydrochloride salt (0.030 g).

MS (APCI+ve) 435/37 (M+H)+

$^1$H NMR (DMSO-d6) δ 8.88 (1H, brs), 8.47 (2H, brt), 7.76 (1H, d), 7.67 (1H, dd), 7.61 (1H, d), 3.30–3.40 (2H, m), 3.13 (1H, t), 2.98 (2H, d), 2.80–2.90 (2H, m), 2.15 (1H, d), 1.95 (3H, m), 1.50–1.85 (15H, m).

EXAMPLE 57

2-Chloro-5-(piperidin-4-ylsulfonyl)-N-(tricyclo[3.3.1.1$^{3,7}$]dec1-ylmethyl)-benzamide, hydrochloride salt

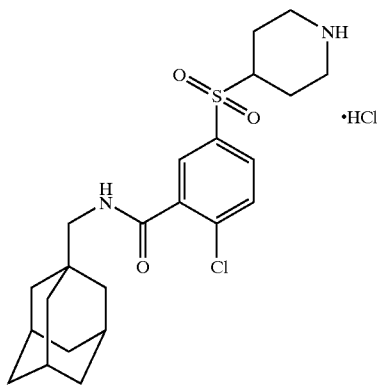

m-Chloroperoxybenzoic acid (0.30 g) was added to a solution of 2-chloro-5-(piperidin-4-ylsulfinyl)-N-(tricyclo[3.3.1.1$^{3,7}$]dec-1-ylmethyl)-benzamide (0.30 g) in dichloromethane (10 ml). After 2 h calcium hydroxide (170 mg) was added and 30 min. later the salts removed by filtration. The filtrate was concentrated under reduced pressure to give a residue which was purified by silica gel chromatography (eluting with 0–2% ethanol in dichloromethane). The residue was dissolved in methanol (5 ml) and hydrochloric acid (0.25 ml of a 4N solution in dioxane) was added. After stirring at room temperature for 14 h, the solution was concentrated under reduced pressure and triturated with diethyl ether to yield the title compound (0.03 g).

MS (APCI+ve) 451/53 (M+H)+

$^1$H NMR (DMSO-d6) δ 8.89 (1H, brs), 8.57 (1H, t), 8.50 (1H, brs), 7.87 (2H, ABq), 7.75 (1H, d), 3.71 (1H, td), 3.40 (2H, d), 3.00 (2H, d), 2.80–2.90 (2H, m), 1.95–2.05 (5H, m), 1.50–1.90 (14H, m).

EXAMPLE 58

2-Chloro-5-(piperidin-4-ylmethylsulfanyl)-N-(tricyclo[3.3.1.1$^{3,7}$]dec-1-ylmethyl)-benzamide, hydrochloride salt

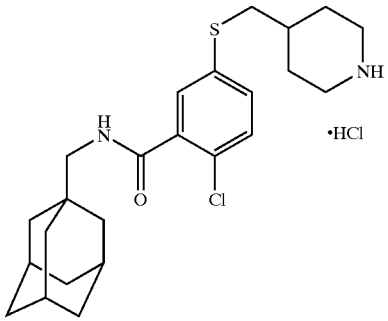

a) 2-Chloro-5-(4-[{1,1-dimethylethyl}oxycarbonyl]piperidin-4-ylmethylsulfanyl)-N-(tricyclo[3.3.1.1$^{3,7}$]dec-1-ylmethyl)-benzamide Trifluoroacetic acid anhydride (2 ml) was added to a solution of 2-chloro-5-methylsulphinyl-N-(tricyclo[3.3.1.1$^{3,7}$]dec-1-ylmethyl)-benzamide (0.53 g, Example 58a, WO 99/29661) in dichloromethane (10 ml) and heated under reflux for 1.5 h, cooled and concentrated. The resultant residue was dissolved in methanol (30 ml), allowed to stand for 1 hour then concentrated. The resultant residue was dissolved in acetone (10 ml) and potassium carbonate (0.60 g) and 4-iodomethyl-piperidine-1-carboxylic acid tert-butyl ester (0.94 g) was added. The reaction mixture was heated under reflux for 3 h, cooled and concentrated. The resultant residue was dissolved in ethyl acetate, washed twice with 10% w/w KHSO$_4$ solution, twice with saturated sodium hydrogen carbonate solution, once with brine and dried over magnesium sulfate. The organic layer was concentrated under reduced pressure to give a residue which was purified by silica gel chromatography (eluting with 0–2% ethanol in dichloromethane), to yield the subtitle compound (0.46 g).

MS (APCI+ve) 433/35 (M+H-BOC)+

$^1$H NMR (CDCl$_3$) δ 7.61 (1H, d), 7.25–7.31 (2H, m), 6.27 (1H, brt), 4.09 (2H, brd), 3.17 (2H, d), 2.86 (2H, d), 2.66 (2H, t), 2.01 (3H, s), 1.60–1.90 (15H, m), 1.45 (9H, s), 1.18 (2H, dq).

b) 2-Chloro-5-(piperidin-4-ylmethylsulfanyl)-N-(tricyclo[3.3.1.1$^{3,7}$]dec-1-ylmethyl)-benzamide, hydrochloride salt Hydrochloric acid (4N dioxane, 0.5 ml) was added to a solution of 2-chloro-5-(4-[{1,1-dimethylethyl}oxycarbonyl]piperidin-4-ylmethylsulfanyl)-N-(tricyclo[3.3.1.1$^{3,7}$]dec-1-ylmethyl)-benzamide (0.235 g, Example 58a) in methanol (10 ml). After 24 h the reaction mixture was concentrated, then triturated with ether to give the title compound (0.20 g).

MS (APCI+ve) 433/35 (M+H)+

$^1$H NMR (DMSO-d6) δ 8.76 (1H, brs), 8.48 (1H, brs), 8.35 (1H, t), 7.40 (2H, ABq), 7.28 (1H, d), 3.24 (2H, d), 3.00 (2H, d), 2.92 (2H, d), 2.84 (2H, q), 1.94 (5H, brs), 1.75–1.82 (1H, m), 1.65 (6H, q), 1.52 (6H, s), 1.40 (2H, q).

EXAMPLE 59

2-Chloro-5-(piperidin-4-ylmethanesulfonyl)-N-(tricyclo[3.3.1.1[3,7]]dec-1-ylmethyl)-benzamide, hydrochloride salt

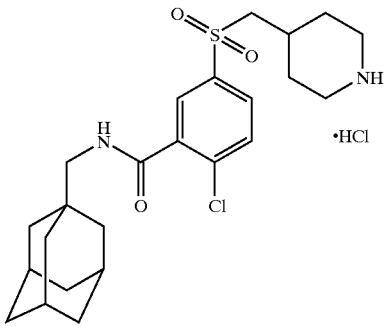

m-Chloroperoxybenzoic acid (0.19 g) was added to a solution 2-chloro-5-(4-[{1,1-dimethylethyl}oxycarbonyl]piperidin-4-ylmethylsulfanyl)-N-(tricyclo[3.3.1.1[3,7]]dec-1-ylmethyl)-benzamide (0.165 g, Example 58a) in chloroform (10 ml). After 5 h calcium hydroxide (120 mg) was added and 30 min. later the salts removed by filtration. The reaction mixture was concentrated, then dissolved in methanol (10 ml) and hydrochloric acid (1.0 ml of a 4N solution in dioxane) added. After stirring at room temperature for 14 h, concentration under reduced pressure yielded the title compound (0.075 g).

MS (APCI+ve) 465/67 (M+H)+

$^1$H NMR (DMSO-d6) δ 8.70 (1H, brs), 8.55 (1H, t), 8.48 (1H, brs), 7.95 (1H, dd), 7.88 (1H, d), 7.82 (1H, d), 3.47 (2H, d), 3.21 (2H, d), 2.97 (2H, d), 2.89 (2H, d), 2.10–2.25 (1H, m), 1.95 (5H, brs), 1.40–1.80 (14H, m).

EXAMPLE 60

2-Chloro-5-(piperazine-1-carbonyl)-N-(tricyclo[3.3.1.1[3,7]]dec-1-ylmethyl)-benzamide, hydrochloride salt

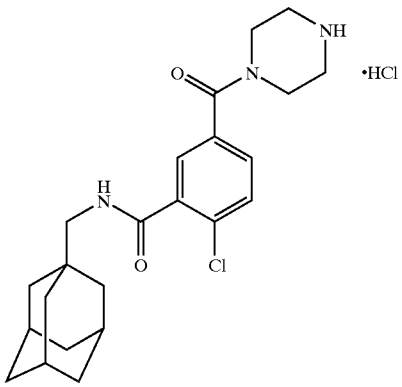

a) 4-Chloro-N-(tricyclo[3.3.1.1[3,7]]dec-1-ylmethyl)-isophthalamic acid n-Butyllithium (3 ml, 2M hexanes) was added at −78° C. to a solution of 5-bromo-2-chloro-N-(tricyclo[3.3.1.1[3,7]]dec-1-ylmethyl)benzamide (1.0 g, Example 23a) in tetrahydrofuran (20 ml). After 10 min. the reaction mixture was decanted onto dry solid carbon dioxide and allowed to warm to ambient temperature. The reaction mixture was acidified with concentrated hydrochloric acid and extracted with ether. The organics were separated, dried over magnesium sulfate and concentrated under reduced pressure to give a residue which was purified by silica gel chromatography (eluting with iso-hexane/ethyl acetate 3:1 to 1:1+1% AcOH), to yield the subtitle compound as a solid (0.45 g).

MS (APCI+ve) 348/350 (M+H)+

$^1$H NMR (DMSO-d6) δ 13.33 (1H, s), 8.44 (1H, t), 7.94 (1H, dd), 7.87 (1H, d), 7.63 (1H, d), 2.95 (2H, d), 1.95 (3H, s), 1.63 (6H, q), 1.53 (6H, s).

b) 2-Chloro-5-(piperazine-1-carbonyl)-N-(tricyclo[3.3.1.1[3,7]]dec-1-ylmethyl)-benzamide, hydrochloride salt Ethyldiisopropylamine (0.3 ml) was added at ambient temperature to a solution of 4-chloro-N-(tricyclo[3.3.1.1[3,7]]dec-1-ylmethyl)-isophthalamic acid (0.15 g, Example 60a), piperazine-1-carboxylic acid tert-butyl ester (0.16 g) and PyBrOP (0.40 g) in N-methylpyrrolidinone (10 ml). After 5 h the reaction mixture was diluted with ethyl acetate and washed twice with water, twice with 10% KHSO$_4$ solution, twice with saturated NaHCO$_3$ solution and once with brine, then dried over magnesium sulfate and concentrated under reduced pressure. The residue was purified by silica gel chromatography (eluting with ethanol (0–5%) in dichloromethane), then redissolved in methanol (10 ml) and treated with hydrochloric acid (4N dioxane, 1 ml). After 48 h the reaction mixture was concentrated under reduced pressure and recrystallised from iso-hexaxne/propan-2-ol to yield the title compound as a solid (0.10 g).

MS (APCI+ve) 416/418 (M+H)+

$^1$H NMR (DMSO-d6) δ 9.18 (1H, t), 8.42 (1H, t), 7.59 (1H, d), 7.47–7.52 (2H, m), 3.50–3.90 (4H, brs), 3.05–3.25 (4H, brs), 2.94 (2H, d), 1.95 (3H, s), 1.63 (6H, q), 1.52 (6H, s).

The following Examples were made in an analogous manner.

EXAMPLE 61

2-Chloro-5-([1,4]diazepane-1-carbonyl)-N(tricyclo[3.3.1.1[3,7]]dec-1-ylmethyl)-benzamide, hydrochloride salt

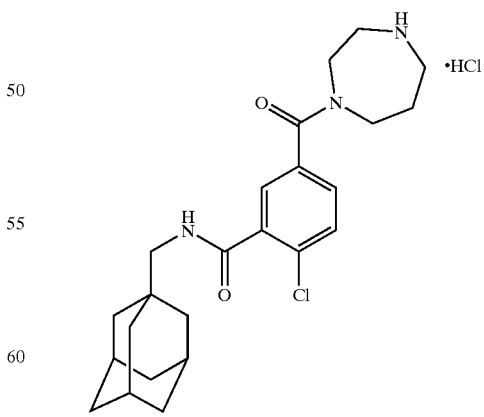

MS (APCI+ve) 430/432 (M+H)+

$^1$H NMR (DMSO-d6) δ 9.10 (2H, brs), 8.06 (1H, brs), 7.53 (1H, d), 7.45–7.48 (2H, m), 3.78 (2H, brs), 3.54 (2H, brs), 3.20–3.25 (4H, m), 2.97 (2H, d), 2.00 (2H, m), 1.95 (3H, s), 1.65 (6H, q), 1.55 (6H, s).

EXAMPLE 62

4-Chloro-N-1-(piperidin-4-yl-)-N2-(tricyclo[3.3.1.1³,⁷]dec-1-ylmethyl)-isophthalamide, hydrochloride salt

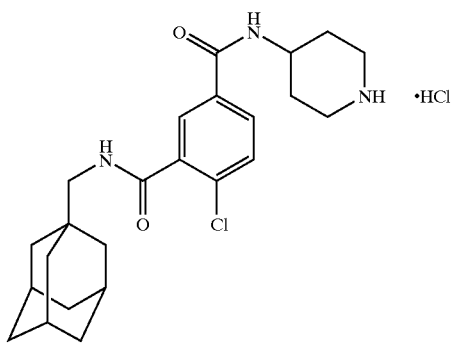

MS (APCI+ve) 430/432 (M+H)+

¹H NMR (DMSO-d6) δ 8.66–8.76 (3H, m), 8.42 (11H, t), 7.89–7.93 (2H, m), 7.60 (1H, d), 4.01–4.09 (1H, m), 3.29 (2H, d), 2.95–3.05 (4H, m), 1.95 (5H, brs), 1.47–1.82 (14H, m).

EXAMPLE 63

2-Chloro-5-(hydroxy-4-piperidinylmethyl)-N-(tricyclo[3.3.1.1³,⁷]dec-1-ylmethyl)-benzamide, hydrochloride salt

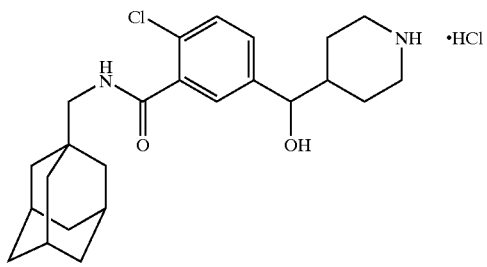

a) 2-Chloro-5-[4-[[{1,1-dimethylethyl}oxycarbonyl]piperidinyl]-hydroxymethyl]-N-(tricyclo[3.3.1.1³,⁷]dec-1-ylmethyl)-benzamide To a solution of 5-bromo-2-chloro-N-(tricyclo[3.3.1.1³,⁷]dec-1-ylmethyl)-benzamide (1.5 g, Example 23a) in anhydrous tetrahydrofuran (50 ml) under a nitrogen atmosphere at −78° C. was added dropwise n-butyllithium solution (2.5M in hexanes, 3.4 ml). The mixture was stirred for 10 min. at −78° C., then a solution of 4-formyl-1-piperidinecarboxylic acid, 1,1-dimethylethyl ester (1.09 g, Journal of Medicinal Chemistry, 1999, 42(12), 2180–2190) in anhydrous tetrahydrofuran (10 ml) was added dropwise. The reaction mixture was stirred at −78° C. for 30 min. then quenched with saturated aqueous ammonium chloride is solution (100 ml). The product was extracted twice with ethyl acetate (2×100 ml). The organic extracts were combined, dried over anhydrous magnesium sulfate, filtered and concentrated under reduced pressure. The residue was purified by chromatography on silica gel eluting with iso-hexane : ethyl acetate/(2:1) then (1:2), then purified further by HPLC eluting with a gradient of 0–5% ethanol in dichloromethane to give the subtitle compound as a white foam (0.61 g).

MS (APCI+ve) 517 (M+H)+

¹H NMR (DMSO-d6) δ 8.28 (1H, t); 7.40 (1H, d); 7.33–7.27 (2H, m); 5.33 (1H, d); 4.34 (1H, t); 3.93 (3H, bs); 2.93 (2H, d); 2.61 (2H, bs); 1.94 (3H, bs); 1.63 (6H, q); 1.53 (6H, d); 1.37 (9H, s); 1.34–1.23 (2H, m); 1.09 (2H, dt).

b) 2-Chloro-5-(hydroxy-4-piperidinylmethyl)-N-(tricyclo[3.3.1.1³,⁷]dec-1-ylmethyl)-benzamide, hydrochloride salt A solution of 2-chloro-5-[4-[[{1,1-dimethylethyl}oxycarbonyl]-piperidinyl]-hydroxymethyl]-N-(tricyclo[3.3.1.1³,⁷]dec-1-ylmethyl)-benzamide (0.10 g, Example 63a) in methanol (3 ml) was treated with 4N hydrochloric acid solution in dioxane (1 ml). After 14 h the solvents were removed under reduced pressure and the residue was triturated with diethyl ether to give the title compound as a white powder (0.062 g).

MS (APCI+ve) 417 (M+H−HCl)+

¹H NMR (DMSO-d6) δ 8.70 (1H, bs); 8.29 (2H, bt); 7.44 (1H, d); 7.33 (2H, dt), 5.53 (1H, d); 4.40 (1H, t); 3.23 (2H, bs); 2.93 (2H, d); 2.76 (2H, bd); 1.94 (3H, bs); 1.77–1.36 (1H, m); 1.53 (6H, s).

EXAMPLE 64

(±)-2-Chloro-5-(hydroxy-3-piperidinylmethyl)-N-(tricyclo[3.3.1.1³,⁷]dec-1-ylmethyl)-benzamide, hydrochloride salt

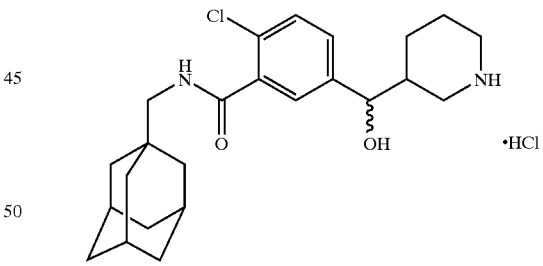

Prepared by an analogous route to Example 63 employing 3-formyl-1-piperidinecarboxylic acid, 1,1-dimethylethyl ester.

MS (APCI+ve) MW 417/419 (M+H)+

¹H NMR (CD₃OD) δ 8.41 (1H, t); 7.46 (1H, d); 7.41 (1H, d); 7.39 (1H, s); 4.65 (0.5H, d); 4.50 (0.5H, d); 3.74 (0.5H, td); 3.66 (1H, q); 3.57 (0.5H, t); 3.44 (0.5H, bd); 3.18 (0.5H, bd); 3.06 (2H, d); 2.86 (2H, qd); 2.10–1.87 (m, 2H); 1.98 (3H, bs); 1.77 (3H, d); 1.68 (3H, bd); 1.63 (6H, s), 1.60–1.50 (m, 1H); 1.50–1.36 (m, 1H).

EXAMPLE 65

2-Bromo-5-piperazin-1-ylmethyl-N-(tricyclo[3.3.1.1³,⁷]dec-1-ylmethyl)-benzamide, hydrochloride salt

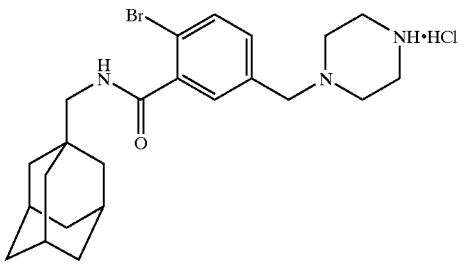

a) 2-Bromo-5-bromomethyl-N-(tricyclo[3.3.1.1³,⁷]dec-1-ylmethyl)-benzamide

To a solution of 2-bromo-5-bromomethyl-benzoic acid (6.1 g) in dichloromethane (100 ml) at 0° C. were added dimethylformamide (0.2 ml) followed by oxalylchloride (3 ml). The reaction was stirred at room temperature for 0.5 hour and concentrated under vacuum. The acylchloride was redissolved in dichloromethane (100 ml) and and di-isopropylethylamine (6 ml) followed by adamantanemethylamine (3.5 ml) added at 0° C. The mixture was stirred at 0° C. for 10 min., then partitioned between diethyl ether and 1N aqueous hydrochloric acid. The organic layer was dried over magnesium sulfate and concentrated in vacuo. The crude material was purified by recrystallisation from dichloromethane/ethylacetate/i-hexane to afford the title compound as a white solid (6.5 g) (sample contained some of the corresponding benzyl chloride).

b) 2-Bromo-5-(4-[{1,1-dimethylethyl}oxycarbonyl]-piperazin-1-yl)methyl-N-(tricyclo[3.3.1.1³,⁷]dec-1-ylmethyl)-benzamide A mixture of 2-bromo-5-bromomethyl-N-(tricyclo[3.3.1.1³,⁷]dec-1-ylmethyl)-benzamide (Example 65a, 5.0 g), 1-tertbutyloxycarbonylpiperazine (2.3 g), potassium carbonate (3.2 g), potassium iodide (0.30 g) and acetone (75 ml) was refluxed in the dark for 14 h. The mixture was concentrated in vacuo, partitioned between ethyl acetate and water, then washed with brine. The organic layer was dried over magnesium sulfate and concentrated in vacuo. Recrystallization from ethyl acetate:isohexane gave the subtitle compound as colourless solid (4.7 g).

MS (APCI+ve) MW 546 (M+H)+ c) 2-Bromo-5-piperazin-1-ylmethyl-N-(tricyclo[3.3.1.1³,⁷]dec-1-ylmethyl)-benzamide, hydrochloride salt 2-Bromo-5-(4-[{1,1-dimethylethyl}oxycarbonyl]-piperazin-1-yl)methyl-N-(tricyclo[3.3.1.1³,⁷]dec-1-ylmethyl)-benzamide (Example 65b, 0.40 g) was dissolved in methanol (15 ml), and 4N HCl in dioxane (3 ml) added. The mixture was stirred at room temperature for 14 h. The solvent was removed under vacuum and the resulting solid was triturated with ether to afford the title compound as a white powder (0.23 g).

MS (APCI+ve) MW 447(M+H)+

$^1$H NMR (DMSO-d6) δ 9.53 (1H, s, br); 8.31 (1H, t); 7.72 (1H, d); 7.60 (1H, m), 4.33 (1H, m); 3.50–3.00 (4H, m); 3.50–3.40 (1H, m); 2.94 (2H, d); 1.94 (3H, bs); 1.71–1.58 (6H, m); 1.54 (6H, bs).

EXAMPLE 66

2-Chloro-5-[2-(1-piperazinyl)ethyl]-N-(tricyclo[3.3.1.1³,⁷]dec-1-ylmethyl)-benzamide, hydrocloride salt

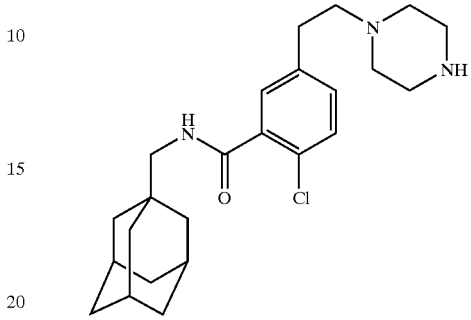

a) 2-Chloro-5-(2-hydroxyethyl)-N-(tricyclo[3.3.1.1³,⁷]dec-1-ylmethyl)-benzamide A solution of 5-bromo-2-chloro-N-(tricyclo[3.3.1.1³,⁷]dec-1-ylmethyl)-benzamide (3.0 g, Example 23a) in anhydrous tetrahydrofuran (100 ml) was cooled to −78° C. under a nitrogen atmosphere. A solution of methyllithium (1.4M in diethyl ether, 4.9 ml) was added over 2 min. The mixture was stirred at −78° C. for 10 min., then a solution tert-butyllithium (1.7M in pentane, 9.3 ml) was added dropwise. The mixture was stirred at −78° C. for a further 10 min., then ethylene oxide (1.0 ml) was added. The resulting solution was stirred at −78° C. for 30 min. then was warmed to 0° C. and stirred for another 6 h. The reaction mixture was quenched with saturated aqueous ammonium chloride solution (70 ml) and extracted with ethyl acetate (3×100 ml). The combined extracts were dried over anhydrous magnesium sulfate, filtered, and the filtrate concentrated under reduced pressure. The residue was purified by chromatography over silica gel eluting with dichloromethane:ethanol (98:2) to give the subtitle compound as a pale yellow solid (0.89 g).

MS (APCI+ve) 348 (M+H)+

$^1$H NMR (DMSO-d$_6$) δ 8.27 (1H, t), 7.36 (1H, d); 7.28–7.23 (2H, m); 4.65 (1H, t); 3.60 (2H, q); 2.92 (2H, d); 2.73 (2H, t); 1.94 (3H, bs); 1.63 (6H, q); 1.52 (6H, d).

b) 2-Chloro-5-(2-oxoethyl)-N-(tricyclo[3.3.1.1³,⁷]dec-1-ylmethyl)-benzamide

To a solution of 2-chloro-5-(2-hydroxyethyl)-N-(tricyclo[3.3.1.1³,⁷]dec-1-ylmethyl)-benzamide (1.07 g, Example 66a) in anhydrous dichloromethane (20 ml) was added Dess-Martin periodinane reagent (1.95 g) and the mixture was stirred at room temperature for 1 h. Sodium thiosulfate (3.43 g) was dissolved in aqueous sodium bicarbonate solution (28 ml) and added to the reaction mixture. Diethyl ether (50 ml) was then added and the mixture was stirred for 10 min. The layers were partitioned and the organic layer was washed with water then brine. The organic extracts were then dried over anhydrous magnesium sulfate, filtered and concentrated under reduced pressure to afford the subtitle compound as a white solid (1.06 g).

MS (APCI+ve) 346 (M+H)+

$^1$H NMR (DMSO-d$_6$) δ 9.69 (1H, s); 8.32 (1H, t); 7.45 (1H, d); 7.30–7.24 (2H, m); 3.84 (2H, s); 2.92 (2H, d); 1.94 (3H, bs); 1.63 (6H, q); 1.52 (6H, d).

c) 2-Chloro-5-[2-(1-piperazinyl)ethyl]-N-(tricyclo[3.3.1.1$^{3,7}$]dec-1-ylmethyl)-benzamide hydrochloride salt To a solution of 2-chloro-5-(2-oxoethyl)-N-(tricyclo[3.3.1.1$^{3,7}$]dec-1-ylmethyl)-benzamide (0.101 g, Example 66b) in anhydrous 1,2-dichloroethane (5 ml) was added 1-piperazinecarboxylic acid, 1,1-dimethylethyl ester (0.108 g) then sodium triacetoxyborohydride (0.086 g). The reaction mixture was stirred for 14 h at room temperature. Water (10 ml) and dichloromethane (10 ml) were added and the layers were partitioned. The organic extract was dried over anhydrous magnesium sulfate, filtered and concentrated under reduced pressure. The residue was purified by HPLC eluting with a gradient of 0–5% ethanol in dichloromethane then by chromatography over silica gel eluting with ethyl acetate. The white powder obtained was dissolved in methanol (5 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.047 g).

MS (APCI+ve) 416 (M+H)$^+$ $^1$H NMR (CD$_3$OD) δ 8.42 (1H, t); 7.46 (1H, d); 7.41–7.38 (2H, m); 3.63–3.49 (8H, m); 3.48–3.45 (2H, m); 3.19–3.14 (2H, m); 3.06 (2H, s); 1.99 (3H, bs); 1.73 (6H, q); 1.63 (6H, d).

EXAMPLE 67

2-Chloro-5-[2-(2,5-diazabicyclo[2.2.1]hept-2-yl)ethyl]-N-(tricyclo[3.3.1.1$^{3,7}$]dec-1-ylmethyl)-benzamide, hydrochloride salt

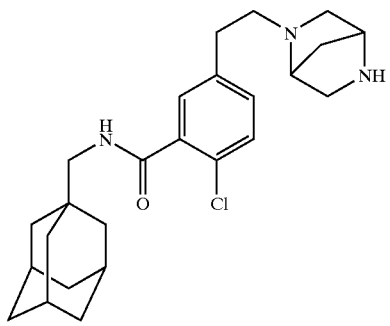

Prepared according to the method described in Example 66c from 2-chloro-5-(2-oxoethyl)-N-(tricyclo[3.3.1.1$^{3,7}$]dec-1-ylmethyl)-benzamide (0.094 g, Example 66b), 2,5-diazabicyclo[2.2.1]heptane-2-carboxylic acid, 1,1-dimethylethyl ester (0.108 g), sodium triacetoxyborohydride (0.081 g) and 1,2-dichloroethane (2 ml). After work-up, the residue was purified by HPLC eluting with a gradient of 0–5% ethanol in dichloromethane. The white powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.067 g).

MS (APCI+ve) 428 (M+H)$^+$ $^1$H NMR (CD$_3$OD) δ 7.49–7.40 (3H, m); 4.64 (2H, d); 3.92 (2H, d); 3.77–3.48 (4H, m); 3.18 (2H, t); 3.08 (2H, s); 2.61 (1H, bd); 2.28 (1H, bd); 2.00 (3H, bs); 1.75 (6H, q); 1.64 (6H, d).

EXAMPLE 68

5-[2-(4-Amino-1-piperidinyl)ethyl]-2-chloro-N-(tricyclo[3.3.1.1$^{3,7}$]dec-1-ylmethyl)-benzamide, hydrochloride salt

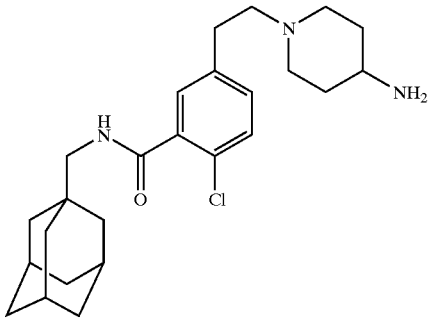

Prepared according to the method described in Example 66c from 2-chloro-5-(2-oxoethyl)-N-(tricyclo[3.3.1.1$^{3,7}$]dec-1-ylmethyl)-benzamide (0.094 g, Example 66b), 4-piperidinyl-carbamic acid, 1,1-dimethylethyl ester (0.109 g), sodium triacetoxyborohydride (0.081 g) and 1,2-dichloroethane (2 ml). After work-up, the residue was purified by HPLC eluting with a gradient of 0–5% ethanol in dichloromethane. The white powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.065 g).

MS (APCI+ve) 430 (M+H)$^+$ $^1$H NMR (CD$_3$OD) δ 8.43 (1H, t); 7.49–7.38 (3H, m); 3.78 (2H, bd); 3.64–3.42 (2H, m); 3.41–3.35 (2H, m); 3.23–3.14 (3H, m); 3.08 (2H, s); 2.33–2.29 (2H, m); 2.13–2.04 (2H, m); 2.00 (3H, bs); 1.75 (6H, q); 1.64 (6H, d).

EXAMPLE 69

2-Chloro-5-[2-(3-piperidinylamino)ethyl]-N-(tricyclo[3.3.1.1$^{3,7}$]dec-1-ylmethyl)-benzamide, dihydrochloride salt

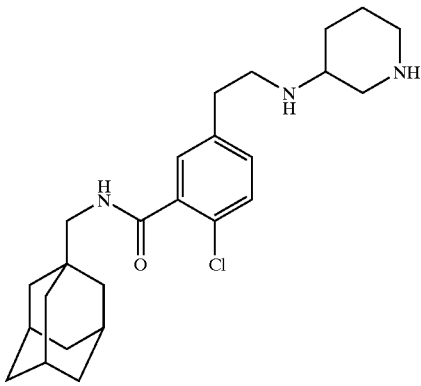

Prepared according to the method described in Example 66c from 2-chloro-5-(2-oxoethyl)-N-(tricyclo[3.3.1.1$^{3,7}$]dec-1-ylmethyl)-benzamide (0.094 g, Example 66b), 3-amino-1-piperidinecarboxylic acid, 1,1-dimethylethyl ester (0.109 g), sodium triacetoxyborohydride (0.081 g) and 1,2-dichloroethane (2 ml). After work-up, the residue was purified by HPLC eluting with a gradient of 0–5% ethanol in dichloromethane. The white powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.065 g).

MS (APCI+ve) 430 (M+H)$^+$ $^1$H NMR (CD$_3$OD) δ 7.49–7.46 (1H, m); 7.42–7.38 (2H, m); 3.76 (1H, bd); 3.64–3.54 (1H, m); 3.44–3.34 (3H, m); 3.19–2.98 (4H, m); 3.08 (2H, s); 2.34 (1H, bd); 2.18–2.12 (1H, m); 2.00 (3H, bs); 1.89–1.78 (2H, m); 1.74 (6H, q); 1.64 (6H, d).

EXAMPLE 70

5-[2-(3-Amino-1-piperidinyl)ethyl]-2-chloro-N-(tricyclo[3.3.1.1$^{3,7}$]dec-1-ylmethyl)-benzamide, hydrochloride salt

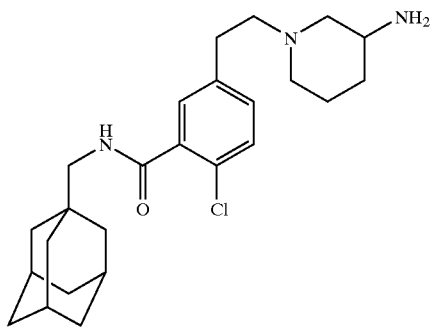

Prepared according to the method described in Example 66c from 2-chloro-5-(2-oxoethyl)-N-(tricyclo[3.3.1.1$^{3,7}$] dec-1-ylmethyl)-benzamide (0.094 g, Example 66b), 3-piperidinyl-carbamic acid, 1,1-dimethylethyl ester (0.109 g), sodium triacetoxyborohydride (0.081 g) and 1,2-dichloroethane (2 ml). After work-up, the residue was purified by HPLC eluting with a gradient of 0–5% ethanol in dichloromethane then by HPLC eluting with a gradient of 0–2% ethanol in dichloromethane. The white powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.032 g).

MS (APCI+ve) 430 (M+H)$^+$ $^1$H NMR (CD$_3$OD) δ 7.49–7.46 (1H, m); 7.42–7.39 (2H, m); 3.80–3.67 (3H, m); 3.46 (2H, t); 3.19 (2H, t); 3.08 (2H, s); 3.09–3.04 (1H, m); 2.14 (1H, bt); 2.00 (3H, bs); 1.74 (6H, q); 1.77–1.68 (2H, m); 1.64 (6H, d).

EXAMPLE 71

2-Chloro-5-[2-(3-pyrrolidinylamino)ethyl]-N-(tricyclo[3.3.1.1$^{3,7}$]dec-1-ylmethyl)-benzamide, dihydrochloride salt

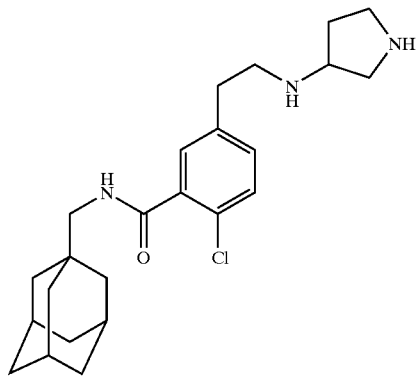

Prepared according to the method described in Example 66c from 2-chloro-5-(2-oxoethyl)-N-(tricyclo[3.3.1.1$^{3,7}$] dec-1-ylmethyl)-benzamide (0.094 g, Example 66b), 3-amino-1-pyrrolidinecarboxylic acid, 1,1-dimethylethyl ester (0.101 g), sodium triacetoxyborohydride (0.081 g) and 1,2-dichloroethane (2 ml). After work-up, the residue was purified by HPLC eluting with a gradient of 0–5% ethanol in dichloromethane. The pale orange powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a pale orange powder (0.033 g).

MS (APCI+ve) 416 (M+H)$^+$ $^1$H NMR (CD$_3$OD) δ 7.46–7.39 (3H, m); 4.12 (1H, bs); 3.78–3.71 (1H, m); 3.69–3.57 (2H, m); 3.43–3.32 (4H, m); 3.13 (2H, bt); 3.06 (2H, s); 2.62–2.51 (1H, m); 2.38–2.29 (1H, m); 1.98 (3H, s); 1.73 (6H, q); 1.63 (6H, s).

EXAMPLE 72

5-[2-[(3R)-3-Aminopyrrolidinyl]ethyl]-2-chloro-N-(tricyclo[3.3.1.1$^{3,7}$]dec-1-ylmethyl)-benzamide, hydrochloride salt

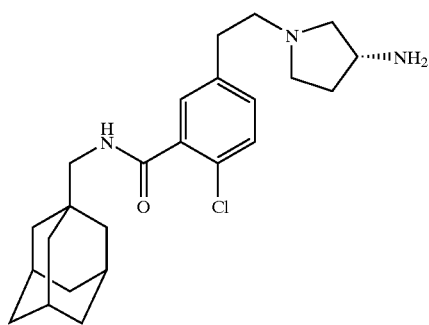

Prepared according to the method described in Example 66c from 2-chloro-5-(2-oxoethyl)-N-(tricyclo[3.3.1.1$^{3,7}$] dec-1-ylmethyl)-benzamide (0.094 g, Example 66b), (3R)-pyrrolidinyl-carbamic acid, 1,1-dimethylethyl ester (0.101 g), sodium triacetoxyborohydride (0.081 g) and 1,2- dichloroethane (2 ml). After work-up, the residue was purified by HPLC eluting with a gradient of 0–5% ethanol in dichloromethane. The white powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.060 g).

MS (APCI+ve) 416 (M+H)$^+$ $^1$H NMR (CD$_3$OD) δ 7.49–7.41 (3H, m); 4.86 (1H, bs); 4.05–3.80 (2H, m); 3.58 (4H, bs); 3.17 (2H, t); 3.08 (2H, s); 2.66 (1H, bs); 2.28 (1H, bs); 2.00 (3H, s); 1.74 (6H, q); 1.64 (6H, s).

EXAMPLE 73

2-Chloro-5-[2-[2-(hydroxymethyl)-1-piperazinyl]ethyl]-N-(tricyclo[3.3.1.1$^{3,7}$]dec-1-ylmethyl)-benzamide, hydrochloride salt

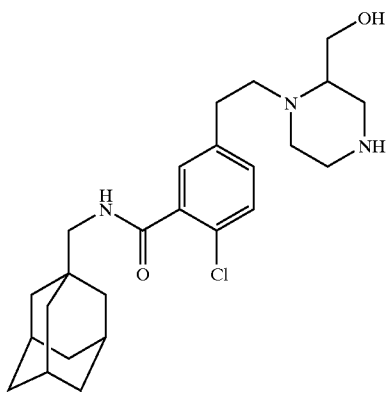

Prepared according to the method described in Example 66c from 2-chloro-5-(2-oxoethyl)-N-(tricyclo[3.3.1.1$^{3,7}$]dec-1-ylmethyl)-benzamide (0.094 g, Example 66b), 3-(hydroxymethyl)-1-piperazinecarboxylic acid, 1,1-dimethylethyl ester (0.117 g), sodium triacetoxyborohydride (0.081 g) and 1,2-dichloroethane (2 ml). After work-up, the residue was purified by HPLC eluting with a gradient of 0–5% ethanol in dichloromethane then chromatography eluting with ethyl acetate then ethyl acetate: ethanol (95:5). The white powder obtained was dissolved in methanol (2 ml) and a solution of hydrochloric acid in dioxane (4N, 1 ml) was added. The mixture was stirred for 14 h at room temperature. Solvents were then removed under reduced pressure and the product obtained was triturated with diethyl ether to afford the title compound as a white powder (0.016 g).

MS (APCI+ve) 446 (M+H)$^+$ $^1$H NMR (CD$_3$OD) δ 8.43 (1H, t); 7.48–7.40 (3H, m); 4.14 (1H, bd); 3.93 (1H, bd); 3.81–3.76 (2H, m); 3.74–3.58 (5H, m); 3.57–3.45 (2H, m); 3.28–3.19 (1H, m); 3.17–3.11 (1H, m); 3.07 (2H, s); 1.99 (3H, bs); 1.73 (6H, q); 1.64 (6H, s).

EXAMPLE 74

2-Chloro-5-(hexahydro-1H-1,4-diazepin-1-yl)-N-(2-tricyclo[3.3.1.1$^{3,7}$]dec-1-ylethyl)-benzamide, hydrochloride salt

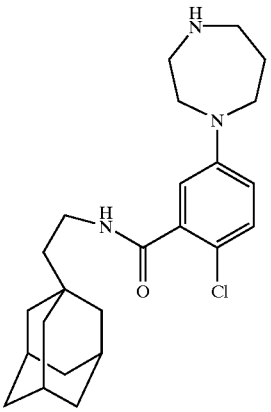

a) 4-[4-Chloro-3-[[(2-tricyclo[3.3.1.1$^{3,7}$]dec-1-ylethyl)amino]carbonyl]phenyl]hexahydro-1H-1,4-diazepine-1-carboxylic acid, 1,1-dimethylethyl ester A solution of 4-(3-carboxy-4-chlorophenyl)hexahydro-1H-1,4-diazepine-1-carboxylic acid, 1,1-dimethylethyl ester (0.075 g, Example 5b) and 1,140 -carbonyldiimidazole (0.034 g) in dimethylformamide (3 ml) was stirred at room temperature of 2.5 h. Tricyclo[3.3.1.1$^{3,7}$]decane-1-ethanamine, hydrochloride salt (0.045 g) and N,N-diisopropylethylamine (0.037 ml) were then added and stirring continued for 14 h. The reaction mixture was poured into water and extracted with ethyl acetate three times. The ethyl acetate layers were combined and washed with 2M hydrochloric acid, 10% aqueous sodium hydroxide and brine, then dried over magnesium sulfate and concentrated under reduced pressure. Purification by chromatography on silica gel eluting with 20% ethyl acetate in iso-hexane gave the subtitle compound as a yellow oil (0.053 g).

MS (APCI+ve) 460/462 (M–$^t$Bu)$^-$ b) 2-Chloro-5-(hexahydro-1H-1,4-diazepin-1-yl)-N-(2-tricyclo[3.3.1.1$^{3,7}$]dec-1-ylethyl)-benzamide, hydrochloride salt 4-[4-Chloro-3-[[(2-tricyclo[3.3.1.1$^{3,7}$]dec-1-ylethyl)amino]carbonyl]phenyl]-hexahydro-1H-1,4-diazepine-1-carboxylic acid, 1,1-dimethylethyl ester (0.053 g, Example 74a) was dissolved in methanol (5 ml) and hydrochloric acid (0.5 ml from a 4N solution in dioxane) was added. After stirring at room temperature for 14 h, the mixture was evaporated to ¾ original volume under reduced pressure. Diethyl ether was gradually added to the solution and the resulting precipitate was collected by filtration, washed with diethyl ether and dried in vacuo to afford the title compound as a cream solid (0.017 g).

MS (APCI+ve) 416/418 (M–HCl)+

$^1$H NMR (DMSO-d6) δ 9.07 (2H, bs); 8.18 (1H, t); 7.22 (1H, d); 6.80 (1H, dd); 6.71 (1H, d); 3.70 (2H, m); 3.50 (2H, t); 3.25–3.17 (4H, m); 3.07 (2H, m); 2.08–2.06 (2H, m); 1.93 (3H, bs); 1.68 (3H, d); 1.61 (3H, d); 1.51 (6H, s); 1.34–1.28 (2H, m).

EXAMPLE 75

(+/−)-5-(3-Amino-1-pyrrolidinyl)-2-chloro-N-(2-tricyclo[3.3.1.1^{3,7}]dec-1-ylethyl)-benzamide, hydrochloride salt

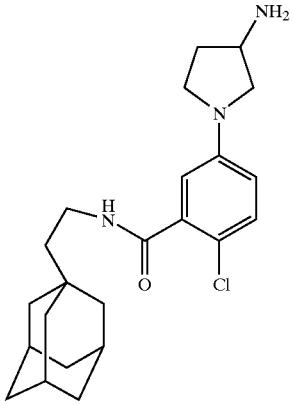

Prepared as described in example 74 above using (+/−)-2-chloro-5-[3-[[(1,1-dimethylethoxy)carbonyl]amino]-1-pyrrolidinyl]-benzoic acid (0.090 g), 1,1′-carbonyldiimidazole (0.043 g), tricyclo[3.3.1.1^{3,7}]decane-1-ethanamine, hydrochloride salt (0.057 g), N,N-diisopropylethylamine (0.046 ml) and dimethylformamide (3 ml). This compound was treated with 4N hydrochloric acid in dioxane (0.5 ml) and methanol (5 ml) to yield the title compound (0.025 g).

MS (APCI+ve) 402/404 (M−HCl)+

$^1$H NMR (DMSO-d6) δ 8.24 (3H, bs); 8.18 (1H, t); 7.24 (1H, d); 6.60 (1H, dd); 6.49 (1H, d); 3.93 (1H, m); 3.54–3.37 (2H, m); 3.31–3.17 (4H, m); 2.37–2.28 (1H, m); 2.07 (1H, m); 1.93 (3H, bs); 1.68 (3H, d); 1.61 (3H, d); 1.51 (6H, s); 1.34–1.28 (2H, m).

EXAMPLE 76

2-Chloro-5-(4-piperidinylcarbonyl)-N-(tricyclo[3.3.1.1^{3,7}]dec-1-ylmethyl)-benzamide, hydrochloride salt

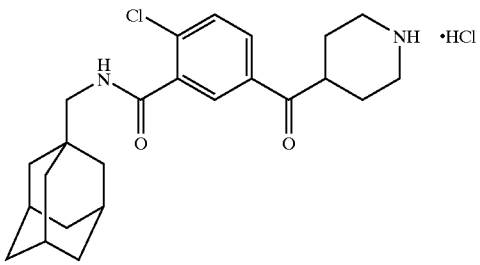

a) 4-[4-Chloro-3-[[(tricyclo[3.3.1.1^{3,7}]dec-1-ylmethyl)amino]carbonyl]benzoyl]-1-piperidinecarboxylic acid, 1,1-dimethylethyl ester To dimethyl sulphoxide (0.155 ml) in anhydrous dichloromethane (11 ml) at −78° C. was added oxalyl chloride (0.086 ml) and the mixture was stirred for 5min. at −78° C. A solution of 4-[[4-chloro-3-[[(tricyclo[3.3.1.1^{3,7}]dec-1-ylmethyl)amino]carbonyl]phenyl]hydroxymethyl]-1-piperidinecarboxylic acid, 1,1-dimethylethyl ester (0.47 g, Example 64) in anhydrous dichloromethane (3 ml) was added dropwise and the mixture was stirred for 15 min. at −78° C. Triethylamine (0.633 ml) was then added and the solution was warmed to room temperature. After 45 min. at room temperature, the reaction mixture was poured onto water and the layers were separated. The organic extract was dried over anhydrous magnesium sulfate, filtered and concentrated under reduced pressure. The residue was purified by HPLC eluting a gradient of 0–5% ethanol in dichloromethane to give the subtitle compound as a white foam (0.31 g).

MS (APCI+ve) 15 (M+H)+

$^1$H NMR (DMSO-d6) δ 8.46 (1H, t); 8.06–8.01 (1H, m); 7.95–7.92 (1H, m); 7.70–7.65 (1H, m); 3.97 (2H, bd); 3.72–3.61 (1H, m); 2.97 (2H, t); 2.92 (2H, bs); 1.96 (3H, bs); 1.77 (2H, d); 1.65 (6H, q); 1.55 (6H, s); 1.41 (9H, s); 1.48–1.33 (2H, m).

b) 2-Chloro-5-(4-piperidinylcarbonyl)-N-(tricyclo[3.3.1.1^{3,7}]dec-1-ylmethyl)-benzamide, hydrochloride salt A solution of 4-[4-chloro-3-[[(tricyclo[3.3.1.1^{3,7}]dec-1-ylmethyl)amino]carbonyl]benzoyl]-1-piperidinecarboxylic acid, 1,1-dimethylethyl ester (0.07 g, Example 76a) in methanol (3 ml) was treated with 4N hydrochloric acid solution in dioxane (1 ml). After 14 h the solvents were removed under reduced pressure and the residue was triturated with diethyl ether to give the title compound as a white powder (0.025 g).

MS (APCI+ve) 415 (M+H−HCl)+

$^1$H NMR (DMSO-d6) δ 8.90 (1H, bs); 8.64 (1H, bs); 8.46 (1H, t); 8.03 (1H, d); 7.95 (1H, s); 7.69 (1H, d); 3.81 (1H, t); 3.24–3.18 (2H, m); 3.09–2.99 (2H, m); 2.96 (2H, d); 2.01 (2H, dd); 1.95 (3H, s); 1.79 (2H, t); 1.64 (6H, q); 1.45 (6H, s).

EXAMPLE 77

2-Chloro-5-[1-hydroxy-1-(4-piperidinyl)ethyl]-N-(tricyclo[3.3.1.1^{3,7}]dec-1-ylmethyl)-benzamide, hydrochloride salt

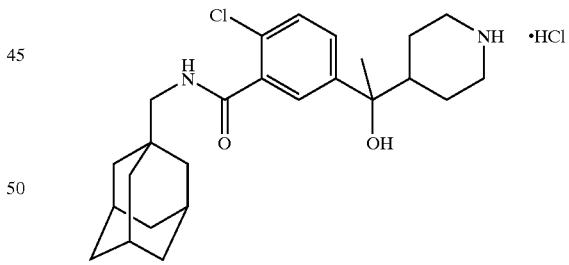

a) 4-[1-[4-Chloro-3-[[(tricyclo[3.3.1.1^{3,7}]dec-1-ylmethyl)amino]carbonyl]phenyl]hydroxyethyl]-1-piperidinecarboxylic acid, 1,1-dimethylethyl ester To methyl magnesiumbromide (3M solution in diethyl ether, 0.225 ml) in anhydrous diethyl ether (7 ml) under a nitrogen atmosphere was added slowly 4-[4-chloro-3-[[(tricyclo[3.3.1.1^{3,7}]dec-1-ylmethyl)amino]carbonyl]benzoyl]-1-piperidinecarboxylic acid, 1,1-dimethylethyl ester (0.23 g, Example 76a) in anhydrous diethyl ether (7 ml). The reaction mixture was stirred for 14 h at room temperature, then poured onto crushed ice. A solution of 10% aqueous potassium hydrogen sulphate was added keeping the pH of the solution >4. The layers were separated, and the aqueous layer was extracted with ethyl acetate (4×25 ml). The organic extracts were combined, dried over anhydrous magnesium sulfate, filtered and concentrated under reduced pressure. The residue was dissolved in methanol (3 ml) and hydrochloric acid (4N solution in dioxane, 2 ml) and stirred for 14 h at room temperature. Solvents were then removed under reduced pressure and the product (0.11 g) was redissolved in dichloromethane (3 ml). Triethylamine (0.066 ml) was added followed by di-tert-butyl-dicarbonate (0.055 g) and the reaction mixture was stirred for 1 hour at room temperature. Water was added and the layers were partitioned. The organic extract was dried over anhydrous magnesium sulfate, filtered and concentrated under reduced pressure. The residue was purified by HPLC eluting with a gradient of 0–5% ethanol in dichloromethane, then by RPHPLC eluting with a gradient of 75–5% of 0.1% aqueous ammonium acetate in acetonitrile to give the subtitle compound as a white foam (0.06 g).

MS (APCI+ve) 431 (M+H−BOC)+ b) 2-Chloro-5-[1-hydroxy-1-(4-piperidinyl)ethyl]-N-(tricyclo[3.3.1.1$^{3,7}$]dec-1-ylmethyl)-benzamide, hydrochloride salt To a solution of 4-[1-[4chloro-3-[[(tricyclo[3.3.1.1$^{3,7}$]dec-1-ylmethyl)amino]carbonyl]phenyl]-1-hydroxyethyl]-1-piperidinecarboxylic acid, 1,1-dimethylethyl ester (0.07 g, Example 77a) in methanol (3 ml) was added 4N hydrochloric acid solution in dioxane (1 ml). After 14 h the solvents were removed under reduced pressure and the residue was triturated with diethyl ether to give the title compound as a white powder (0.038 g).

MS (APCI+ve) 431 (M+H−HCl)+

$^1$H NMR (DMSO-d$_6$) δ 8.78 (1H, bs); 8.28 (1H, t); 7.44–7.40 (3H, m); 5.21 (1H, s); 3.25 (1H, d); 3.16 (1H, d); 2.98–2.89 (2H, m); 2.79–2.67 (2H, m); 1.94 (3H, bs); 1.84–1.75 (2H, m); 1.63 (6H, q); 1.53 (6H, s); 1.42 (3H, s); 1.53–1.31 (3H, m).

EXAMPLE 78

2-Chloro-5-[2-(1-piperazinyl)ethoxy)-N-(tricyclo[3.3.1.1$^{3,7}$]dec-1-ylmethyl)-benzamide, hydrochloride salt

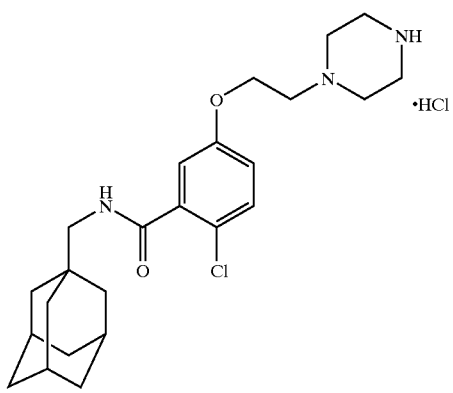

Prepared as described in Example 12b using 2-chloro-5-hydroxy-N-(tricyclo[3.3.1.1$^{3,7}$]dec-1-methyl)-benzamide (Example 12a) and 4-(2-hydroxyethyl)-1-piperazinecarboxylic acid, 1,1-dimethylethyl ester.

MS (APCI+ve) 432 (M+H)+

$^1$H NMR (CD$_3$OD) δ 8.40 (1H, t); 7.41 (1H, d); 7.14–7.06 (2H, m); 4.45 (2H, t); 3.76–3.58 (10H, m); 3.07–3.03 (2H, m); 1.98 (3H, s); 1.77 (3H, d); 1.69 (3H, d); 1.62 (6H, s).

EXAMPLE 79

2-Chloro-5-[2-(4-piperidinyl)ethoxy)-N-(tricyclo[3.3.1.1$^{3,7}$]dec-1-ylmethyl)-benzamide, hydrochloride salt

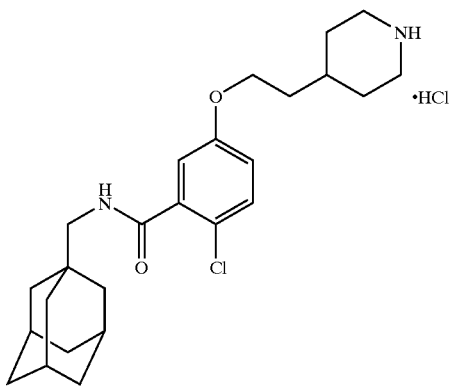

Prepared as described in Example 12b using 2-chloro-5-hydroxy-N-(tricyclo[3.3.1.1$^{3,7}$]dec-1-methyl)-benzamide (Example 12a) and 4-(2-hydroxyethyl)-1-piperidinecarboxylic acid, 1,1-dimethylethyl ester.

MS (APCI+ve) 431 (M+H)+

$^1$H NMR (DMSO-d6) δ 8.75 (1H, brs); 8.49 (1H, brs); 8.27 (1H, t); 7.37 (1H, d); 6.99 (1H, dd); 6.91 (1H, d); 4.03 (2H, t); 3.22 (2H, d); 2.92 (2H, d); 2.82 (2H, t); 1.94 (3H, s); 1.82 (2H, d); 1.79–1.70 (1H, m); 1.69–1.64 (5H, m); 1.59 (3H, d); 1.53 (6H, s); 1.43–1.30 (2H, m).

EXAMPLE 80

2-Chloro-5-[2-(4-piperidinyloxy)ethoxy)-N-(tricyclo[3.3.1.1$^{3,7}$]dec-1-ylmethyl)-benzamide, hydrochloride salt

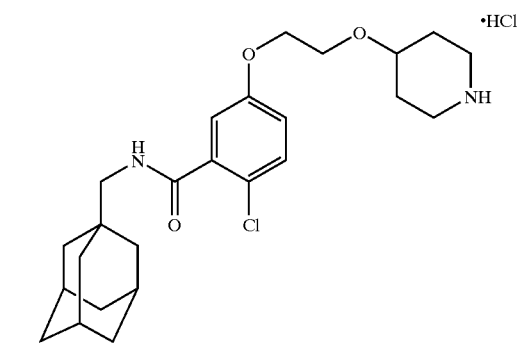

Prepared as described in Example 12b using 2-chloro-5-hydroxy-N-(tricyclo[3.3.1.1$^{3,7}$]dec-1-methyl)-benzamide (Example 12a) and 4-(2-hydroxyethoxy)-1-piperidinecarboxylic acid, 1,1-dimethylethyl ester.

MS (APCI+ve) 447 (M+H)+

$^1$H NMR (CD$_3$OD) δ 8.39 (1H, brt); 7.38–7.33 (1H, m); 7.06–6.98 (2H, m); 4.22–4.16 (2H, m); 3.88–3.82 (2H, m); 3.80–3.71 (1H, m); 3.36–3.24 (2H, m); 3.16–3.04 (4H, m); 1.99 (3H, s); 2.08–1.86 (4H, m); 1.78 (3H, d); 1.69 (3H, d); 1.62 (6H, s).

EXAMPLE 81

2-Chloro-5-[2-[2-(1-piperazinyl)ethoxy]ethoxy]-N-(tricyclo[3.3.1.1³,⁷]dec-1-ylmethyl)-benzamide, hydrochloride salt

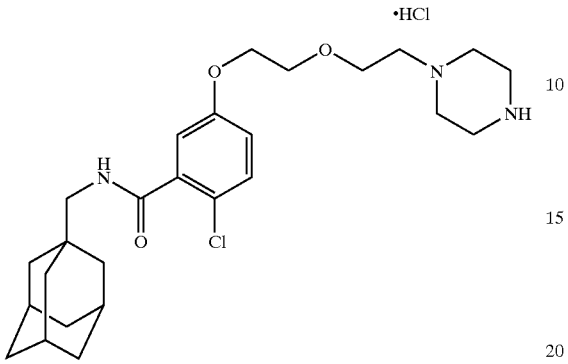

Prepared as described in Example 12b using 2-chloro-5-hydroxy-N-(tricyclo[3.3.1.1³,⁷]dec-1-methyl)-benzamide (0.20g, Example 12a) and 4-[2-(2-hydroxyethoxy)ethyl]-1-piperazine carboxylic acid, 1,1-dimethylethyl ester (0.26 g).

MS (APCI+ve) 476 (M+H)+

¹H NMR (CD₃OD) δ 7.7(1H, dd); 7.04–7.01 (2H, m); 4.25–4.18 (2H, m); 3.94 (2H, t); 3.91–3.87 (2H, m); 3.80–3.43 (10H, m); 3.06 (2H, s); 1.99 (3H, s); 1.75 (3H, d); 1.67 (3H, d); 1.62 (6H, s).

EXAMPLE 82

2-Chloro-5-[(5,6-dihydro-1(4H)-pyrimidinyl)methyl]-N-(tricyclo[3.3.1.1³,⁷]dec-1-ylmethyl)-benzamide

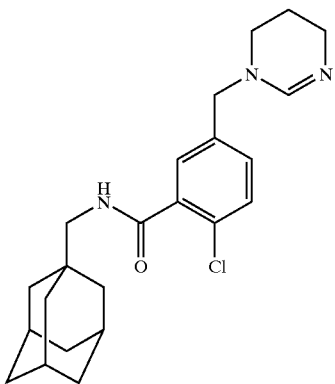

Prepared according to the method described in Example 8 from 5-bromomethyl-2-chloro-N-(tricyclo[3.3.1.1³,⁷]dec-1-ylmethyl)-benzamide (Example 8b,) and 1,4,5,6-tetrahydropyrimidine.

MS (APCI+ve) 400/402 (M+H)+

¹H NMR (CDCl₃) δ 7.84 (1H, s); 7.60 (1H, d); 7.43 (1H, d); 7.29 (1H, dd); 6.51 (1H, t); 4.39 (2H, s); 3.40–3.10 (3H, m); 3.17 (2H, d); 3.14 (1H, t); 2.01 (3H, s); 1.91 (q, 2H); 1.74 (3H, d); 1.64 (3H, d); 1.59 (6H, bs).

EXAMPLE 83

2-Chloro-5-[[4-[(2-hydroxyethyl)amino]-1-piperidinyl]methyl]-N-(tricyclo[3.3.1.1³,⁷]dec-1-ylmethyl)-benzamide, hydrochloride salt

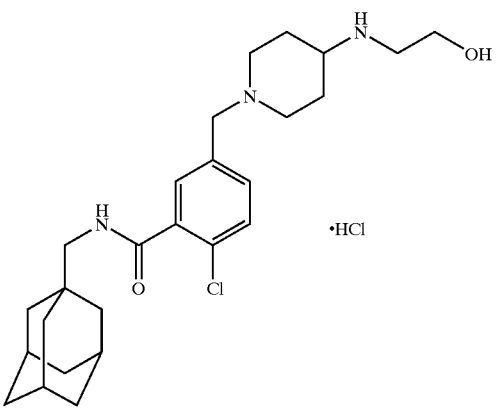

a) 2-Chloro-5-[(4-oxo-1-piperidinyl)methyl]-N-(tricyclo[3.3.1.1³,⁷]dec-1-ylmethyl)-benzamide Prepared according to the method described in Example 8c from 5-bromomethyl-2-chloro-N-(tricyclo[3.3.1.1³,⁷]dec-1-ylmethyl)-benzamide (Example 8b) and 4-piperidinone.

MS (APCI+ve) 456/458 (M+H)+ b) 2-Chloro-5-[[4-[(2-hydroxyethyl)amino]-1-piperidinyl]methyl]-N-(tricyclo[3.3.1.1³,⁷]dec-1-ylmethyl)-benzamide, hydrochloride salt To a solution of 2-chloro-5-[(4-oxo-1-piperidinyl)methyl]-N-(tricyclo[3.3.1.1³,⁷]dec-1-ylmethyl)-benzamide (0.150 g, Example 83a) in methanol (3ml ) at room temperature were added ethanolamine (0.11 ml) and sodium cyanoborohydride (0.068g). The pH was adjusted to 6 by adding a 4N solution of hydrogen chloride in dioxane and the reaction stirred for 48 h. The reaction was acidified with concentrated hydrochloric acid until gas evolution ceased. The precipitate was removed by filtration and the filtrate concentrated under vacuum. The residue was partitioned between ethyl acetate and water. The aqueous layer was basified with 5% aqueous sodium hydroxide and extracted with dichloromethane. The organics were washed with brine and dried over magnesium sulfate. The crude material was purified on silica gel (5% 7N ammonia in methanol/95% dichloromethane) to afford a white foam which was dissolved in ether/methanol and treated with a 4N solution of hydrogen chloride in dioxane to give the title compound (0.135 g).

MS (APCI+ve) 460/462 (M+H)+

¹H NMR (CD₃OD) δ 8.47 (1H, t); 7.67 (1H, d); 7.64 (1H, dd); 7.60 (1H, d); 4.39 (2H, s); 3.81 (2H, t); 3.62 (2H, bd); 3.52 (1H, t); 3.23–3.10 (4H, m); 3.09 (2H, d); 2.39 (2H, d); 2.07 (2H, q); 1.99 (s, 3H); 1.77 (3H, d); 1.70 (3H, d); 1.64 (6H, d).

EXAMPLE 84

2-Chloro-5-[[4-hydroxy4-[[(1-methylethyl)amino]methyl]-1-piperidinyl]methyl]-N-(tricyclo[3.3.1.1$^{3,7}$]dec-1-ylmethyl)-benzamide

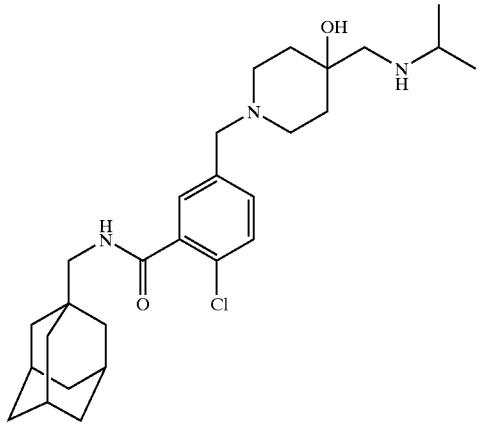

a) 2-Chloro-5-(1-oxa-6-azaspiro[2.5]oct-6-ylmethyl)-N-(tricyclo[3.3.1.1$^{3,7}$]dec-1-ylmethyl)-benzamide To dimethylsulfoxide (2 ml) was added sodium hydride (0.033 g, 60% in oil) at room temperature. The mixture was stirred for 5min. at this temperature and a solution of trimethylsulfoxonium iodide (0.178 g) in dimethylsulfoxide (2 ml) was added. After 30 min., 2-chloro-5-[(4-oxo-1-piperidinyl)methyl]-N-(tricyclo[3.3.1.1$^{3,7}$]dec-1-ylmethyl)-benzamide (0.28 g, Example 83a) in dimethylsulfoxide (2 ml) was added and the reaction stirred at room temperature for 3 h before being quenched with ice/water (20 ml). The mixture was extracted three times with ethyl acetate, the combined organic layers washed with brine and dried over magnesium sulfate. The crude material was purified on silica gel, eluting with ethyl acetate to afford the subtitle compound as a white foam (0.25 g).

MS (APCI+ve) 429/431 (M+H)$^+$ $^1$H NMR (CDCl$_3$) δ 7.68 (1H, s); 7.40–7.30 (2H, m); 6.27 (1H, t); 3.54 (2H, s); 3.18 (2H, d); 2.70–2.50 (6H, m); 2.00 (s, 3H); 1.90–1.75 (2H, m); 1.74 (3H, d); 1.66 (3H, d); 1.59 (6H, bs); 1.80–1.50 (m, 2H).

b) 2-Chloro-5-[[4-hydroxy-4-[[(1-methylethyl)amino]methyl]-1-piperidinyl]methyl]-N-(tricyclo[3.3.1.1$^{3,7}$]dec-1-ylmethyl)-benzamide In a sealed tube 2-chloro-5-(1-oxa-6-azaspiro[2.5]oct-6-ylmethyl)-N-(tricyclo[3.3.1.1$^{3,7}$]dec-1-ylmethyl)-benzamide (Example 84a, 0.15 g) was dissolved in a mixture of ethanol (4 ml) and di-isopropylamine (1 ml) and heated at 65° C. for 14 h. The volatiles were removed under vacuum and the residue purified on silica gel (5% 7N ammonia in methanol/95% dichloromethane) to afford the title compound as a white solid (0.115 g).

MS (APCI+ve) 488/490 (M+H)$^+$ $^1$H NMR (CD$_3$OD) δ 7.45–7.35 (3H, m); 3.55 (2H, s); 3.06 (2H, s); 2.76 (1H, q); 2.70–2.55 (2H, m); 2.54 (2H, s); 2.50–2.35 (2H, m); 1.99 (s, 3H); 1.77 (3H, d); 1.70 (3H, d); 1.63 (10H, bs); 1.07 (m, 2H).

EXAMPLE 85

2-Chloro-5-[(1,2,3,6-tetrahydro-3-pyridinyl)methyl]-N-(tricyclo[3.3.1.1$^{3,7}$]dec-1-ylmethyl)-benzamide, hydrochloride salt

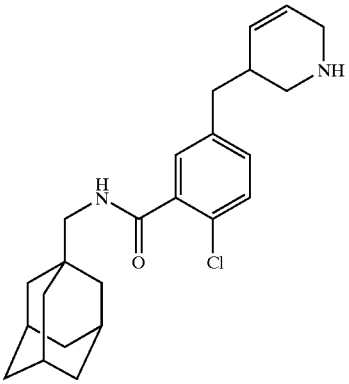

To pyridine (6 ml) at 0° C. was added portionwise lithium aluminium hydride (0.24 g). The mixture was allowed to warm to room temperature and was stirred for 24 h. Lithium iodide (0.220 g) and pyridine (1 ml) were added and the reaction stirred for a further 1 h. 5-Bromomethyl-2-chloro-N-(tricyclo[3.3.1.1$^{3,7}$]dec-1-ylmethyl)-benzamide (0.30 g, Example 8b) in dry pyridine (2 ml) was added to the solution at room temperature. After 2 h, the mixture was quenched at 0° C. with a cold 15% aqueous solution of acetic acid, stirred for an hour and concentrated under vacuum. The residue was taken in 1N sodium hydroxide, extracted with dichloromethane and the organic layers dried over magnesium sulfate. The crude material was purified on silicagel (2 to 10% 7N ammonia in methanol/dichloromethane) then treated with a 4N solution of hydrogen chloride in dioxane and methanol to give the title compound (0.20 g).

MS (APCI+ve) 399/401 (M+H)$^+$ $^1$H NMR (CD$_3$OD) δ 8.42 (1H, t); 7.43 (1H, dd); 7.32 (1H, dd); 7.30 (d; 1H); 5.89 (1H, d); 5.80 (1H, d); 3.64 (2H, s); 3.40–3.30 (1H, m); 3.06 (4H, d); 1.99 (s, 3H); 1.78 (3H, d); 1.68 (3H, d); 1.63 (6H, d).

EXAMPLE 86

2-Chloro-5-(3-piperidinylmethyl)-N-(tricyclo[3.3.1.1$^{3,7}$]dec-1-ylmethyl)-benzamide, acetate salt

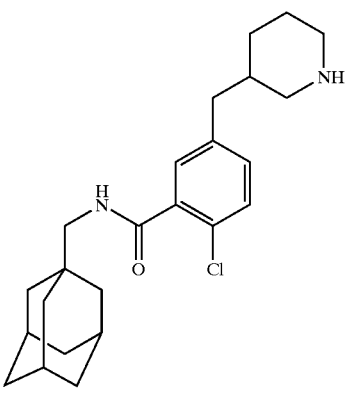

a) 2-Chloro-5-(3-piperidinylmethyl)-N-(tricyclo[3.3.1.1$^{3,7}$]dec-1-ylmethyl)-benzamide, acetate salt To pyridine (12 ml) at 0° C. was added portionwise lithium aluminium hydride (0.46 g). The mixture was allowed to warm to room temperature and was stirred for 24 h. Lithium iodide (0.44 g) and pyridine (5 ml) were added and the reaction stirred for a further 1 h. The solution was cooled to −10° C. and 5-bromomethyl-2-chloro-N-(tricyclo[3.3.1.1$^{3,7}$]dec-1-ylmethyl)-benzamide (Example 8b, 0.5 g) in dry pyridine (5 ml) added. After 1 hour, the mixture was quenched at −10 degrees with cold water, then 1N sodium hydroxide. The solution was stirred for 1 h then concentrated under vacuum. The residue was taken in water, extracted with dichloromethane and the organic layers dried over magnesium sulfate. The crude material was purified on silica gel (ethylacetate: i-hexane/4:1) to afford the subtitle compound as a white foam (0.355 g).

b) 2-Chloro-5-(3-piperidinylmethyl)-N-(tricyclo[3.3.1.1$^{3,7}$]dec-1-ylmethyl)-benzamide, acetate salt 2-Chloro-5-(3-pyridinylmethyl)-N-(tricyclo[3.3.1.1$^{3,7}$]dec-1-ylmethyl)-benzamide (0.10 g, Example 86a) was dissolved in methanol and treated with a 4N solution of hydrogen chloride in dioxane. The hydrochloride salt was isolated and hydrogenated in ethanol over platinum oxide following the procedure described in Example 51 to give the title compound as the acetate salt after purification by reverse phase HPLC (0.1% aqueous ammonium acetate/acetontrile) (0.053 g).

MS (APCI+ve) 401/403 (M+H)$^+$ $^1$H NMR (CD$_3$OD) δ 7.42 (1H, d); 7.31–7.25 (2H, m); 3.38–3.28 (1H; m); 3.28–3.18 (1H; 2m); 3.07 (2H, s); 2.86 (1H, dt); 2.72–2.61 (1H, m); 2.65 (1H, d); 2.13–2.05 (1H; m); 2.01 (3H, s); 1.94 (3H, s); 1.90–1.85 (1H; m); 1.85–1.60 (2H; m); 1.80 (3H, d); 1.71 (3H, d); 1.64 (6H, d); 1.29 (1H, qd).

EXAMPLE 87

2-bromo-5-[[4-[(2-hydroxyethyl)amino]-1-piperidinyl]methyl]-N-(tricyclo[3.3.1.1$^{3,7}$]dec-1-ylmethyl-benzamide

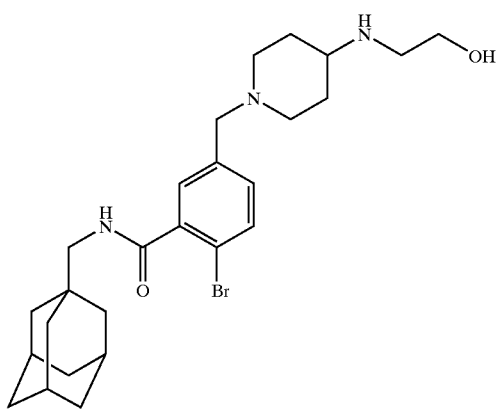

Prepared according to the procedures described in Example 83a and 83b from 2-bromo-5-bromomethyl-N-(tricyclo[3.3.1.1$^{3,7}$]dec-1-ylmethyl)-benzamide (Example 65a), 4-piperidone and ethanolamine.

MS (APCI+ve) MW 505/506 (M+H)$^+$ $^1$H NMR (CDCl$_3$) δ 7.53 (1H, d); 7.52 (1H, d); 7.26 (1H, dd); 6.05 (1H; t); 3.65 (2H; t); 3.46 (2H, s); 3.17 (2H, d); 2.82 (2H, t); 2.60–2.45 (1H, m); 2.20–1.95 (7H; m) 1.95–1.82 (2H, bd); 1.75 (3H, d); 1.66 (3H, d); 1.61 (6H, d); 1.50–1.35 (2H, qd).

EXAMPLE 88

2-Chloro-5-[(E)-3-piperidinylidenemethyl]-N-(tricyclo[3.3.1.1$^{3,7}$]dec-1-ylmethyl)-benzamide

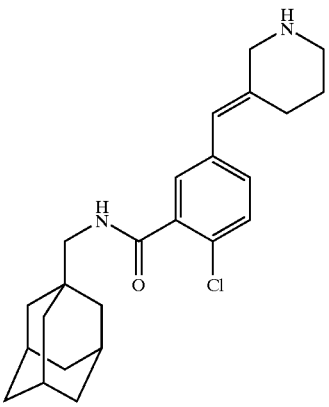

a) 2-Chloro-5-[(E)-(5,6-dihydro-3(4H)-pyridinylidene)methyl]-N-(tricyclo[3.3.1.1$^{3,7}$]dec-1-ylmethyl)-benzamide 2-Chloro-5-formyl-N-(tricyclo[3.3.1.1$^{3,7}$]dec-1-ylmethyl)-benzamide (0.152 g, Example 31a) and 2,3,4,5-tetrahydropyridine trimer (Org. Synth., 1977, Vol.56, 118–122, 0.038 g) were dissolved in methanol (3 ml) and heated at reflux for 4 h. The mixture was evaporated under reduced pressure then purified by HPLC eluting a gradient of 0–5% ethanol in dichloromethane to give the subtitle compound as a white foam (0.046 g).

MS (APCI+ve) 397 (M+H)$^+$ $^1$H NMR (CD$_3$OD) δ 7.98 (1H, s); 7.51 (3H, s); 6.83 (1H, s); 3.66–3.62 (2H, m); 3.07 (2H, s); 2.78–2.73 (2H, m); 1.99 (3H, bs); 1.73 (6H, q); 1.77–1.69 (2H, m); 1.64 (6H, s).

b) 2-Chloro-5-[(E)-3-piperidinylidenemethyl]-N-(tricyclo[3.3.1.1$^{3,7}$]dec-1-ylmethyl)-benzamide Sodium borohydride (0.009 g) in methanol (0.5 ml) was added to a solution of 2-chloro-5-[(E)-(5,6-dihydro-3(4H)-pyridinylidene)methyl]-N-(tricyclo[3.3.1.1$^{3,7}$]dec-1-ylmethyl)-benzamide (0.046 g, Example 88a,) in methanol (1.5 ml). The reaction mixture was stirred for 4 h under an atmosphere of nitrogen at room temperature. Concentrated hydrochloric acid (0.01 ml) was added and the mixture was evaporated under reduced pressure. An aqueous solution of sodium hydroxide (2M, 2 ml) was added to rebasify the residue followed by water (10 ml) and dichloromethane (10 ml). The layers were partitioned and the aqueous layer was extracted further with dichloromethane (2×10 ml). The organic extracts were combined, dried over anhydrous magnesium sulfate, filtered and concentrated under reduced pressure to give the title compound as a white powder (0.024 g).

MS (APCI+ve) 399 (M+H)$^+$ $^1$H NMR (CD$_3$OD) δ 7.43 (1H, d); 7.29–7.26 (2H, m); 6.38 (1H, s); 3.45 (2H, s); 3.07 (2H, s); 2.96 (2H, t); 2.55 (2H, t); 2.00 (3H, bs); 1.75 (6H, q); 1.81–1.64 (2H, m); 1.64 (6H, s).

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of Examples 1 to 88 was tested for antagonist activity at the P2X$_7$ receptor. Thus, the test was performed in 96-well flat bottomed microtitre plates, the wells being filled with 250 μl of test solution comprising 200 μl of a suspension of THP-1 cells ($2.5 \times 10^6$ cells/ml) containing $10^{-4}$M ethidium bromide, 25 μl of a high potassium buffer solution containing $10^{-5}$M bbATP, and 25 μl of the high potassium buffer solution containing $3 \times 10^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of Examples 1 to 88 demonstrated antagonist activity, having a pIC$_{50}$ figure >4.50.

What is claimed is:

1. A compound of formula

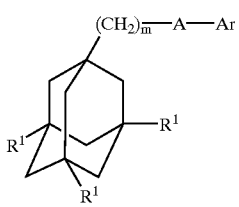

(I)

wherein m represents 1, 2 or 3;

each R$^1$ independently represents a hydrogen or halogen atom;

A represents C(O)NH or NHC(O);

Ar represents a group

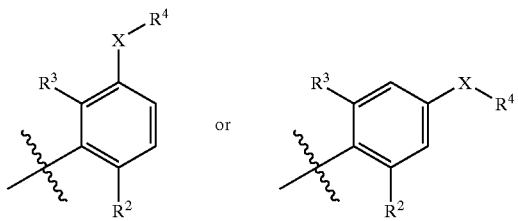

or

X represents a bond, an oxygen atom or a group CO, (CH$_2$)$_{1-6}$, CH=, (CH$_2$)$_{1-6}$O, O(CH$_2$)$_{1-6}$, O(CH$_2$)$_{2-6}$O, O(CH$_2$)$_{2-3}$O(CH$_2$)$_{1-3}$, CR'(OH), (CH$_2$)$_{1-3}$O(CH$_2$)$_{1-3}$, (CH$_2$)$_{1-3}$O(CH$_2$)$_{2-3}$O, NR$^5$, (CH$_2$)$_{1-6}$NR$^5$, NR$^5$(CH$_2$)$_{1-6}$, (CH$_2$)$_{1-3}$NR$^5$(CH$_2$)$_{1-3}$, O(CH$_2$)$_{2-6}$NR$^5$, O(CH$_2$)$_{2-3}$NR$^5$(CH$_2$)$_{1-3}$, (CH$_2$)$_{1-3}$NR$^5$(CH$_2$)$_{2-3}$O, NR$^5$(CH$_2$)$_{2-6}$O, NR$^5$(CH$_2$)$_{2-3}$O (CH$_2$)$_{1-3}$, CONR$^5$, NR$^5$CO, S(O)$_n$, S(O)$_n$CH$_2$, CH$_2$S(O)$_n$, SO$_2$NR$^5$ or NR$^5$SO$_2$;

n is 0, 1 or 2;

R' represents a hydrogen atom or a C$_1$–C$_6$ alkyl group;

one of R$^2$ and R$^3$ represents a halogen, cyano, nitro, amino, hydroxyl, or a group selected from (i) C$_1$–C$_6$ alkyl optionally substituted by at least one C$_3$–C$_6$ cycloalkyl, (ii) C$_3$–C$_8$ cycloalkyl, (iii) C$_1$–C$_6$ alkyloxy optionally substituted by at least one C$_3$–C$_6$ cycloalkyl, and (iv) C$_3$–C$_8$ cycloalkyloxy, each of these groups being optionally substituted by one or more fluorine atoms, and the other of R$^2$ and R$^3$ represents a hydrogen or halogen atom;

either R$^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, C$_1$–C$_6$ alkyl, C$_1$–C$_6$ hydroxyalkyl, —NR$^6$R$^7$, —(CH$_2$)$_r$NR$^6$R$^7$ and CONR$^6$R$^7$, r is 1, 2, 3, 4, 5 or 6;

R$^5$ represents a hydrogen atom or a C$_1$–C$_6$ alkyl or C$_3$–C$_8$ cycloalkyl group;

R$^6$ and R$^7$ each independently represent a hydrogen atom or a C$_1$–C$_6$ alkyl, C$_2$–C$_6$ hydroxyalkyl or C$_3$–C$_8$ cycloalkyl group, or R$^6$ and R$^7$ together with the nitrogen atom to which they are attached form a 3- to 8-membered saturated heterocyclic ring; with the provisos that, (a) when A represents C(O)NH and R$^4$ represents an unsubstituted 3- to 8-membered saturated aliphatic heterocyclic ring system containing one nitrogen atom, then X is other than a bond, and (b) when A represents C(O)NH and X represents a group (CH$_2$)$_{1-6}$ or O(CH$_2$)$_{1-6}$, then R$^4$ does not represent an unsubstituted imidazolyl, unsubstituted morpholinyl, unsubstituted piperidinyl or unsubstituted pyrrolidinyl group, and (c) when A represents NHC(O) and R$^4$ represents an unsubstituted 3- to 8-membered saturated aliphatic heterocyclic ring system containing one nitrogen atom, then X is other than a bond, and (d) when A represents NHC(O) and X represents O(CH$_2$)$_{1-6}$, NH(CH$_2$)$_{1-6}$ or SCH$_2$, then R$^4$ does not represent an unsubstituted 1-piperidinyl or unsubstituted 1-pyrrolidinyl group, and (e) when A represents NHC(O) and X represents O(CH$_2$)$_{2-3}$NH(CH$_2$)$_2$, then R$^4$ does not represent an imidazolyl group;

or a pharmaceutically acceptable salt or solvate thereof.

2. A compound according to claim 1, wherein A represents NHC(O).

3. A compound according to claim 1, wherein Ar represents a group

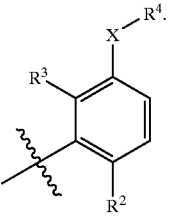

4. A compound according to an claim 1, wherein X represents a bond, an oxygen atom or a group CO, (CH$_2$)$_{1-6}$, CH=, O(CH$_2$)$_{1-6}$, O(CH$_2$)$_{2-6}$O, O(CH$_2$)$_{2-3}$O(CH$_2$)$_{1-3}$, CR'(OH), NR$^5$, (CH$_2$)$_{1-6}$NR$^5$, CONR$^5$, S(O)$_n$ or S(O)$_n$CH$_2$.

5. A compound according to claim 1, wherein $R^4$ represents a 3- to 9-membered saturated or unsaturated aliphatic heterocyclic ring system containing one or two nitrogen atoms and optionally an oxygen atom, the heterocyclic ring system being optionally substituted by one or two substituents independently selected from hydroxyl, $C_1$–$C_6$alkyl, $C_1$–$C_6$hydroxyalkyl, —$NR^6R^7$ and —$(CH_2)_rNR^6R^7$.

6. A compound according to claim 1, wherein $R^4$ represents a group selected from:

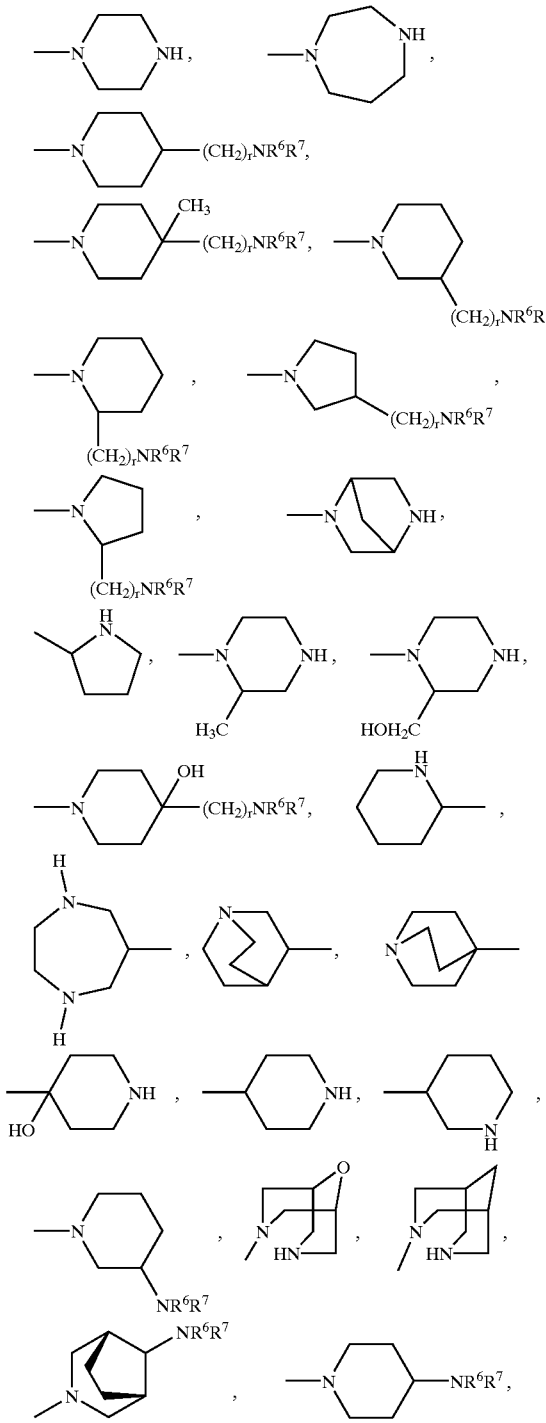

-continued

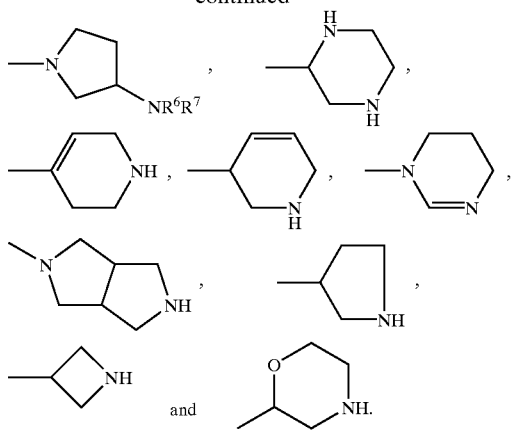

and

7. A compound of formula (I), or a pharmaceutically acceptable salt or solvate thereof, according to claim 1 being:

2-Nitro-3-piperazin-1-yl-N-(tricyclo[3.3.1.1$^{3,7}$]dec-1-ylmethyl)-benzamide,
2-Amino-3-piperazin-1-yl-N-(tricyclo[3.3.1.1$^{3,7}$]dec-1-ylmethyl)-benzamide, dihydrochloride salt,
2-Chloro-3-piperazin-1-yl-N-(tricyclo[3.3.1.1$^{3,7}$]dec-1-ylmethyl)-benzamide,
2-Chloro-5-piperazin-1-yl-N-(tricyclo[3.3.1.1$^{3,7}$]dec-1-ylmethyl)-benzamide,
2-Chloro-5-(hexahydro-1H-1,4-diazepin-1-yl)-N-(tricyclo[3.3.1.1$^{3,7}$]dec-1-ylmethyl)-benzamide, hydrochloride salt,
5-(4-Amino-1-piperidinyl)-2-chloro-N-(tricyclo[3.3.1.1$^{3,7}$]dec-1-ylmethyl)-benzamide, hydrochloride salt,
(+/−)-5-(3-Amino-1-pyrrolidinyl)-2-chloro-N-(tricyclo[3.3.1.1$^{3,7}$]dec-1-ylmethyl)-benzamide, hydrochloride salt,
2-Chloro-5-piperazin-1-ylmethyl-N-(tricyclo[3.3.1.1$^{3,7}$]dec-1-ylmethyl)-benzamide, hydrochloride salt,
2-Chloro-5-[(hexahydro-1H-1,4-diazepin-1-yl)methyl]-N-(tricyclo[3.3.1.1$^{3,7}$]dec-1-ylmethyl)-benzamide, hydrochloride salt,
5-[(4-Amino-1-piperidinyl)methyl]-2-chloro-N-(tricyclo[3.3.1.1$^{3,7}$]dec-1-ylmethyl)-benzamide, hydrochloride salt,
5-[(3-Amino-1-pyrrolidinyl)methyl]-2-chloro-N-(tricyclo[3.3.1.1$^{3,7}$]dec-1-ylmethyl)-benzamide, hydrochloride salt,
2-Chloro-5-(4-piperidinyloxy)-N-(tricyclo[3.3.1.1$^{3,7}$]dec-1-ylmethyl)-benzamide, hydrochloride salt,
(R)-2-Chloro-5-(2-pyrrolidinylmethoxy)-N-(tricyclo[3.3.1.1$^{3,7}$]dec-1-ylmethyl)-benzamide, hydrochloride salt,
(S)-2-Chloro-5-(2-pyrrolidinylmethoxy)-N-(tricyclo[3.3.1.1$^{3,7}$]dec-1-ylmethyl)-benzamide, hydrochloride salt,
2-Chloro-5-(3-piperidinylmethoxy)-N-(tricyclo[3.3.1.1$^{3,7}$]dec-1-ylmethyl)-benzamide, hydrochloride salt,
cis-5-[(4-Aminocyclohexyl)oxy]-2-chloro-N-(tricyclo[3.3.1.1$^{3,7}$]dec-1-ylmethyl)-benzamide, hydrochloride salt,
2-Methyl-5-(1-piperazinylmethyl)-N-(tricyclo[3.3.1.1$^{3,7}$]dec-1-ylmethyl)-benzamide, hydrochloride salt,
2-Chloro-5-(1-piperazinylmethyl)-N-(2-tricyclo[3.3.1.1$^{3,7}$]dec-1-ylethyl)-benzamide, hydrochloride salt,
(+/−)-2-Chloro-5-(3-pyrrolidinyloxy)-N-(tricyclo[3.3.1.1$^{3,7}$]dec-1-ylmethyl)-benzamide, hydrochloride salt, (+/−)-2-Chloro-5-(3-piperidinyloxy)-N-(tricyclo[3.3.1.1$^{3,7}$]dec-1-ylmethyl)-benzamide, hydrochloride salt, trans-5-[(4-Aminocyclohexyl)oxy]-2-chloro-N-(tricyclo[3.3.1.1$^{3,7}$]dec-1-ylmethyl)-benzamide, cis-(+/−)-5-[(3-Aminocyclopentyl)oxy]-2-chloro-N-(tricyclo[3.3.1.1$^{3,7}$]dec-1-ylmethyl)-benzamide, (S,S)-2-Chloro-5-(2,5-diazabicyclo[2.2.1]hept-2-yl)-N-(tricyclo[3.3.1.1$^{3,7}$]dec-1-ylmethyl)-benzamide, hydrochloride salt, 2-Chloro-5-(2-methyl-1-piperazinyl)-N-(tricyclo[3.3.1.1$^{3,7}$]dec-1-ylmethyl)-benzamide, hydrochloride salt, (+/−)-2-Chloro-5-(3-pyrrolidinylamino)-N-(tricyclo[3.3.1.1$^{3,7}$]dec-1-ylmethyl)-benzamide, hydrochloride salt, (+/−)-5-(3-Amino-1-piperidinyl)-2-chloro-N-(tricyclo[3.3.1.1$^{3,7}$]dec-1-ylmethyl)-benzamide, (+/−)-2-Chloro-5-(3-piperidinylamino)-N-(tricyclo[3.3.1.1$^{3,7}$]dec-1-ylmethyl)-benzamide, 2-Chloro-5-[hexahydropyrrolo[3,4-c]pyrrol-2(1H)-yl]-N-(tricyclo[3.3.1.1$^{3,7}$]dec-1-ylmethyl)-benzamide, N-[2-methyl-5-(4-piperidinyloxy)phenyl]-tricyclo[3.3.1.1$^{3,7}$]decane-1-acetamide, hydrochloride salt, N-[2-chloro-5-(4-piperidinyloxy)phenyl]-tricyclo[3.3.1.1$^{3,7}$]decane-1-acetamide, hydrochloride salt, 2-Chloro-5-[(4-piperidinylamino)methyl]-N-(tricyclo[3.3.1.1$^{3,7}$]dec-1-ylmethyl)-benzamide, dihydrochloride salt, 5-[[[4-(Aminomethyl)cyclohexyl]amino]methyl]-2-chloro-N-(tricyclo[3.3.1.1$^{3,7}$]dec-1-ylmethyl)-benzamide, dihydrochloride salt, 5-[[(4-Aminocyclohexyl)amino]methyl]-2-chloro-N-(tricyclo[3.3.1.1$^{3,7}$]dec-1-ylmethyl)-benzamide, dihydrochloride salt, 5-[(1-Azabicyclo[2.2.2]oct-3-ylamino)methyl]-2-chloro-N-(tricyclo[3.3.1.1$^{3,7}$]dec-1-ylmethyl)-benzamide, N-[4-(3-Aminopyrrolidin-1-yl)-2-methylphenyl]-2-(tricyclo[3.3.1.1$^{3,7}$]dec-1-yl)acetamide, dihydrochloride salt, N-(2-Methyl-4-piperazin-1-ylphenyl)-2-(tricyclo[3.3.1.1$^{3,7}$]dec-1-yl)acetamide, dihydrochloride salt, cis-4-(3-Amino-cyclopentyloxy)-2-chloro-N-(tricyclo[3.3.1.1$^{3,7}$]dec-1-ylmethyl)-benzamide, hydrochloride salt, 2-Chloro-4-(4-piperidinyloxy)-N-(tricyclo[3.3.1.1$^{3,7}$]dec-1-ylmethyl)-benzamide, hydrochloride salt, (+/−)-2-Chloro-4-(pyrrolidin-3-yloxy)-N-(tricyclo[3.3.1.1$^{3,7}$]dec-1-ylmethyl)-benzamide, 2-Chloro-4-(piperidin-3-yloxy)-N-(tricyclo[3.3.1.1$^{3,7}$]dec-1-ylmethyl)-benzamide, hydrochloride salt, 2-Chloro-4-(4-piperazin-1-yl)-N-(tricyclo[3.3.1.1$^{3,7}$]dec-1-ylmethyl)-benzamide, hydrochloride salt, 2-Chloro-4-(3-pyrrolidinylamino)-N-(tricyclo[3.3.1.1$^{3,7}$]dec-1-ylmethyl)-benzamide, hydrochloride salt, 2-Chloro-4-(hexahydro-1H-1,4-diazepin-1-yl)-N-(tricyclo[3.3.1.1$^{3,7}$]dec-1-ylmethyl)-benzamide, hydrochloride salt, (±)-5-[(3-Amino-1-piperidinyl)methyl]-2-chloro-N-(tricyclo[3.3.1.1$^{3,7}$]dec-1-ylmethyl)-benzamide, hydrochloride salt, 2-Chloro-5-(2,5-diazabicyclo[2.2.1]hept-2-ylmethyl)-N-(tricyclo[3.3.1.1$^{3,7}$]dec-1-ylmethyl)-benzamide, hydrochloride salt, 2-Chloro-5-(9-oxa-3,7-diazabicyclo[3.3.1]non-3-ylmethyl)-N-(tricyclo[3.3.1.1$^{3,7}$]dec-1-ylmethyl)-benzamide, hydrochloride salt, 2-Chloro-5-(3,7-diazabicyclo[3.3.1.1]non-3-ylmethyl)-N-(tricyclo[3.3.1.1$^{3,7}$]dec-1-ylmethyl)-benzamide, hydrochloride salt, trans-2-Chloro-5-[[8-(methylamino)-3-azabicyclo[3.2.1]oct-3-yl]methyl]-N-(tricyclo[3.3.1.1$^{3,7}$]dec-1-ylmethyl)-benzamide, hydrochloride salt, cis-2-Chloro-5-[(hexahydropyrrolo[3,4-c]pyrrol-2(1H)-yl)methyl]-N-(tricyclo[3.3.1.1$^{3,7}$]dec-1-ylmethyl)-benzamide, hydrochloride salt, 2-Chloro-5-(4-piperidinylidenemethyl)-N-(tricyclo[3.3.1.1$^{3,7}$]dec-1-ylmethyl)-benzamide, hydrochloride salt, 2-Chloro-5-(4-piperidinylmethyl)-N-(tricyclo[3.3.1.1$^{3,7}$]dec-1-ylmethyl)-benzamide, hydrochloride salt, 2-Chloro-5-(4-hydroxy-piperidin-4-yl)-N-(tricyclo[3.3.1.1$^{3,7}$]dec-1-ylmethyl)-benzamide, hydrochloride salt, 2-Chloro-5-(1,2,3,6-tetrahydro-pyridin-4-yl)-N-(tricyclo[3.3.1.1$^{3,7}$]dec-1-ylmethyl)-benzamide, hydrochloride salt, 2-Ethyl-5-piperazin-1-ylmethyl-N-(tricyclo[3.3.1.1$^{3,7}$]dec-1-ylmethyl)-benzamide, hydrochloride salt, 2-Chloro-5-(piperidin-4-ylsulfanyl)-N-(tricyclo[3.3.1.1$^{3,7}$]dec-1-ylmethyl)-benzamide, hydrochloride salt, 2-Chloro-5-(piperidin-4-ylsulfinyl)-N-(tricyclo[3.3.1.1$^{3,7}$]dec-1-ylmethyl)-benzamide, 2-Chloro-5-(piperidin-4-ylsulfonyl)-N-(tricyclo[3.3.1.1$^{3,7}$]dec-1-ylmethyl)-benzamide, hydrochloride salt, 2-Chloro-5-(piperidin-4-ylmethylsulfanyl)-N-(tricyclo[3.3.1.1$^{3,7}$]dec-1-ylmethyl)-benzamide, hydrochloride salt, 2-Chloro-5-(piperidin-4-ylmethanesulfonyl)-N-(tricyclo[3.3.1.1$^{3,7}$]dec-1-ylmethyl)-benzamide, hydrochloride salt, 2-Chloro-5-(piperazine-1-carbonyl)-N-(tricyclo[3.3.1.1$^{3,7}$]dec-1-ylmethyl)-benzamide, hydrochloride salt, 2-Chloro-5-([1,4]diazepane-1-carbonyl)-N-(tricyclo[3.3.1.1$^{3,7}$]dec-1-ylmethyl)-benzamide, hydrochloride salt, 4-Chloro-N$^1$-(piperidin-4-yl-)-N$^2$-(tricyclo[3.3.1.1$^{3,7}$]dec-1-ylmethyl)-isophthalamide, hydrochloride salt, 2-Chloro-5-(hydroxy-4-piperidinylmethyl)-N-(tricyclo[3.3.1.1$^{3,7}$]dec-1-ylmethyl)-benzamide, hydrochloride salt, (±)-2-Chloro-5-(hydroxy-3-piperidinylmethyl)-N-(tricyclo[3.3.1.1$^{3,7}$]dec-1-ylmethyl)-benzamide, hydrochloride salt, 2-Bromo-5-piperazin-1-ylmethyl-N-(tricyclo[3.3.1.1$^{3,7}$]dec-1-ylmethyl)-benzamide, hydrochloride salt, 2-Chloro-5-[2-(1-piperazinyl)ethyl]-N-(tricyclo[3.3.1.1$^{3,7}$]dec-1-ylmethyl)-benzamide, hydrochloride salt, 2-Chloro-5-[2-(2,5-diazabicyclo[2.2.1]hept-2-yl)ethyl]-N-(tricyclo[3.3.1.1$^{3,7}$]dec-1-ylmethyl)-benzamide, hydrochloride salt, 5-[2-(4-Amino-1-piperidinyl)ethyl]-2-chloro-N-(tricyclo[3.3.1.1$^{3,7}$]dec-1-ylmethyl)-benzamide, hydrochloride salt, 2-Chloro-5-[2-(3-piperidinylamino)ethyl]-N-(tricyclo[3.3.1.1$^{3,7}$]dec-1-ylmethyl)-benzamide, dihydrochloride salt, 5-[2-(3-Amino-1-piperidinyl)ethyl]-2-chloro-N-(tricyclo[3.3.1.1$^{3,7}$]dec-1-ylmethyl)benzamide, hydrochloride salt, 2-Chloro-5-[2-(3-pyrrolidinylamino)ethyl]-N-(tricyclo[3.3.1.1$^{3,7}$]dec-1-ylmethyl)-benzamide, dihydrochloride salt, 5-[2-[(3R)-3-Aminopyrrolidinyl]ethyl]-2-chloro-N-(tricyclo[3.3.1.1$^{3,7}$]dec-1-ylmethyl)-benzamide, hydrochloride salt, 2-Chloro-5-[2-[2-(hydroxymethyl)-1-piperazinyl]ethyl]-N-(tricyclo[3.3.1.1$^{3,7}$]dec-1-ylmethyl)-benzamide, hydrochloride salt, 2-Chloro-5-(hexahydro-1H-1,4-diazepin-1-yl)-N-(2-tricyclo[3.3.1.1$^{3,7}$]dec-1-ylethyl)-benzamide, hydrochloride salt, (+/−)-5-(3-Amino-1-pyrrolidinyl)-2-chloro-N-(2-tricyclo[3.3.1.1$^{3,7}$]dec-1-ylethyl)-benzamide, hydrochloride salt, 2-Chloro-5-(4-piperidinylcarbonyl)-N-(tricyclo[3.3.1.1$^{3,7}$]dec-1-ylmethyl)-benzamide, hydrochloride salt, 2-Chloro-5-[1-hydroxy-1-(4-piperidinyl)ethyl]-N-(tricyclo[3.3.1.1$^{3,7}$]dec-1-ylmethyl)-benzamide, hydrochloride salt, 2-Chloro-5-[2-(1-piperazinyl)ethoxy)-N-(tricyclo[3.3.1.1$^{3,7}$]dec-1-ylmethyl)-benzamide, hydrochloride salt, 2-Chloro-5-[2-(4-piperidinyl)ethoxy)-N-(tricyclo[3.3.1.1$^{3,7}$]dec-1-ylmethyl)-benzamide, hydrochloride salt, 2-Chloro-5-[2-(4-piperidinyloxy)ethoxy)-N-(tricyclo[3.3.1.1$^{3,7}$]dec-1-ylmethyl)-benzamide, hydrochloride salt, 2-Chloro-5-[2-[2-(1-piperazinyl)ethoxy]ethoxy]-N-(tricyclo[3.3.1.1$^{3,7}$]dec-1-ylmethyl)-benzamide, hydrochloride salt, 2-Chloro-5-[(5,6-dihydro-1(4H)-pyrimidinyl)methyl]-N-(tricyclo[3.3.1.1$^{3,7}$]dec-1-ylmethyl)-benzamide, 2-Chloro-5-[[4-[(2-hydroxyethyl)amino]-1-piperidinyl]methyl]-N-(tricyclo[3.3.1.1$^{3,7}$]dec-1-ylmethyl)-benzamide hydrochloride salt, 2-Chloro-5-[[4-hydroxy4-[[(1-methylethyl)amino]methyl]-1-piperidinyl]methyl]-N-(tricyclo[3.3.1.1$^{3,7}$]dec-1-ylmethyl)-benzamide, 2-Chloro-5-[(1,2,3,6-tetrahydro-3-pyridinyl)methyl]-N-(tricyclo[3.3.1.1$^{3,7}$]dec-1-ylmethyl)-benzamide, hydrochloride salt, 2-Chloro-5-(3-piperidinylmethyl)-N-(tricyclo[3.3.1.1$^{3,7}$]dec-1-ylmethyl)-benzamide, acetate salt, 2-bromo-5-[[4-[(2-hydroxyethyl)amino]-1-piperidinyl]methyl]-N-(tricyclo[3.3.1.1$^{3,7}$]dec-1-ylmethyl-benzamide, or 2-Chloro-5-[(E)-3-piperidinylidenemethyl]-N-(tricyclo[3.3.1.1$^{3,7}$]dec-1-ylmethyl)-benzamide.

8. A process for the preparation of a compound of formula (I)

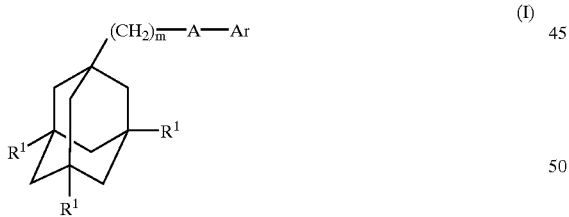

(I)

wherein m, each R$^1$, A and Ar are as defined in claim 1, which comprises:

(i) when X represents a CH$_2$ group, R$^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, C$_1$–C$_6$ alkyl, C$_1$–C$_6$ hydroxyalkyl, —NR$^6$R$^7$, —(CH$_2$)$_r$NR$^6$R$^7$ and —CONR$^6$R$^7$ and R$^4$ is linked to X through a nitrogen atom, reacting a compound of formula

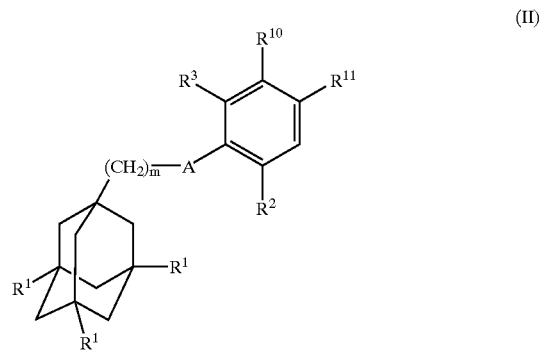

(II)

wherein one of R$^{10}$ and R$^{11}$ represents a hydrogen atom and the other of R$^{10}$ and R$^{11}$ represents a group —CH$_2$L$^1$ in which L$^1$ represents a leaving group and m, A, R$^1$, R$^2$ and R$^3$ are as defined in formula (I), with a compound of formula

R$^{4'}$—H  (III)

in the presence of a base, wherein R$^{4'}$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, C$_1$–C$_6$ alkyl, C$_1$–C$_6$ hydroxyalkyl, —NR$^6$R$^7$, —(CH$_2$)$_r$NR$^6$R$^7$ and —CONR$^6$R$^7$ and wherein R$^6$ and R$^7$ are as defined in formula (I); or (ii) when X represents an oxygen atom or a group O(CH$_2$)$_{1-6}$, O(CH$_2$)$_{2-6}$O, O(CH$_2$)$_{2-3}$O(CH$_2$)$_{1-3}$, O(CH$_2$)$_{2-6}$NR$^5$ or O(CH$_2$)$_{2-3}$NR$^5$(CH$_2$)$_{1-3}$, reacting a compound of formula

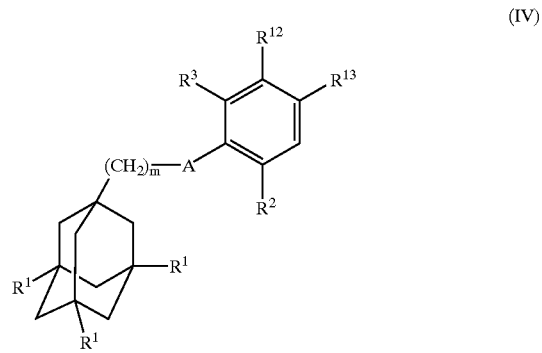

(IV)

wherein one of R$^{12}$ and R$^{13}$ represents a hydrogen atom and the other of R$^{12}$ and R$^{13}$ represents a hydroxyl group and m, A, R$^1$, R$^2$ and R$^3$ are as defined in formula (I), with a compound of formula

R$^4$—Y—OH  (V)

wherein Y represents a bond or a group (CH$_2$)$_{1-6}$, O(CH$_2$)$_{2-6}$, (CH$_2$)$_{1-3}$O(CH$_2$)$_{2-3}$, NR$^5$(CH$_2$)$_{2-6}$ or (CH$_2$)$_{1-3}$NR$^5$(CH$_2$)$_{2-3}$ and R$^4$ is as defined in formula (I), in the presence of 1,1-(azodicarbonyl)dipiperidine and tributylphosphine; or (iii) when X represents a bond, an oxygen atom or a group $O(CH_2)_{1-6}$, $O(CH_2)_{2-6}O$, $O(CH_2)_{2-3}O(CH_2)_{1-3}$, $NR^5$, $NR^5(CH_2)_{1-6}$, $NR^5(CH_2)_{2-6}O$ or $NR^5(CH_2)_{2-3}O(CH_2)_{1-3}$ and A is NHC(O), reacting a compound of formula

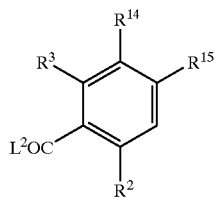
(VI)

wherein one of $R^{14}$ and $R^{15}$ represents a group $-X'-R^4$ and the other of $R^{14}$ and $R^{15}$ represents a hydrogen atom, X' represents a bond, an oxygen atom or a group $O(CH_2)_{1-6}$, $O(CH_2)_{2-6}O$, $O(CH_2)_{2-3}O(CH_2)_{1-3}$, $NR^5$, $NR^5(CH_2)_{1-6}$, $NR^5(CH_2)_{2-6}O$ or $NR^5(CH_2)_{2-3}O(CH_2)_{1-3}$, $L^2$ represents a leaving group and $R^2$, $R^3$, $R^4$ and $R^5$ are as defined in formula (I), with a compound of formula

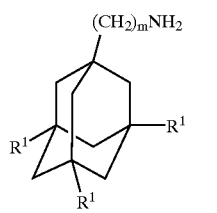
(VII)

wherein m and R are as defined in formula (I), optionally in the presence of a coupling agent; or (iv) when X represents a bond, an oxygen atom or a group $O(CH_2)_{1-6}$, $O(CH_2)_{2-6}O$, $O(CH_2)_{2-3}O(CH_2)_{1-3}$, $NR^5$, $NR^5(CH_2)_{1-6}$, $NR^5(CH_2)_{2-6}O$ or $NR^5(CH_2)_{2-3}O(CH_2)_{1-3}$ and A is C(O)NH, reacting a compound of formula

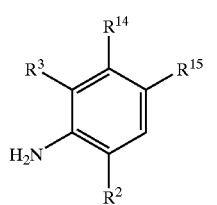
(VIII)

wherein $R^2$ and $R^3$ are as defined in formula (I) and $R^{14}$ and $R^{15}$ are as defined in formula (VI) in (iii) above, with a compound of formula

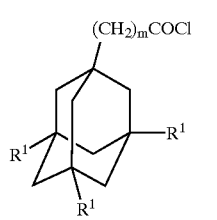
(IX)

wherein m and $R^1$ are as defined in formula (I), in the presence of a base; or (v) when X represents a bond or a group $NR^5$, $NR^5(CH_2)_{1-6}$, $NR^5(CH_2)_{2-6}O$ or $NR^5(CH_2)_{2-3}O(CH_2)_{1-3}$, reacting a compound of formula

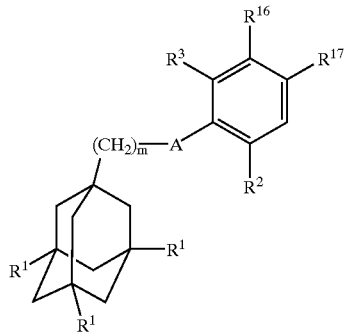
(X)

wherein one of $R^{16}$ and $R^{17}$ represents a leaving group, $L^3$, and the other of $R^{16}$ and $R^{17}$ represents a hydrogen atom and m, A, $R^1$, $R^2$ and $R^3$ are as defined in formula (I), with a compound of formula $R^4-Z$ (XI)

wherein Z represents a hydrogen atom or a group $NHR^5$, $(CH_2)_{1-6}NHR^5$, $O(CH_2)_{2-6}NHR^5$ or a group $(CH_2)_{1-3}O(CH_2)_{2-3}NHR^5$ and $R^4$ and $R^5$ are as defined in formula (I), optionally in the presence of a palladium catalyst, a phosphine ligand and a base; or (vi) when X represents a group $CH_2O$, reacting a compound of formula (II) as defined in (i) above with a compound of formula (V) as defined in (ii) above wherein Y represents a bond, in the presence of a base or in the presence of a metal salt; or (vii) when X represents a group $CH_2NR^5$, reacting a compound of formula (II) as defined in (i) above with a compound of formula (XI) as defined in (v) above wherein Z represents a group $NHR^5$; or (viii) when X represents a group $CH_2O(CH_2)_{1-3}$ or $CH_2O(CH_2)_{2-3}O$, reacting a compound of formula (II) as defined in (i) above with a compound of formula (V) as defined in (ii) above wherein Y represents a group $(CH_2)_{1-3}$ or $O(CH_2)_{2-3}$, in the presence of a base or in the presence of a metal salt; or (ix) when X represents a group $CH_2NR^5CH_2$ or $CH_2NR^5(CH_2)_{2-3}O$ reacting a compound of formula (II) as defined in (i) above with a compound of formula (XI) as defined in (v) above wherein Z represents a group $CH_2NHR^5$ or $O(CH_2)_{2-3}NHR^5$; or (x) when X represents a group $CH_2$ and $R^4$ represents an unsubstituted 4- to 6-membered saturated aliphatic heterocyclic ring system containing one nitrogen atom, reacting a compound of formula (II) as defined in (i) above, with a compound of formula

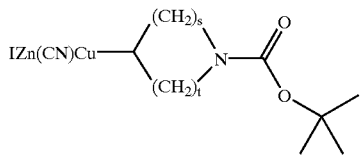
(XII)

wherein s and t independently represent 1 or 2; or (xi) when X represents a group CO, CONR$^5$, NR$^5$CO, SO$_2$, NR$^5$SO$_2$ or SO$_2$NR$^5$ and A is NHC(O), reacting a compound of formula

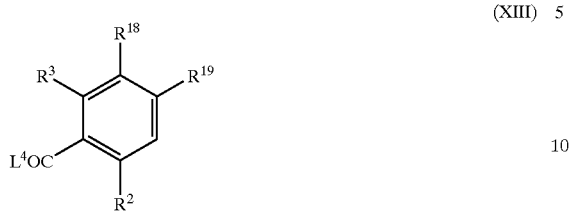

(XIII)

wherein one of R$^{18}$ and R$^{19}$ represents a group —X''—R$^4$ and the other of R$^{18}$ and R$^{19}$ represents a hydrogen atom, X'' represents a group CO, CONR$^5$, NR$^5$CO, SO$_2$, NR$^5$SO$_2$ or SO$_2$NR$^5$, L$^4$ represents a leaving group and R$^2$, R$^3$, R$^4$ and R$^5$ are as defined in formula (I), with a compound of formula (VI) as defined in (iii) above, optionally in the presence of a coupling agent; or (xii) when X represents a group CO, CONR$^5$, NR$^5$CO, SO$_2$, NR$^5$SO$_2$ or SO$_2$NR$^5$ and A is C(O)NH, reacting a compound of formula

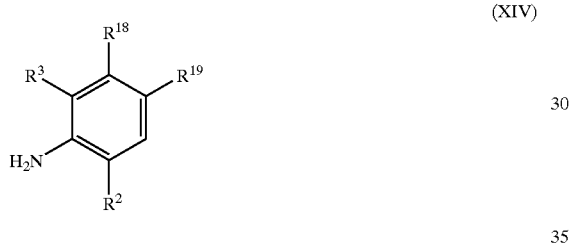

(XIV)

wherein R$^2$ and R$^3$ are as defined in formula (I) and R$^{18}$ and R$^{19}$ are as defined in formula (XIII) in (xi) above, with a compound of formula (IX) as defined in (iv) above, in the presence of a base; or (xiii) when X represents a sulfur atom, reacting a compound of formula (X) as defined in (v) above, with an organolithium reagent and then with a compound of formula

R$^4$—S—SO$_2$—Tol    (XV)

wherein Tol represents a tolyl group and R$^4$ is as defined in formula (I); or (xiv) when X represents a CHOH or CH$_2$ group; reacting a compound of formula (X) as defined in (v) above, with an organolithium reagent and then with a compound of formula

R$^4$—CHO    (XVI)

wherein R$^4$ is as defined in formula (I), optionally followed by a reduction reaction; or (xv) when X represents a bond, reacting a compound of formula (X) as defined in (v) above, with an organolithium reagent and then with a compound of formula

R$^4$=O    (XVII)

wherein R$^4$ is as defined in formula (I), optionally followed by a reduction reaction;

(xvi) when X represents a group SO, oxidising a compound of formula (I) in which X represents a sulphur atom; or (xvii) when X represents a group SCH$_2$, reacting a compound of formula (X) as defined in (v) above, with an organolithium reagent and then with a compound of formula

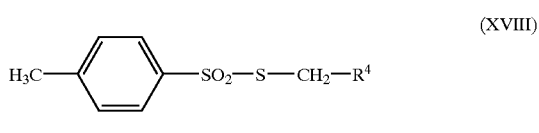

(XVIII)

wherein R$^4$ is as defined in formula (I); or (xviii) when X represents a group SOCH$_2$ or SO$_2$CH$_2$, oxidising a compound of formula (I) in which X represents a group SCH$_2$; or (xix) when X represents a group CH=, reacting a compound of formula (II) as defined in (i) above with trimethylphosphite and then with a compound of formula (XVII) as defined in (xv) above in the presence of a base; or (xx) when X represents a group (CH$_2$)$_{1-6}$, reacting a compound of formula

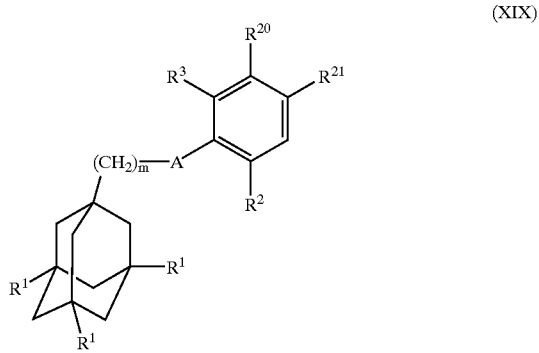

(XIX)

wherein one of R$^{20}$ and R$^{21}$ represents a group CHO or a group (CH$_2$)$_{1-5}$CHO and the other of R$^{20}$ and R$^{21}$ represents a hydrogen atom, and m, A, R$^1$, R$^2$ and R$^3$ are as defined in formula (I), with a compound of formula (XX), R$^4$—H, wherein R$^4$ is as defined in formula (I), in the presence of a reducing agent; or (xxi) when X represents a group (CH$_2$)$_{1-6}$NR$^5$, (CH$_2$)$_{1-3}$NR$^5$(CH$_2$)$_{1-3}$ or (CH$_2$)$_{1-3}$NR$^5$(CH$_2$)$_{2-3}$O, reacting a compound of formula (XIX) as defined in (xx) above, with a compound of formula (XXI), R$^4$—Z', wherein Z' represents a group NHR$^5$, (CH$_2$)$_{1-3}$NHR$^5$, O(CH$_2$)$_{2-3}$NHR$^5$ and R$^4$ and R$^5$ are as defined in formula (I), in the presence of a reducing agent; or (xxii) when X represents a group (CH$_2$)$_{1-3}$O(CH$_2$)$_{1-3}$ or (CH$_2$)$_{1-3}$O(CH$_2$)$_{2-3}$O, reacting a compound of formula (XIX) as defined in (xx) above in which one of R$^{20}$ and R$^{21}$ represents a group CHO or a group (CH$_2$)$_{1-2}$CHO and the other of R$^{20}$ and R$^{21}$ represents a hydrogen atom, with a reducing agent, followed by reaction with a compound of formula (XXII), R$^4$-E, wherein E represents a group (CH$_2$)$_{1-3}$L$^5$ or O(CH$_2$)$_{2-3}$L$^5$, L$^5$ is a leaving group and R$^4$ is as defined in formula (I), in the presence of a base; or (xxiii) when X represents a group (CH$_2$)$_{1-6}$, reacting a compound of formula (II) as defined in (i) above with trimethylphosphite, and then with a compound of formula (XVI) as defined in (xiv) above, or with a compound of formula (XVII) as defined in (xv) above or with a compound of formula (XVIA), $R^4(CH_2)_{1-4}CHO$ in which $R^4$ is as defined in formula (I), in the presence of a base, followed by a reduction reaction; or (xxiv) when X represents a group $(CH_2)_{2-6}O$, reacting a compound of formula

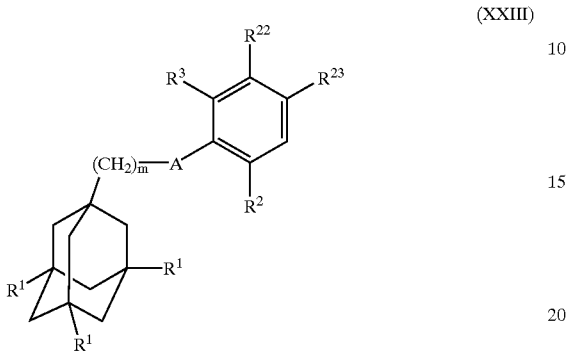

(XXIII)

wherein one of $R^{22}$ and $R^{23}$ represents a group $(CH_2)_{2-6}L^6$ and the other of $R^{20}$ and $R^{21}$ represents a hydrogen atom, $L^6$ represents a leaving group and m, A, $R^1$, $R^2$ and $R^3$ are as defined in formula (I), with a compound of formula (V) as defined in (ii) above in which Y represents a bond; or (xxv) when X represents a group CR'(OH) in which R' is a $C_1$–$C_6$ alkyl group, oxidising a compound of formula (I) in which X represents CH(OH), followed by reaction with a $C_1$–$C_6$ alkyllithium reagent; or (xxvi) when X represents a group $CH_2S$, reacting a compound of formula (II) as defined in (i) above with a compound of formula (XXIV), $R^4$—SH, wherein $R^4$ is as defined in formula (I), in the presence of a base; or (xxvii) when X represents a group $CH_2SO$ or $CH_2SO_2$, oxidising a compound of formula (I) in which X represents a group $CH_2S$; or (xxviii) when X represents a group $CH_2$ and $R^4$ represents a 3-piperidinyl or 2-piperazinyl group, reacting a compound of formula (II) as defined in (i) above with a reagent formed by combining pyridine or pyrazine with an aluminium hydride reagent, followed by a reduction reaction; or (xxix) when X represents a group CH= and $R^4$ represents a 3-piperidinyl group, reacting a compound of formula

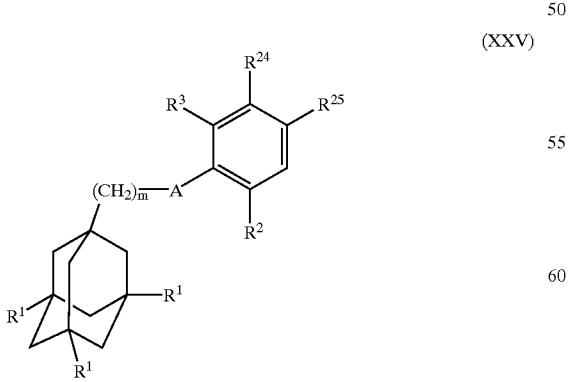

(XXV)

wherein one of $R^{24}$ and $R^{25}$ represents an aldehyde group —CHO, and the other of $R^{24}$ and $R^{25}$ represents a hydrogen atom and m, A, $R^1$, $R^2$ and $R^3$ are as defined in formula (I), with 2,3,4,5-tetrahydropyridine, followed by a reduction reaction; or (xxx) when X represents a bond, $NR^5$ or $NR^5(CH_2)_{1-6}$ and $R^4$ represents a carbon-linked piperidyl or piperazinyl group, reducing a compound of formula

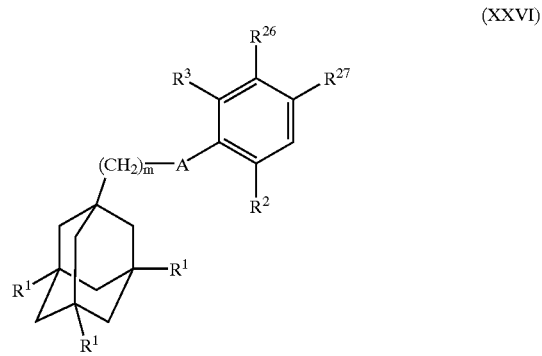

(XXVI)

wherein one of $R^{26}$ and $R^{27}$ represents a pyridyl, pyrazinyl, $NR^5$-pyridyl, $NR^5$-pyrazinyl, $NR^5(CH_2)_{1-6}$-pyridyl or $NR^5(CH_2)_{1-6}$-pyrazinyl group and the other of $R^{26}$ and $R^{27}$ represents a hydrogen atom, and m, A, $R^1$, $R^2$ and $R^3$ are as defined in formula (I), with a source of hydrogen and a hydrogenation catalyst; or (xxxi) when X represents a group $CH_2O(CH_2)_{1-3}$ or $CH_2O(CH_2)_{2-3}O$ and A is NHC(O), reacting a compound of formula

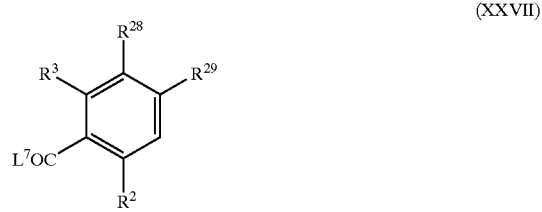

(XXVII)

wherein one of $R^{28}$ and $R^{29}$ represents a group —X'''—$R^4$ and the other of $R^{28}$ and $R^{29}$ represents a hydrogen atom, X''' represents a group $CH_2O(CH_2)_{1-3}$ or $CH_2O(CH_2)_{2-3}O$, $L^7$ represents a leaving group and $R^2$, $R^3$ and $R^4$ are as defined in formula (I), with a compound of formula (VII) as defined in (iii) above, optionally in the presence of a coupling agent; or (xxxii) when X represents a group $CH_2O(CH_2)_{1-3}$ or $CH_2O(CH_2)_{2-3}O$ and A is C(O)NH, reacting a compound of formula

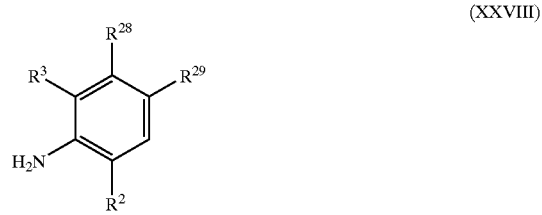

(XXVIII)

wherein $R^2$ and $R^3$ are as defined in formula (I) and $R^{28}$ and $R^{29}$ are as defined in formula (XXVII) in (xxxi) above, with a compound of formula (IX) as defined in (iv) above, in the presence of a base;

and optionally after (i), (ii), (iii), (iv), (v), (vi), (vii), (viii), (ix), (x), (xi), (xii), (xiii), (xiv), (xv), (xvi), (xvii), (xviii), (xix), (xx), (xxi), (xxii), (xxiii), (xxiv), (xxv), (xxvi), (xxvii), (xxviii), (xxix), (xxx), (xxxi) or (xxxii) converting the compound of formula (I) to a further compound of formula (I) and, if desired, forming a pharmaceutically acceptable salt or solvate of the compound of formula (I).

9. A pharmaceutical composition comprising a compound of formula (I), or a pharmaceutically acceptable salt or solvate thereof, as claimed in claim 1 in association with a pharmaceutically acceptable adjuvant, diluent or carrier.

10. A process for the preparation of a pharmaceutical composition as claimed in claim 9 which comprises mixing a compound of formula (I), or a pharmaceutically acceptable salt or solvate thereof, as defined in claim 1 with a pharmaceutically acceptable adjuvant, diluent or carrier.

11. A method of treating rheumatoid arthritis which comprises administering to a patient a therapeutically effective amount of a compound of formula (I), or a pharmaceutically acceptable salt or solvate thereof, as claimed in claim 1.

12. A method for treating an obstructive airways disease which comprises administering to a patient a therapeutically effective amount of a compund of formula (I), or a pharmaceutically acceptable salt or solvate thereof, as claimed in claim 1.

* * * * *